United States Patent
Thess et al.

(10) Patent No.: US 12,201,680 B2
(45) Date of Patent: Jan. 21, 2025

(54) NUCLEIC ACID COMPRISING OR CODING FOR A HISTONE STEM-LOOP AND A POLY(A) SEQUENCE OR A POLYADENYLATION SIGNAL FOR INCREASING THE EXPRESSION OF AN ENCODED PATHOGENIC ANTIGEN

(71) Applicant: CureVac SE, Tübingen (DE)

(72) Inventors: Andreas Thess, Kusterdingen (DE); Thomas Schlake, Gundelfingen (DE); Jochen Probst, Wolfschlugen (DE)

(73) Assignee: CureVac SE, Tübingen (DE)

( * ) Notice: Subject to any disclaimer, the term of this patent is extended or adjusted under 35 U.S.C. 154(b) by 1059 days.

(21) Appl. No.: 17/139,778

(22) Filed: Dec. 31, 2020

(65) Prior Publication Data

US 2021/0128716 A1    May 6, 2021

Related U.S. Application Data

(60) Division of application No. 16/938,136, filed on Jul. 24, 2020, now Pat. No. 10,912,826, which is a continuation of application No. 15/892,330, filed on Feb. 8, 2018, now Pat. No. 10,799,577, which is a continuation of application No. 15/465,322, filed on Mar. 21, 2017, now Pat. No. 10,166,283, which is a continuation of application No. 14/378,538, filed as application No. PCT/EP2013/000460 on Feb. 15, 2013, now Pat. No. 9,669,089, which is a continuation of application No. PCT/EP2012/000673, filed on Feb. 15, 2012.

(51) Int. Cl.

| *A61K 39/145* | (2006.01) |
| *A61K 39/00* | (2006.01) |
| *A61K 39/12* | (2006.01) |
| *C12N 7/00* | (2006.01) |
| *C12N 15/63* | (2006.01) |
| *C12N 15/67* | (2006.01) |

(52) U.S. Cl.
CPC ............ *A61K 39/145* (2013.01); *A61K 39/00* (2013.01); *A61K 39/12* (2013.01); *C12N 7/00* (2013.01); *C12N 15/63* (2013.01); *C12N 15/67* (2013.01); *A61K 2039/53* (2013.01); *A61K 2039/64* (2013.01); *C12N 2760/16134* (2013.01); *C12N 2770/20034* (2013.01); *C12N 2830/50* (2013.01); *Y02A 50/30* (2018.01)

(58) Field of Classification Search
None
See application file for complete search history.

(56) References Cited

U.S. PATENT DOCUMENTS

| 5,908,779 A | 6/1999 | Carmichael et al. |
| 6,783,961 B1 | 8/2004 | Edwards et al. |
| 6,822,072 B1 | 11/2004 | Edwards et al. |
| 7,432,049 B2 | 10/2008 | Liew et al. |
| 7,700,359 B2 | 4/2010 | Chan et al. |
| 8,217,016 B2 | 7/2012 | Hoerr et al. |
| 8,383,340 B2 | 2/2013 | Ketterer et al. |
| 8,703,906 B2 | 4/2014 | Baumhof et al. |
| 8,968,746 B2 | 3/2015 | Baumhof et al. |
| 9,155,788 B2 | 10/2015 | Hoerr et al. |
| 9,226,959 B2 | 1/2016 | Kramps et al. |
| 9,234,013 B2 | 1/2016 | Thess et al. |
| 9,314,535 B2 | 4/2016 | Baumhof et al. |
| 9,352,028 B2 | 5/2016 | Barner et al. |
| 9,402,887 B2 | 8/2016 | Probst et al. |
| 9,421,255 B2 | 8/2016 | Baumhof et al. |
| 9,433,669 B2 | 9/2016 | Hoerr et al. |
| 9,433,670 B2 | 9/2016 | Hoerr et al. |
| 9,439,956 B2 | 9/2016 | Hoerr et al. |
| 9,447,431 B2 | 9/2016 | Thess et al. |
| 9,463,228 B2 | 10/2016 | Hoerr et al. |
| 9,572,874 B2 | 2/2017 | Fotin-Mleczek et al. |
| 9,616,084 B2 | 4/2017 | Mutzke |
| 9,623,095 B2 | 4/2017 | Kallen et al. |
| 9,655,955 B2 | 5/2017 | Hoerr et al. |

(Continued)

FOREIGN PATENT DOCUMENTS

| WO | WO 1995/015394 | 6/1995 |
| WO | WO 1998/042856 | 10/1998 |

(Continued)

OTHER PUBLICATIONS

Attwood, "The babel of bioinformatics," *Science*, 290(5491):471-473, 2000.

(Continued)

*Primary Examiner* — Nianxiang Zou

(74) *Attorney, Agent, or Firm* — Parker Highlander PLLC

(57) ABSTRACT

The present invention relates to a nucleic acid sequence, comprising or coding for a coding region, encoding at least one peptide or protein comprising a pathogenic antigen or a fragment, variant or derivative thereof, at least one histone stem-loop and a poly(A) sequence or a polyadenylation signal. Furthermore the present invention provides the use of the nucleic acid for increasing the expression of said encoded peptide or protein. It also discloses its use for the preparation of a pharmaceutical composition, especially a vaccine, e.g. for use in the treatment of infectious diseases. The present invention further describes a method for increasing the expression of a peptide or protein comprising a pathogenic antigen or a fragment, variant or derivative thereof, using the nucleic acid comprising or coding for a histone stem-loop and a poly(A) sequence or a polyadenylation signal.

23 Claims, 24 Drawing Sheets

Specification includes a Sequence Listing.

(56) References Cited

U.S. PATENT DOCUMENTS

| | | |
|---|---|---|
| 9,669,089 B2 | 6/2017 | Thess et al. |
| 9,683,233 B2 | 6/2017 | Thess |
| 9,688,729 B2 | 6/2017 | Kramps et al. |
| 9,737,595 B2 | 8/2017 | Lorenz et al. |
| 9,839,697 B2 | 12/2017 | Thess et al. |
| 9,890,391 B2 | 2/2018 | Thess et al. |
| 9,907,862 B2 | 3/2018 | Baumhof et al. |
| 9,974,845 B2 | 5/2018 | Fotin-Mleczek et al. |
| 10,010,592 B2 | 7/2018 | Thess et al. |
| 10,017,826 B2 | 7/2018 | von der Mülbe et al. |
| 10,047,375 B2 | 8/2018 | Thess |
| 10,080,809 B2 | 9/2018 | Thess |
| 10,111,967 B2 | 10/2018 | Fotin-Mleczek et al. |
| 10,111,968 B2 | 10/2018 | Thess et al. |
| 10,117,920 B2 | 11/2018 | Fotin-Mleczek et al. |
| 10,150,797 B2 | 12/2018 | Kramps et al. |
| 10,166,283 B2 | 1/2019 | Thess et al. |
| 10,172,935 B2 | 1/2019 | Kallen et al. |
| 10,188,748 B2 | 1/2019 | Von der Mülbe et al. |
| 10,232,024 B2 | 3/2019 | Thess et al. |
| 10,293,058 B2 | 5/2019 | Fotin-Mleczek et al. |
| 10,293,060 B2 | 5/2019 | Baumhof |
| 10,307,472 B2 | 6/2019 | Fotin-Mleczek et al. |
| 10,369,216 B2 | 8/2019 | Fotin-Mleczek et al. |
| 10,434,154 B2 | 10/2019 | Probst et al. |
| 10,434,158 B2 | 10/2019 | Fotin-Mleczek et al. |
| 10,441,653 B2 | 10/2019 | Hoerr et al. |
| 10,501,768 B2 | 12/2019 | Eber et al. |
| 10,517,827 B2 | 12/2019 | Eber et al. |
| 10,568,958 B2 | 2/2020 | Baumhof et al. |
| 10,568,972 B2 | 2/2020 | Von der Mülbe et al. |
| 10,588,959 B2 | 3/2020 | Kallen et al. |
| 10,596,252 B2 | 3/2020 | Kallen et al. |
| 10,610,605 B2 | 4/2020 | Thess et al. |
| 10,648,017 B2 | 5/2020 | Wochner |
| 10,653,768 B2 | 5/2020 | Mutzke et al. |
| 10,653,799 B2 | 5/2020 | Thess et al. |
| 10,682,406 B2 | 6/2020 | Thess et al. |
| 10,682,426 B2 | 6/2020 | Schnee et al. |
| 10,702,600 B1 | 7/2020 | Ciaramella et al. |
| 10,711,315 B2 | 7/2020 | von der Mülbe et al. |
| 10,729,654 B2 | 8/2020 | Eber et al. |
| 10,729,761 B2 | 8/2020 | Kallen et al. |
| 10,738,306 B2 | 8/2020 | Thess |
| 10,751,424 B2 | 8/2020 | Baumhof et al. |
| 10,760,070 B2 | 9/2020 | Funkner et al. |
| 10,780,054 B2 | 9/2020 | Ketterer et al. |
| 10,799,577 B2 | 10/2020 | Thess et al. |
| 10,799,602 B2 | 10/2020 | Baumhof |
| 10,837,039 B2 | 11/2020 | Wochner et al. |
| 10,869,935 B2 | 12/2020 | Fotin-Mleczek et al. |
| 10,898,584 B2 | 1/2021 | Schlake et al. |
| 10,898,589 B2 | 1/2021 | Thess et al. |
| 10,912,826 B2 | 2/2021 | Thess et al. |
| 10,918,740 B2 | 2/2021 | Fotin-Mleczek et al. |
| 10,988,754 B2 | 4/2021 | Fotin-Mleczek et al. |
| 11,034,729 B2 | 6/2021 | Kramps et al. |
| 11,078,247 B2 | 8/2021 | Fotin-Mleczek et al. |
| 11,110,156 B2 | 9/2021 | Thess et al. |
| 11,110,157 B2 | 9/2021 | Fotin-Mleczek et al. |
| 11,110,166 B2 | 9/2021 | Fotin-Mleczek et al. |
| 11,135,312 B2 | 10/2021 | von der Mülbe et al. |
| 11,141,474 B2 | 10/2021 | Rauch et al. |
| 11,141,476 B2 | 10/2021 | Rauch |
| 11,149,278 B2 | 10/2021 | Thess et al. |
| 11,179,337 B2 | 11/2021 | Eber et al. |
| 11,225,682 B2 | 1/2022 | Reichert et al. |
| 11,241,493 B2 | 2/2022 | Rauch et al. |
| 11,248,223 B2 | 2/2022 | Yazdan Panah et al. |
| 11,254,951 B2 | 2/2022 | Thess |
| 11,266,735 B2 | 3/2022 | Kallen et al. |
| 11,268,157 B2 | 3/2022 | von der Mülbe et al. |
| 11,274,293 B2 | 3/2022 | Funkner et al. |
| 11,279,923 B2 | 3/2022 | Funkner et al. |
| 11,286,492 B2 | 3/2022 | Thess et al. |
| 2004/0038405 A1 | 2/2004 | Liu et al. |
| 2005/0009028 A1 | 1/2005 | Heintz et al. |
| 2005/0032730 A1 | 2/2005 | Von Der Mülbe et al. |
| 2005/0048549 A1 | 3/2005 | Cao et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2007/0111203 A1 | 5/2007 | Cao et al. |
| 2007/0172949 A9 | 7/2007 | Liu et al. |
| 2007/0280929 A1 | 12/2007 | Hoerr et al. |
| 2008/0025944 A1 | 1/2008 | Hoerr et al. |
| 2008/0171711 A1 | 7/2008 | Hoerr et al. |
| 2008/0267873 A1 | 10/2008 | Hoerr et al. |
| 2009/0324584 A1 | 12/2009 | Hoerr et al. |
| 2010/0047261 A1 | 2/2010 | Hoerr et al. |
| 2010/0048883 A1 | 2/2010 | Ketterer et al. |
| 2010/0120152 A1 | 5/2010 | Wooddell et al. |
| 2010/0129392 A1 | 5/2010 | Shi et al. |
| 2010/0189729 A1 | 7/2010 | Hoerr et al. |
| 2010/0203076 A1 | 8/2010 | Fotin-Mleczek et al. |
| 2010/0239608 A1 | 9/2010 | Von Der Mülbe et al. |
| 2010/0291156 A1 | 11/2010 | Barner et al. |
| 2010/0303851 A1 | 12/2010 | Hoerr et al. |
| 2010/0305196 A1 | 12/2010 | Probst et al. |
| 2011/0053829 A1 | 3/2011 | Baumhof et al. |
| 2011/0077287 A1 | 3/2011 | Von Der Mülbe et al. |
| 2011/0250225 A1 | 10/2011 | Fotin-Mleczek et al. |
| 2011/0269950 A1 | 11/2011 | Von Der Mülbe et al. |
| 2011/0311472 A1 | 12/2011 | Hoerr et al. |
| 2012/0009221 A1 | 1/2012 | Hoerr et al. |
| 2012/0021043 A1 | 1/2012 | Kramps et al. |
| 2012/0213818 A1 | 8/2012 | Hoerr et al. |
| 2012/0258046 A1 | 10/2012 | Mutzke |
| 2013/0121988 A1 | 5/2013 | Hoerr et al. |
| 2013/0129754 A1 | 5/2013 | Thess et al. |
| 2013/0142818 A1 | 6/2013 | Baumhof et al. |
| 2013/0195867 A1 | 8/2013 | Hoerr et al. |
| 2013/0202645 A1 | 8/2013 | Barner et al. |
| 2013/0251742 A1 | 9/2013 | Probst et al. |
| 2013/0259879 A1 | 10/2013 | Baumhof et al. |
| 2013/0273001 A1 | 10/2013 | Hoerr et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2014/0037660 A1 | 2/2014 | Fotin-Mleczek et al. |
| 2014/0147454 A1 | 5/2014 | Chakraborty et al. |
| 2014/0294877 A1 | 10/2014 | Baumhof et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess |
| 2015/0104476 A1 | 4/2015 | Von Der Mülbe et al. |
| 2015/0118183 A1 | 4/2015 | Baumhof |
| 2015/0118264 A1 | 4/2015 | Baumhof et al. |
| 2015/0141498 A1 | 5/2015 | Mutzke |
| 2015/0165006 A1 | 6/2015 | Thess et al. |
| 2015/0184195 A1 | 7/2015 | Thess et al. |
| 2015/0218554 A1 | 8/2015 | Thess |
| 2015/0258214 A1 | 9/2015 | Baumhof et al. |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0151474 A1 | 6/2016 | Kallen et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake et al. |
| 2016/0304883 A1 | 10/2016 | Grund et al. |
| 2016/0304938 A1 | 10/2016 | Wochner |
| 2016/0326575 A1 | 11/2016 | von der Mülbe |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wochner et al. |
| 2017/0182150 A1 | 6/2017 | Kallen et al. |
| 2017/0239372 A1 | 8/2017 | Baumhof et al. |

(56) References Cited

U.S. PATENT DOCUMENTS

| | | |
|---|---|---|
| 2017/0252430 A1 | 9/2017 | Fotin-Mleczek et al. |
| 2017/0266268 A1 | 9/2017 | Kallen et al. |
| 2017/0326225 A1 | 11/2017 | Rauch et al. |
| 2017/0340725 A1 | 11/2017 | Ciaramella et al. |
| 2018/0044687 A1 | 2/2018 | Thess et al. |
| 2018/0078629 A1 | 3/2018 | Lorenz et al. |
| 2018/0125952 A1 | 5/2018 | Fotin-Mleczek et al. |
| 2018/0126003 A1 | 5/2018 | Hoerr |
| 2018/0126005 A1 | 5/2018 | Fotin-Mleczek et al. |
| 2018/0142275 A1 | 5/2018 | Roos et al. |
| 2018/0148727 A1 | 5/2018 | Grund et al. |
| 2018/0207295 A1 | 7/2018 | Fotin-Mleczek et al. |
| 2018/0208957 A1 | 7/2018 | Roos et al. |
| 2018/0237786 A1 | 8/2018 | Schlake et al. |
| 2018/0237817 A1 | 8/2018 | Roos et al. |
| 2018/0256694 A1 | 9/2018 | Barner et al. |
| 2018/0296663 A1 | 10/2018 | Hipp et al. |
| 2018/0312545 A1 | 11/2018 | Baumhof et al. |
| 2018/0371392 A1 | 12/2018 | Mayer et al. |
| 2019/0008954 A1 | 1/2019 | Baumhof |
| 2019/0017100 A1 | 1/2019 | Wochner et al. |
| 2019/0024096 A1 | 1/2019 | Schmid et al. |
| 2019/0049414 A1 | 2/2019 | Wochner et al. |
| 2019/0083602 A1 | 3/2019 | Roos et al. |
| 2019/0100784 A1 | 4/2019 | Eber et al. |
| 2019/0151438 A1 | 5/2019 | Kallen et al. |
| 2019/0160164 A1 | 5/2019 | Rauch et al. |
| 2019/0177714 A1 | 6/2019 | Kunze et al. |
| 2019/0185859 A1 | 6/2019 | Fotin-Mleczek et al. |
| 2019/0194760 A1 | 6/2019 | Koch et al. |
| 2019/0225971 A1 | 7/2019 | Williams |
| 2019/0255161 A1 | 8/2019 | Thess et al. |
| 2019/0336608 A1 | 11/2019 | Baumhof et al. |
| 2019/0336611 A1 | 11/2019 | Baumhof et al. |
| 2019/0343933 A1 | 11/2019 | Horscroft et al. |
| 2019/0343942 A1 | 11/2019 | Fotin-Mleczek et al. |
| 2019/0345504 A1 | 11/2019 | Grund et al. |
| 2019/0351044 A1 | 11/2019 | Jasny et al. |
| 2019/0351047 A1 | 11/2019 | Jasny et al. |
| 2019/0365879 A1 | 12/2019 | Probst et al. |
| 2019/0381155 A1 | 12/2019 | Fotin-Mleczek et al. |
| 2019/0381180 A1 | 12/2019 | Baumhof et al. |
| 2020/0016264 A1 | 1/2020 | Hoerr et al. |
| 2020/0023076 A1 | 1/2020 | Fotin-Mleczek et al. |
| 2020/0040370 A1 | 2/2020 | Eber et al. |
| 2020/0085852 A1 | 3/2020 | Fotin-Mleczek |
| 2020/0085942 A1 | 3/2020 | Kramps et al. |
| 2020/0085943 A1 | 3/2020 | Baumhof et al. |
| 2020/0085944 A1 | 3/2020 | Heidenreich et al. |
| 2020/0149026 A1 | 5/2020 | Horscroft et al. |
| 2020/0163878 A1 | 5/2020 | Baumhof et al. |
| 2020/0179526 A1 | 6/2020 | Baumhof et al. |
| 2020/0197510 A1 | 6/2020 | Ciaramella et al. |
| 2020/0216878 A1 | 7/2020 | Wochner |
| 2020/0246451 A1 | 8/2020 | Mutzke et al. |
| 2020/0268908 A1 | 8/2020 | Schnee et al. |
| 2020/0276336 A1 | 9/2020 | Thess et al. |
| 2020/0316189 A1 | 10/2020 | Kallen et al. |
| 2020/0332293 A1 | 10/2020 | Thess |
| 2020/0338215 A1 | 10/2020 | Baumhof et al. |
| 2020/0383919 A1 | 12/2020 | Eber et al. |
| 2020/0383922 A1 | 12/2020 | Ketterer et al. |
| 2020/0392572 A1 | 12/2020 | Yazdan Panah et al. |
| 2020/0399322 A1 | 12/2020 | Baumhof et al. |
| 2021/0023199 A1 | 1/2021 | Kallen et al. |
| 2021/0030683 A1 | 2/2021 | Eber et al. |
| 2021/0030864 A1 | 2/2021 | Petsch et al. |
| 2021/0030866 A1 | 2/2021 | Kallen et al. |
| 2021/0040526 A1 | 2/2021 | Wochner et al. |
| 2021/0046179 A1 | 2/2021 | Fotin-Mleczek et al. |
| 2021/0060175 A1 | 3/2021 | Fotin-Mleczek et al. |
| 2021/0060181 A1 | 3/2021 | Thess et al. |
| 2021/0069315 A1 | 3/2021 | Baumhof et al. |
| 2021/0128716 A1 | 5/2021 | Thess et al. |
| 2021/0162037 A1 | 6/2021 | Jasny et al. |
| 2021/0170017 A1 | 6/2021 | Lutz et al. |
| 2021/0180106 A1 | 6/2021 | Wochner et al. |
| 2021/0187124 A1 | 6/2021 | Schlake et al. |
| 2021/0198649 A1 | 7/2021 | Fotin-Mleczek et al. |
| 2021/0205434 A1 | 7/2021 | Petsch et al. |
| 2021/0222178 A1 | 7/2021 | Linke et al. |
| 2021/0251898 A1 | 8/2021 | Baumhof et al. |
| 2021/0260178 A1 | 8/2021 | Jasny et al. |
| 2021/0261627 A1 | 8/2021 | Kramps et al. |
| 2021/0261897 A1 | 8/2021 | Yazdan Panah et al. |
| 2021/0308238 A1 | 10/2021 | Hoerr et al. |
| 2021/0361761 A1 | 11/2021 | Lutz et al. |
| 2021/0361764 A1 | 11/2021 | Fotin-Mleczek et al. |
| 2021/0369827 A1 | 12/2021 | Fotin-Mleczek et al. |
| 2021/0393755 A1 | 12/2021 | Thess et al. |
| 2021/0401966 A1 | 12/2021 | Rauch et al. |
| 2021/0401971 A1 | 12/2021 | Rauch |
| 2021/0403925 A1 | 12/2021 | Chevessier-Tünnesen et al. |
| 2022/0025369 A1 | 1/2022 | Fotin-Mleczek et al. |
| 2022/0040281 A1 | 2/2022 | Schwendt et al. |
| 2022/0073962 A1 | 3/2022 | Schwenger et al. |
| 2022/0090092 A1 | 3/2022 | Thess et al. |
| 2022/0096616 A1 | 3/2022 | Barner et al. |
| 2022/0119795 A1 | 4/2022 | Yazdan Panah et al. |
| 2022/0133908 A1 | 5/2022 | Rejman et al. |
| 2022/0136011 A1 | 5/2022 | Thess |
| 2022/0144877 A1 | 5/2022 | Heinz et al. |

FOREIGN PATENT DOCUMENTS

| | | |
|---|---|---|
| WO | WO 2001/007590 | 2/2001 |
| WO | WO 2001/012824 | 2/2001 |
| WO | WO 2002/085434 | 10/2002 |
| WO | WO 2002/098443 | 12/2002 |
| WO | WO 2003/059381 | 7/2003 |
| WO | WO 2005/035771 | 4/2005 |
| WO | WO 2005/040377 | 5/2005 |
| WO | WO 2006/008154 | 1/2006 |
| WO | WO 2006/022712 | 3/2006 |
| WO | WO 2006/024518 | 3/2006 |
| WO | WO 2006/122828 | 11/2006 |
| WO | WO 2006/123097 | 11/2006 |
| WO | WO 2007/024708 | 3/2007 |
| WO | WO 2007/068265 | 6/2007 |
| WO | WO 2008/014979 | 2/2008 |
| WO | WO 2008/077592 | 7/2008 |
| WO | WO 2008/083949 | 7/2008 |
| WO | WO 2009/030481 | 3/2009 |
| WO | WO 2009/046974 | 4/2009 |
| WO | WO 2009/046975 | 4/2009 |
| WO | WO 2009/095226 | 8/2009 |
| WO | WO 2009/127230 | 10/2009 |
| WO | WO 2009/155961 | 12/2009 |
| WO | WO 2010/023260 | 3/2010 |
| WO | WO 2010/037539 | 4/2010 |
| WO | WO 2010/088927 | 8/2010 |
| WO | WO 2010/132867 | 11/2010 |
| WO | WO 2011/026641 | 3/2011 |
| WO | WO 2011/069528 | 6/2011 |
| WO | WO 2011/069529 | 6/2011 |
| WO | WO 2011/069586 | 6/2011 |
| WO | WO 2011/069587 | 6/2011 |
| WO | WO 2011/144358 | 11/2011 |
| WO | WO 2012/013326 | 2/2012 |
| WO | WO 2012/019630 | 2/2012 |
| WO | WO 2012/019780 | 2/2012 |
| WO | WO 2012/089338 | 7/2012 |
| WO | WO 2012/113513 | 8/2012 |
| WO | WO 2012/116714 | 9/2012 |
| WO | WO 2012/116810 | 9/2012 |
| WO | WO 2012/116811 | 9/2012 |
| WO | WO 2013/113501 | 8/2013 |
| WO | WO 2013/113502 | 8/2013 |
| WO | WO 2013/113736 | 8/2013 |
| WO | WO 2013/120626 | 8/2013 |
| WO | WO 2013/120627 | 8/2013 |
| WO | WO 2013/120628 | 8/2013 |
| WO | WO 2013/120629 | 8/2013 |
| WO | WO 2013/143698 | 10/2013 |

(56) References Cited

FOREIGN PATENT DOCUMENTS

| | | |
|---|---|---|
| WO | WO 2013/143699 | 10/2013 |
| WO | WO 2013/143700 | 10/2013 |
| WO | WO 2013/174409 | 11/2013 |
| WO | WO 2014/127917 | 8/2014 |
| WO | WO 2015/024665 | 2/2015 |
| WO | WO 2015/024668 | 2/2015 |
| WO | WO 2015/062738 | 5/2015 |
| WO | WO 2015/101414 | 7/2015 |
| WO | WO 2015/101415 | 7/2015 |
| WO | WO 2015/101416 | 7/2015 |
| WO | WO 2015/135558 | 9/2015 |
| WO | WO 2015/149944 | 10/2015 |
| WO | WO 2016/107877 | 7/2016 |
| WO | WO 2016/165825 | 10/2016 |
| WO | WO 2016/165831 | 10/2016 |
| WO | WO 2016/174227 | 11/2016 |
| WO | WO 2016/174271 | 11/2016 |
| WO | WO 2016/184575 | 11/2016 |
| WO | WO 2016/184576 | 11/2016 |
| WO | WO 2016/184822 | 11/2016 |
| WO | WO 2016/193206 | 12/2016 |
| WO | WO 2016/193226 | 12/2016 |
| WO | WO 2016/203025 | 12/2016 |
| WO | WO 2017/001058 | 1/2017 |
| WO | WO 2017/009376 | 1/2017 |
| WO | WO 2017/021546 | 2/2017 |
| WO | WO 2017/025120 | 2/2017 |
| WO | WO 2017/025447 | 2/2017 |
| WO | WO 2017/036580 | 3/2017 |

OTHER PUBLICATIONS

Avni et al., "The 5' terminal oligopyrimidine tract confers translational control on TOP mRNAs in a cell type-and sequence context-dependent manner," *Nucleic Acids Research*, 25(5):995-1001, 1997.

Avni et al., "Vertebrate mRNAs with a 5'-terminal pyrimidine tract are candidates for translational repression in quiescent cells: characterization of the translational cis-regulatory element," *Mol. Cell. Biol.*, 14(6):3822-3833, 1994.

Battle and Doudna, "The stem-loop binding protein forms a highly stable and specific complex with the 3' stem-loop of histone mRNAs", *RNA*, 7:123-132, 2001.

Blumenthal et al., "Definition of an allergen (immunobiology)," *Allergens and Allergen Immunotherapy*, Ed. R. Lockey, S. Bukantz and J. Bousquet, pp. 37-50, 2004.

Caldarola et al., "Translational regulation of terminal oligopyrimidine mRNAs induced by serum and amino acids involves distinct signaling events," *The Journal of Biological Chemistry*, 279(14):13522-135531, 2004.

Cameron et al., "Recent advances in transgenic technology," *Molecular Biotechnology*, 7:253-265, 1997.

Chakrabarti et al., "The mammalian target of rapamycin complex 1 regulates leptin biosynthesis in adipocytes at the level of translation: the role of the 5'-untranslated region in the expression of leptin messenger ribonucleic acid," *Molecular Endocrinology*, 22(10):2260-2267, 2008.

Cheung et al., "Specific interaction of HeLa cell proteins with coxsackievirus B3 3'UTR: La autoantigen binds the 3' and 5' UTR independently of the poly(A) tail," *Cell Microbiol.*, 9(7):1705-1715, 2007.

Collart et al., "A human histone H2B.1 variant gene, located on chromosome 1, utilizes alternative 3' end processing", *Journal of Cellular Biochemistry*, 50:374-385, 1992.

Damgaard and Lykke-Andersen, "Translational coregulation of 5'TOP mRNAs by TIA-1 and TIAR," *Genes Dev.*, 25:2057-2068, 2011.

Database EMBL Accession No. EM_STD:AB063609, "*Homo sapiens* RPL36AL mRNA for ribosomal protein L36a-like, complete cds," 2002.

Database GenBank, [online], Accession No. AK222475, Nov. 17, 2007, <https://www.ncbi.nlm.nih.gov/nuccore/62896508?sat=46&satkey=15856460>.

Database GenBank, [online], Accession No. AK222780, Nov. 17, 2007, <https://www.ncbi.nlm.nih.gov/nuccore/62897118?sat=46&satkey=15856751>.

Database GenBank, [online], Accession No. D28385, Mar. 10, 2009, <https://www.ncbi.nlm.nih.gov/nuccore/461233?sat=46&satkey=15629526>.

Database GenBank, [online], Accession No. D28406, Jan. 22, 2005, <https://www.ncbi.nlm.nih.gov/nuccore/461241?sat=46&satkey=15629534>.

Database GenBank, [online], Accession No. D28448, Jan. 22, 2005, <https://www.ncbi.nlm.nih.gov/nuccore/461226?sat=46&satkey=15629520>.

Database GenBank, [online], Accession No. NM_001199291, Mar. 5, 2012, <https://www.ncbi.nlm.nih.gov/nuccore/313482809?sat=15&satkey=6403420>.

Database GenBank, [online], Accession No. NM_004046, Mar. 24, 2012, <https://www.ncbi.nlm.nih.gov/nuccore/50345980?sat=15&satkey=6379190>.

Database GenBank, [online], Accession No. NM_004374, Jan. 23, 2012, <https://www.ncbi.nlm.nih.gov/nuccore/301069354?sat=15&satkey=6401626>.

Database Geneseq Accession No. ATN08647, "Human transcriptional regulatory element Seq ID No. 6587," 2008.

Database Nucleotide, "Human ribosomal protein L9 mRNA, complete cds," XP002729678, Database accession No. U09953.1, 1996.

Davuluri et al., "CART classification of human 5' UTR sequences," *Genome Research*, 10(11):1807-1816, 2000.

Declaration Under 37 C.F.R. § 1.132, submitted in U.S. Appl. No. 15/195,934, filed Feb. 9, 2018.

Deml et al., "Multiple effects of codon usage optimization on expression and immunogenicity of DNA candidate vaccines encoding the human immunodeficiency virus type 1 Gag protein," *Journal of Virology*, 75(22):10991-11001, 2001.

Dhamija et al., "IL-1-induced Post-transcriptional Mechanisms Target Overlapping Translational Silencing and Destabilizing Elements in IKBC mRNA," *J. Biol. Chem.*, 285(38):29165-29178, 2010.

Dollé et al., "Nerve growth factor overexpression and autocrine loop in breast cancer cells," *Oncogene*, 22(36):5592-5601, 2003.

Dominski et al., "Stem-loop binding protein facilitates 3'-end formation by stabilizing U7 snRNP binding to histone pre-mRNA," *Mol Cell Biol.*, 19(5):3561-3570, 1999.

Dugaiczyk et al., "Nucleotide sequence and the encoded amino acids of human serum albumin mRNA," *Proc. Natl. Acad. Sci. USA*, 79:71-75, 1982.

Eckner et al., "Mature mRNA 3' end formation stimulates RNA export from the nucleus," *The EMBO Journal*, 10(11):3513-3522, 1991.

Gallie et al., "The histone 3'-terminal stem-loop is necessary for translation in Chinese hamster ovary cells", *Nucleic Acids Res.*, 24(10):1954-62, 1996.

Gerwitz et al., "Nucleic acid therapeutics: state of the art and future prospects," *Blood*, 92(3):712-736, 1998.

Ginn et al., "Gene therapy clinical trails worldwide to 2012—an update," *Journal of Gene Medicine*, 15:65-77, 2013.

Gorgoni et al., "The stem-loop binding protein stimulates histone translation at an early step in the initiation pathway," *RNA*, 11:1030-1042, 2005.

Haines et al., "CL22—a novel cationic peptide for efficient transfection of mammalian cells," *Gene Ther.*, 8:99-110, 2001.

Henke et al., "Coxsackievirus B3 vaccines: use as an expression vector for prevention of myocarditis," *Expert Rev. Vaccines*, 7(10):1557-1567, 2008.

Hoeksema et al., "Placing the RPL32 Promoter Upstream of a Second Promoter Results in a Strongly Increased Number of Stably Transfected Mammalian Cell Lines That Display High Protein Expression Levels," Biotechnol. Res. Int., 2011(492875):1-11, 2011.

Holtkamp et al., "Modification of antigen-encoding RNA increases stability, translational efficacy, and T-cell stimulatory capacity of dendritic cells", *Blood*, 108(13):4009-17, 2006.

(56) References Cited

OTHER PUBLICATIONS

Iadevaia et al., "All translation elongation factors and the e, f, and h subunits of translation initiation factor 3 are encoded by 5'-terminal oligopyrimidine (TOP) mRNAs," *RNA*, 14:1730-1736, 2008.
International Search Report and Written Opinion issued in the corresponding PCT Application No. PCT/EP2014/003480, mailed on Aug. 10, 2015.
Kato et al., "Construction of a human full-length cDNA bank," Gene, 150:243-250, 1994.
Kato et al., "Histone H2B as an antigen recognized by lung cancer-specific human monoclonal antibody HB4C5", *Human Antibodies and Hybridomas*, 2(2):94-101, 1991.
Kenmochi et al., "A map of 75 human ribosomal protein genes," Gene Res., 8(5):509-523, 1998.
Kim et al., "Coxsackievirus B3 used as a gene therapy vector to express functional FGF2," *Gene Ther.*, 19(12):1159-1165, 2012.
Kim et al., "Systematic analysis of attenuated *Coxsackievirus* expressing a foreign gene as a viral vaccine vector," *Vaccine*, 28(5):1234-1240, 2010.
Knapinska et al., "Molecular mechanisms regulation mRNA stability: physiological and pathological significance," *Current Genomics*, 6(6):1-16, 2005.
Kramarova et al., "A sequence predicted to form a stem-loop is proposed to be required for formation of an RNA-protein complex involving the 3'UTR of β-subunit $F_0F_1$-ATPase mRNA," *Biochim. Biophys. Acta.*, 1777(7-8):747-757, 2008.
Kübler et al., "Self-adjuvanted mRNA vaccination in advanced prostate cancer patients: a first-in-man phase I/IIa study," *Journal of ImmunoTherapy of Cancer*, 3:26, 2015.
Kudla et al., "High guanine and cytosine content increases mRNA levels in mammalian cells," *PLoS Biology*, 4:0933-0942, 2006.
Ledda et al., "Effect of 3' UTR length on the translational regulation of 5'-terminal oligopyrimidine mRNAs," *Gene*, 344:213-220, 2005.
Levy et al., "Oligopyrimidine tract at the 5' end of mammalian ribosomal protein mRNAs is required for their translational control," *Proc. Natl. Acad. Sci. USA*, 88:3319-3323, 1991.
Levy et al., "Sequence and functional characterization of the terminal exon of the human insulin receptor gene", *Biochim Biophys Acta.*, 1263(3):253-7, 1995.
Ling et al., "The histone 3'-terminal stem-loop-binding protein enhances translation through a functional and physical interaction with eukaryotic initiation factor 4G (eIF4G) and eIF3", *Mol Cell Biol.*, 22(22):7853-67, 2002.
Lopez and Samuelsson, "Early evolution of histone mRNA 3' end processing", *Bioinformatics*, 14(1):1-10, 2008.
Lorenzi et al., "Intranasal vaccination with messenger RNA as a new approach in gene therapy: use against tuberculosis," *BMC Biotechnology*, 10:77, 2010.
Mazuruk et al., "Structural organization and chromosomal localization of the human ribosomal protein L9 gene," Biochim. Biophys. Acta, 1305(3):151-162, 1996.
Meier et al., "Fibroblast growth factor-2 but not Mel-CAM and/or β3 integrin promotes progression of melanocytes to melanoma," *Exp. Dermatol.*, 12(3):296-306, 2003.
Meyuhas, "Synthesis of the translational apparatus is regulated at the translational level," *Eur. J. Biochem.*, 267:6321-6330, 2000.
Mignone et al., "Untranslated regions of mRNAs," Genome Biol., 3(3):1-10, 2002.
Montoliu, "Gene transfer strategies in animal transgenesis," *Cloning and Stem Cells*, 4(1):39-46, 2002.
Moor et al., "Mechanisms of translational control by the 3' UTR in development and differentiation," Sem. Cell Develop. Biol., 16(1):49-58, 2005.
Narita et al., "NELF interacts with CDC and participates in 3' end processing of replication-dependent histone mRNAs", *Molecular Cell*, 26(3):349-365, 2007.
Ngo et al., "Computational complexity, protein structure prediction, and the levinthal paradox," *The Protein Folding Problem and Tertiary Structure Prediction*, Ed. K. Merz and S. Le Grand, pp. 491-495, 1994.

Niemann, "Transgenic farm animals get off the ground," *Transgenic Research*, 7:73-75, 1998.
Office Communication issued in U.S. Appl. No. 13/321,474, mailed Apr. 6, 2015.
Office Communication issued in U.S. Appl. No. 13/321,474, mailed May 20, 2014.
Office Communication issued in U.S. Appl. No. 14/378,538, mailed Jun. 21, 2016.
Office Communication issued in U.S. Appl. No. 14/378,538, mailed Nov. 12, 2015.
Office Communication issued in U.S. Appl. No. 14/378,538, mailed Oct. 11, 2016.
Office Communication issued in U.S. Appl. No. 14/378,572, mailed Aug. 12, 2016.
Office Communication issued in U.S. Appl. No. 14/378,572, mailed Mar. 14, 2017.
Office Communication issued in U.S. Appl. No. 14/378,572, mailed Mar. 3, 2016.
Office Communication issued in U.S. Appl. No. 14/378,572, mailed Sep. 21, 2017.
Office Communication issued in U.S. Appl. No. 14/378,591, mailed Aug. 22, 2016.
Office Communication issued in U.S. Appl. No. 14/378,591, mailed Apr. 9, 2018.
Office Communication issued in U.S. Appl. No. 14/378,591, mailed Aug. 23, 2017.
Office Communication issued in U.S. Appl. No. 14/378,591, mailed Jan. 27, 2017.
Office Communication issued in U.S. Appl. No. 14/378,606, mailed May 27, 2015.
Office Communication issued in U.S. Appl. No. 14/378,606, mailed Nov. 3, 2015.
Office Communication issued in U.S. Appl. No. 14/388,224, mailed Apr. 21, 2016.
Office Communication issued in U.S. Appl. No. 14/388,224, mailed Jul. 28, 2017.
Office Communication issued in U.S. Appl. No. 14/388,224, mailed Oct. 17, 2016.
Office Communication issued in U.S. Appl. No. 14/388,226, mailed Jun. 21, 2016.
Office Communication issued in U.S. Appl. No. 14/388,226, mailed Nov. 6, 2015.
Office Communication issued in U.S. Appl. No. 14/945,349, mailed Feb. 6, 2017.
Office Communication issued in U.S. Appl. No. 15/233,933, mailed Apr. 6, 2018.
Office Communication issued in U.S. Appl. No. 15/233,933, mailed Dec. 7, 2017.
Office Communication issued in U.S. Appl. No. 15/233,933, mailed Jul. 28, 2017.
Office Communication issued in U.S. Appl. No. 15/465,322, mailed Apr. 2, 2018.
Office Communication issued in U.S. Appl. No. 15/465,322, mailed Nov. 20, 2017.
Office Communication issued in U.S. Appl. No. 15/590,370, mailed Apr. 30, 2018.
Office Communication issued in U.S. Appl. No. 15/590,370, mailed May 1, 2019.
Office Communication issued in U.S. Appl. No. 15/590,370, mailed Oct. 3, 2018.
Office Communication issued in U.S. Appl. No. 15/810,080, mailed Apr. 22, 2019.
Office Communication issued in U.S. Appl. No. 15/810,080, mailed Jul. 30, 2019.
Office Communication issued in U.S. Appl. No. 15/892,330, mailed Jan. 7, 2020.
Office Communication issued in U.S. Appl. No. 15/892,330, mailed Jul. 30, 2019.
Office Communication issued in U.S. Appl. No. 15/892,356, mailed Jul. 30, 2019.
Office Communication issued in U.S. Appl. No. 15/892,356, mailed Oct. 21, 2019.

(56) References Cited

OTHER PUBLICATIONS

Office Communication issued in U.S. Appl. No. 15/899,326, mailed May 23, 2018.
Office Communication issued in U.S. Appl. No. 15/899,336, mailed Jul. 12, 2019.
Office Communication issued in U.S. Appl. No. 15/899,336, mailed Jun. 30, 2020.
Office Communication issued in U.S. Appl. No. 15/899,336, mailed Mar. 13, 2020.
Office Communication issued in U.S. Appl. No. 15/899,336, mailed Nov. 1, 2019.
Office Communication issued in U.S. Appl. No. 15/899,336, mailed Sep. 17, 2020.
Office Communication issued in U.S. Appl. No. 16/002,695, mailed Apr. 24, 2020.
Office Communication issued in U.S. Appl. No. 16/002,695, mailed May 10, 2021.
Office Communication issued in U.S. Appl. No. 16/002,695, mailed Oct. 27, 2020.
Office Communication issued in U.S. Appl. No. 16/030,018, mailed Aug. 3, 2020.
Office Communication issued in U.S. Appl. No. 16/030,018, mailed Feb. 26, 2021.
Office Communication issued in U.S. Appl. No. 16/030,018, mailed Oct. 15, 2021.
Office Communication issued in U.S. Appl. No. 16/263,913, mailed Oct. 13, 2021.
Office Communication issued in U.S. Appl. No. 16/938,136, mailed Sep. 2, 2020.
Office Communication issued in U.S. Appl. No. 16/938,136, mailed Nov. 12, 2020.
Office Communication issued in U.S. Appl. No. 16/938,136, mailed Dec. 16, 2020.
Oliveira et al., "Inhibition of translational initiation in *Saccharomyces cerevisiae* by secondary structure: the roles of the stability and position of stem-loops in the mRNA leader," *Mol. Microbiol.*, 9(3):521-532, 1993.
Orom et al., "MicroRNA-10a binds the 5'UTR of ribosomal protein mRNAs and enhances their translation," *Molecular Cell*, 30:460-471, 2008.
Palmowski et al., "Intravenous injection of a lentiviral vector encoding NY-ESO-1 induces an effective CTL response," *J. Immunol.*, 172(3):1582-1587, 2004.
Pandey et al., "Introns in histone genes alter the distribution of 3' ends", *Nucleic Acids Res.*, 18(11):3161-70, 1990.
PCT International Search Report and Written Opinion issued in International Application No. PCT/EP2013/000938, mailed Nov. 13, 2013.
PCT International Search Report and Written Opinion issued in International Application No. PCT/EP2013/000937, mailed Aug. 30, 2013.
PCT International Search Report and Written Opinion issued in International Application No. PCT/EP2013/000461, mailed Apr. 16, 2013.
PCT International Search Report and Written Opinion issued in International Application No. PCT/EP2013/000458, mailed Apr. 24, 2013.
PCT International Search Report and Written Opinion issued in International Application No. PCT/EP2013/000459, mailed Apr. 23, 2013.
PCT International Search Report and Written Opinion issued in International Application No. PCT/EP2013/000460, mailed Apr. 22, 2013.
PCT International Search Report and Written Opinion issued in International Application No. PCT/EP2011/004077, mailed Nov. 10, 2011.
Prelle et al., "Establishment of pluripotent cell lines from vertebrate species—present status and future prospects," *Cells Tissues Organs*, 165:220-236, 1999.
Ristevski, "Making better transgenic models," *Molecular Biotechnology*, 29:153-163, 2005.
Roesler et al., "Immunize and disappear—safety-optimized mRNA vaccination with a panel of 29 allergens", *Journal of Allergy and Clinical Immunology*, 124(5):1070-1077, 2009.
Russell et al., "The stability of human beta-globin mRNA is dependent on structural determinants positioned within its 3' untranslated region", Blood, 87:5314-5323, 1996.
Sanchez et al., "Increased levels of polyadenylated histone H2B mRNA accumulate during *Entamoeba invadens* cyst formation", *Molecular and Biochemical Parasitology*, 67(1):137-146, 1994.
Sánchez et al., "The oligo(A) tail on histone mRNA plays an active role in translational silencing of histone mRNA during Xenopus oogenesis", *Mol Cell Biol.*, 24(6):2513-25, 2004.
Schlake et al., "Developing mRNA-vaccine technologies," RNA Biol., 9(11):1319-1330, 2012.
Sequence alignment of Seq ID No. 1368 of U.S. Pat. No. 10,738,306 with Seq ID No. 12385 of U.S. Pat. No. 7,700,359, sequence search conducted on Aug. 18, 2019; 2 pages. (Year: 2019).
Sequence alignment of Seq ID No. 1452 of U.S. Pat. No. 10,738,306 with Seq ID No. 12350 of U.S. Pat. No. 7,432,049, sequence search conducted on Aug. 18, 2019; 2 pages. (Year: 2019).
Sequence alignment of Seq ID No. 1453 of U.S. Pat. No. 10,738,306 with Seq ID No. 55428 of U.S. Pat. No. 7,432,049, sequence search conducted on Aug. 18, 2019; 1 page. (Year: 2019).
Sequence alignment of Seq ID No. 1454 of U.S. Pat. No. 10,738,306 with Seq ID No. 184 of U.S. Pat. No. 6,783,961, sequence search conducted on Aug. 18, 2019; 1 page. (Year: 2019).
Sequence alignment of Seq ID No. 1455 of U.S. Pat. No. 10,738,306 with Seq ID No. 1476 of U.S. Pat. No. 6,783,961, sequence search conducted on Aug. 18, 2019; 1 page. (Year: 2019).
Sequence alignment of Seq ID No. 1456 of U.S. Pat. No. 10,738,306 with Seq ID No. 787 of U.S. Pat. No. 6,822,072, sequence search conducted on Aug. 18, 2019; 1 page. (Year: 2019).
Sequence alignment of Seq ID No. 1457 of U.S. Pat. No. 10,738,306 with Seq ID No. 55594 of U.S. Pat. No. 7,432,049, sequence search conducted on Aug. 18, 2019; 1 page. (Year: 2019).
Sequence alignment of Seq ID No. 1458 of U.S. Pat. No. 10,738,306 with Seq ID No. 8351 of U.S. Pat. No. 6,783,961, sequence search conducted on Aug. 18, 2019; 1 page. (Year: 2019).
Sharma et al., "Functional role of the 5' terminal cloverleaf in Coxsackievirus RNA replication," *Virology*, 393(2):238-249, 2009.
Shen and Higgins, "The 5' untranslated region-mediated enhancement of intracellular listeriolysin O production is required for *Listeria monocytogenes* pathogenicity," *Molecular Microbiology*, 57(5):1460-1473, 2005.
Shen et al., "Structures required for poly(A) tail-independent translation overlap with, but ar distinct from, cap-independent translation and RNA replication signals at the 3' end of *Tobacco necrosis virus* RNA," *Virology*, 358:448-458, 2007.
Shuptrine et al., "Monoclonal antibodies for the treatment of cancer," *Seminars in Cancer Biology*, 22:3-13, 2012.
Sigmund, "Viewpoint: are studies in genetically altered mice out of control?" *Arteriosclerosis, Thrombosis, and Vascular Biology*, 20:1425-1429, 2000.
Skolnick et al., "From genes to protein structure and function: novel applications of computational approaches in the genomic era," *Trends in Biotech.*, 18:34-39, 2000.
Smith, "Gene transfer in higher animals: theoretical considerations and key concepts," *Journal of Biotechnology*, 99:1-22, 2002.
Stauber et al., "A signal regulating mouse histone H4 mRNA levels in a mammalian cell cycle mutant and sequences controlling RNA 3' processing are both contained within the same 80-bp fragment", EMBO J., 5(12):3297-303, 1986.
Svoboda et al., "Hairpin RNA: a secondary structure of primary importance", Cell Mol Life Sci., 63(7-8):901-8, 2006.
Thess et al., "Sequence-engineered mRNA without chemical nucleoside modifications enables an effective protein therapy in large animals," *Molecular Therapy*, pp. 1-9 and Supplementary Material, 2015.
Thran et al., "mRNA mediates passive vaccination against infectious agents, toxins, and tumors", EMBO Mol. Med., 9(10):1434-1447, 2017.

(56) References Cited

OTHER PUBLICATIONS

Van Dijk et al., "Identification of RNA sequences and structures involved in site-specific cleavage of IGF-II mRNAs," *RNA*, 1623-1635, 1998.

Van Ooij et al., "Polyadenylation of genomic RNA and initiation of antigenomic RNA in a positive-strand RNA virus are controlled by the same cis-element," *Nucleic Acids Res.*, 34(10):2953-2965, 2006.

Wagner et al., "A genome-wide RNA interference screen reveals that variant histones are necessary for replication-dependent histone pre-mRNA processing", *Molecular Cell*, 28(4):692-699, 2007.

Weiss et al., "Prophylactic mRNA vaccination against allergy", Current Opinion in Allergy and Clinical Immunology, 10(6):567-574, 2010.

Wilkie et al., "Regulation of mRNA translation by 5'- and 3'-UTR-binding factors," Trends Biochem. Sci., 28(4):182-188, 2003.

Williams et al., "A simple, highly efficient method for heterologous expression in mammalian primary neurons using cationic lipid-mediated mRNA transfection", *Frontiers in Neuroscience*, 4:1-20, 2010.

Wooddell et al., "Sustained liver-specific transgene expression from the albumin promoter in mice following hydrodynamic plasmid DNA delivery," *The Journal of Gene Medicine*, 10:551-563, 2008.

Yamashita et al., "Comprehensive detection of human terminal oligo-pyrimidine (TOP) genes and analysis of their characteristics," *Nucleic Acids Res*, 36(11):3707-3715 and Supplementary Data (six pages), 2008.

Zhong et al., "A double-stranded RNA binding protein required for activation of repressed messages in mammalian germ cells", *Nat Genet.*, 22(2):171-4, 1999.

Zhu et al., "Binding of the La autoantigen to the 5' untranslated region of a chimeric human translation elongation factor 1A reporter mRNA inhibits translation in vitro," *Biochimica et Biophysica Acta*, 1521:19-29, 2001.

Pandey & Marzluff, "The Stem-Loop Structure at the 3' End of Histone mRNA is Necessary and Sufficient for Regulation of Histone mRNA Stability," Molecular and Cellular Biology, 4557-4559, 1987.

| # A | # T | # C | # C | Cons | 99% | 95% | 90% | | |
|---|---|---|---|---|---|---|---|---|---|
| 2224 | 172 | 1557 | 25 | N* | H* | N* | M* | | |
| 1586 | 188 | 2211 | 16 | N* | H* | H* | M* | | |
| 3075 | 47 | 875 | 4 | N | H | M | M | | |
| 2872 | 205 | 918 | 6 | N | H | H | M | | |
| 1284 | 19 | 2675 | 23 | N | A | M | M | | |
| 184 | 6 | 270 | 3541 | N | A | S | S | ^ | ⎫ |
| 0 | 0 | 0 | 4001 | G | G | G | G | ^ | ⎪ |
| 13 | 569 | 3394 | 25 | N | Y | Y | Y | ^ | ⎬ Stem 1 |
| 12 | 1620 | 2342 | 27 | N | Y | Y | Y | ^ | ⎪ |
| 9 | 199 | 3783 | 10 | N | Y | Y | C | ^ | ⎪ |
| 1 | 3947 | 51 | 2 | N | Y | T | T | ^ | ⎭ |
| 47 | 3830 | 119 | 5 | N | H | T | T | • | ⎫ |
| 59 | 3704 | 227 | 11 | N | H | Y | T | • | ⎬ Loop |
| 0 | 4001 | 0 | 0 | T | T | T | T | • | ⎪ |
| 675 | 182 | 3140 | 4 | N | H | M | M | • | ⎭ |
| 3818 | 1 | 7 | 175 | N | R | A | A | v | ⎫ |
| 195 | 21 | 50 | 3735 | N | A | R | G | v | ⎪ |
| 1596 | 15 | 31 | 2359 | N | A | R | R | v | ⎬ Stem 2 |
| 523 | 11 | 16 | 3451 | N | R | R | R | v | ⎪ |
| 0 | 0 | 4001 | 0 | C | C | C | C | v | ⎪ |
| 14 | 179 | 3543 | 265 | N | B | S | S | v | ⎭ |
| 3727 | 8 | 154 | 112 | N | A | M | A | | |
| 61 | 64 | 3870 | 4 | N | H | C | C | | |
| 771 | 557 | 2636 | 37 | N* | H* | H* | H* | | |
| 2012 | 201 | 1744 | 43 | N* | N* | H* | M* | | |
| 2499 | 690 | 674 | 138 | N* | N* | H* | H* | | |

Figure 1

| #A | #T | #C | #G | Cons | 99% | 95% | 90% | Region |
|---|---|---|---|---|---|---|---|---|
| 2172 | 152 | 1512 | 11 | N* | H* | M* | M* | |
| 1554 | 156 | 2152 | 8 | N* | H* | M* | M* | |
| 3004 | 10 | 855 | 1 | N | M | M | M | |
| 2790 | 184 | 893 | 3 | N | H | M | M | |
| 1208 | 11 | 2637 | 14 | N | M | M | M | |
| 171 | 3 | 270 | 3426 | N | V | S | S | ^ Stem 1 |
| 0 | 0 | 0 | 3870 | G | G | G | G | ^ |
| 1 | 548 | 3308 | 13 | N | Y | Y | Y | ^ |
| 0 | 1535 | 2334 | 1 | B | Y | Y | Y | ^ |
| 0 | 141 | 3729 | 0 | Y | Y | C | C | ^ |
| 0 | 9 | 3861 | 0 | Y | T | T | T | ^ |
| 1 | 3760 | 106 | 3 | N | Y | T | T | • Loop |
| 56 | 3639 | 169 | 6 | N | H | Y | T | • |
| 0 | 3870 | 0 | 0 | T | T | T | T | • |
| 600 | 154 | 3113 | 3 | N | H | M | M | • |
| 3736 | 0 | 5 | 129 | V | R | A | A | v Stem 2 |
| 142 | 4 | 44 | 3680 | N | V | G | G | v |
| 1517 | 2 | 0 | 2351 | D | R | R | R | v |
| 503 | 1 | 6 | 3360 | N | R | R | R | v |
| 0 | 0 | 3870 | 0 | C | C | C | C | v |
| 10 | 164 | 3431 | 265 | N | B | S | S | v |
| 3633 | 1 | 149 | 87 | N | V | M | A | |
| 44 | 33 | 3788 | 3 | N | M | C | C | |
| 736 | 525 | 2578 | 31 | N* | H* | H* | H* | |
| 1938 | 181 | 1714 | 36 | N* | H* | H* | M* | |
| 2443 | 662 | 634 | 131 | N* | N* | H* | H* | |

Figure 3

| #A | #T | #C | Cons | 99% | 95% | 90% | |
|---|---|---|---|---|---|---|---|
| 661 | 63 | 8 | N* | H* | H* | M* | |
| 146 | 121 | 1062 | N* | H* | H* | M* | |
| 1315 | 2 | 16 | H | M | A | A | |
| 1323 | 2 | 6 | N | A | A | A | |
| 920 | 6 | 403 | N | M | M | M | |
| 8 | 2 | 1322 | N | G | G | G | ⎫ |
| 0 | 0 | 1333 | G | G | G | G | ⎬ |
| 1 | 39 | 1293 | H | Y | C | C | ⎬ Stem 1 |
| 0 | 1217 | 116 | Y | Y | Y | T | ⎬ |
| 0 | 2 | 1331 | Y | C | C | C | ⎬ |
| 0 | 1331 | 2 | Y | T | T | T | ⎭ |
| 1 | 1329 | 0 | D | T | T | T | ⎫ |
| 4 | 1207 | 121 | N | Y | Y | T | ⎬ Loop |
| 0 | 1333 | 0 | T | T | T | T | ⎬ |
| 441 | 30 | 862 | H | H | M | M | ⎭ |
| 1333 | 0 | 0 | A | A | A | A | ⎫ |
| 0 | 1 | 1330 | B | G | G | G | ⎬ |
| 1199 | 0 | 134 | R | R | R | R | ⎬ Stem 2 |
| 21 | 1 | 1311 | D | R | G | G | ⎬ |
| 0 | 0 | 1333 | C | C | C | C | ⎬ |
| 1 | 2 | 1328 | N | C | C | C | ⎭ |
| 1126 | 1 | 128 | N | A | A | M | |
| 26 | 22 | 1284 | N | H | C | C | |
| 81 | 91 | 1143 | N* | N* | H* | Y* | |
| 380 | 91 | 834 | N* | N* | H* | M* | |
| 960 | 12 | 361 | H* | M* | M* | M* | |

Figure 4

| #A | #T | #C | #C | Cons | 99% | 95% | 90% | | |
|---|---|---|---|---|---|---|---|---|---|
| 10 | 8 | 62 | 4 | N* | N* | H* | H* | | |
| 17 | 6 | 61 | 0 | H* | H* | H* | M* | | |
| 84 | 0 | 0 | 0 | A | A | A | A | | |
| 84 | 0 | 0 | 0 | A | A | A | A | | |
| 76 | 2 | 6 | 0 | H | H | W | A | | |
| 1 | 2 | 0 | 81 | D | D | G | G | ^ | Stem 1 |
| 0 | 0 | 0 | 84 | G | G | G | G | ^ | |
| 1 | 1 | 82 | 0 | H | H | C | C | ^ | |
| 0 | 67 | 17 | 0 | Y | Y | Y | Y | ^ | |
| 0 | 0 | 84 | 0 | C | C | C | C | ^ | |
| 0 | 84 | 0 | 0 | T | T | T | T | ^ | |
| 1 | 80 | 0 | 3 | D | D | T | T | • | Loop |
| 0 | 81 | 3 | 0 | Y | Y | T | T | • | |
| 0 | 84 | 0 | 0 | T | T | T | T | • | |
| 12 | 5 | 67 | 0 | H | H | H | W | • | |
| 84 | 0 | 0 | 0 | A | A | A | A | v | Stem 2 |
| 0 | 0 | 1 | 83 | S | S | C | C | v | |
| 65 | 0 | 0 | 19 | R | R | R | R | v | |
| 0 | 0 | 0 | 81 | R | R | G | G | v | |
| 0 | 0 | 84 | 0 | C | C | C | C | v | |
| 0 | 0 | 84 | 0 | C | C | C | C | v | |
| 69 | 0 | 5 | 10 | V | V | V | R | | |
| 5 | 4 | 75 | 0 | H | H | M | M | | |
| 0 | 25 | 57 | 2 | B* | B* | Y* | Y* | | |
| 10 | 24 | 44 | 6 | N* | N* | N* | H* | | |
| 64 | 3 | 17 | 0 | H* | H* | M* | M* | | |

Figure 5 ppLuc(GC) – ag gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCUCCUCCCCUCCUUGCACCGagauua
auagauc-3′

Figure 6 ppLuc(GC) – ag – A64 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAA-3'

Figure 7 ppLuc(GC) – ag – histoneSL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auagaucu<u>CAAAGGCUCUUUUCAGAGCCACCA</u>-3'

Figure 8 ppLuc(GC) – ag – A64 – histoneSL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcauCAAAGGCUCUUUUCAGAGCCACCA-3′

Figure 9 ppLuc(GC) – ag – A120 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auagaucuAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAA
AAAAAAAA-3'

Figure 10 ppLuc(GC) – ag – A64 – ag gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcauCCUGCCCGAUGGGCCUCCCAACGGGCCUCCUCCCCUCCUUGCACCG3'

Figure 11 ppLuc(GC) – ag – A64 – aCPSL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCUCCUCCCCUCCUUGCACCGagauua
auAAAAAAAAAAAAAAAAAAAAAAAAAAAAAAAAAAAAAAAAAAAAAAAAAAAAAAAAAAA
AAAAAAugcau*CAAUUCCUACACGUGAGGCGCUGUGAUUCCCUAUCCCCCUUCAUUCCCU
AUACAUUAGCACAGCGCCAUUGCAUGUAGGAAUU-3'*

Figure 12 ppLuc(GC) – ag – A64 – PolioCL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcauCAAUUCUAAAACAGCUCUGGGGUUGUACCCACCCCAGAGGCCCACGUGG
CGGCUAGUACUCCGGUAUUGCGGUACCCUUGUACGCCUGUUUUAGAAUU-3'

Figure 13 ppLuc(GC) – ag – A64 – G30 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAAAA
AAAAAAugcau*GGGGGGGGGGGGGGGGGGGGGGGGGGGGGG*-3'

Figure 14 ppLuc(GC) – ag – A64 – U30 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugca*UUUUUUUUUUUUUUUUUUUUUUUUUUUUUU*-3'

Figure 15 ppLuc(GC) – ag – A64 – SL gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcau*UAUGGCGGCCGUGUCCACCACGGAUAUCACCGUGGUGGACGCGGCC*-3'

Figure 16 ppLuc(GC) – ag – A64 – N32 gggagaaagcuugaggAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAgacuaguuaua
agacugacuaGCCCGAUGGGCCUCCCAACGGGCCCUCCUCCCCUCCUUGCACCGagauua
auAAAAAAAAAAAAAAAAAAAAAAAAAAAAAAAAAAAAAAAAAAAAAAAAAAAAAAAAAA
AAAAAAugcau*CCCCCUCUAGACAAUUGGAAUUCCAUA*-3'

GGGAGAAAGCUUACCAUGAAGGCCAACC

H1N1(PR8) – ag – A64 – C30 – histoneSL

GGGAGAAAGCUUACCAUGAAGGCCAACCUGCUCGUGCUGCUGUGCGCCCUCGCGGCCGCC
GACGCCGACACCAUCUGCAUCGGCUACCACGCCAACAACAGCACCGACACGGUCGACACC
GUGCUGGAGAAGAACGUGACCGUCACCCACUCCGUGAACCUGCUCGAGGACAGCCACAAC
GGGAAGCUGUGCCGGCUGAAGGGCAUCGCGCCCUCCAGCUGGGGAAGUGCAACAUCGCC
GGCUGGCUGCUCGGGAACCCGGAGUGCGACCCCUGCUGCCCGUGCGCUCCUGGAGCUAC
AUCGUCGAGACGCCCAACUCCGAGAACGGCAUCUGCUACCCGGGCGACUUCAUCGACUAC
GAGGAGCUCCGGGAGCAGCUGAGCUCCGUGAGCUCCUUCGAGCGCUUCGAGAUCUUCCCC
AAGGAGAGCUCCUGGCCCAACCACAACACCAACGGGGUGACCGCCGCCUGCAGCCACGAG
GGCAAGUCCAGCUUCUACCGGAACCUGCUCUGGCUGACCGAGAAGGAGGGGUCCUACCCC
AAGCUGAAGAACAGCUACGUCAACAAGAAGGGCAAGGAGGUGCUCGUGCUGUGGGGGAUC
CACCACCCGCCCAACUCCAAGGAGCAGCAGAACCUGUACCAGAACGAGAACGCGUACGUC
AGCGUGGUGACGUCCAACUACAACCGCCGGUUCACCCCCGAGAUCGCCGAGCGCCCCAAG
GUCCGGGACCAGGCCGGCCGCAUGAACUACUACUGGACCCUCCUGAAGCCGGGCGACACC
AUCAUCUUCGAGGCCAACGGGAACCUGAUCGCCCCGAUGUACGCGUUCGCCCUCAGCCGG
GGCUUCGGGAGCGGCAUCAUCACGUCCAACGCCAGCAUGCACGAGUGCAACACCAAGUGC
CAGACCCCCCUGGGCGCCAUCAACUCCAGCCUGCCCUACCAGAACAUCCACCCGGUGACC
AUCGGGGAGUGCCCCAAGUACGUGCGCUCCGCCAAGCUCCGGAUGGUCACGGGCCUGCGC
AACAACCCCAGCAUCCAGUCCCGGGGGCUGUUCGGCGCGAUCGCCGGGUUCAUCGAGGGC
GGCUGGACCGGGAUGAUCGACGGCUGGUACGGGUACCACCACCAGAACGAGCAGGGCAGC
GGGUACGCCGCCGACCAGAAGUCCACCCAGAACGCCAUCAACGGCAUCACCAACAAGGUG
AACACGGUGAUCGAGAAGAUGAACAUCCAGUUCACCGCGGUCGGCAAGGAGUUCAACAAG
CUCGAGAAGCGCAUGGAGAACCUGAACAAGAAGGUGGACGACGGGUUCCUGGACAUCUGG
ACCUACAACGCCGAGCUCCUGGUGCUGCUCGAGAACGAGCGGACCCUGGACUUCCACGAC
AGCAACGUCAAGAACCUGUACGAGAAGGUGAAGUCCCAGCUCAAGAACAACGCCAAGGAG
AUCGGCAACGGGUGCUUCGAGUUCUACCACAAGUGCGACAACGAGUGCAUGGAGAGCGUC
CGCAACGGCACGUACGACUACCCCAAGUACUCCGAGGAGAGCAAGCUGAACCGGGAGAAG
GUGGACGGGGUGAAGCUGGAGUCCAUGGGCAUCUACCAGAUCCUCGCCAUCUACAGCACC
GUCGCCUCCAGCCUGGUGCUGCUGGUGUCCCUCGGCGCGAUCAGCUUCUGGAUGUGCAGC
AACGGGUCCCUGCAGUGCCGCAUCUGCAUCUGAccacuaguuauaagacugacuaGCCCG
AUGGGCCUCCCAACGGGCCCUCCUCCCCUCCUUGCACCGagauuaauAAAAAAAAAAAAAA
AAAAAAAAAAAAAAAAAAAAAAAAAAAAAAAAAAAAAAAAAAAAAAAAAAAAUGCAUCCCC
CCCCCCCCCCCCCCCCCCCCCCCCCAAAGGCUCUUUCAGAGCCACCAgaauu

Figure 19

```
                        SEQUENCE LISTING

<160> NUMBER OF SEQ ID NOS: 58

<210> SEQ ID NO 1
<211> LENGTH: 16
<212> TYPE: RNA
<213> ORGANISM: artificial
<220> FEATURE:
<223> OTHER INFORMATION: histone stem-loop sequence according to formula
      (Ic): metazoan and protozoan histone stem-loop consensus sequence
      without stem bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (3)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (10)..(14)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (16)..(16)
<223> OTHER INFORMATION: n is selected from a nucleotide selected from
      A, U, T, G and C, or a nucleotide analogue thereof

<400> SEQUENCE: 1
ngnnnnnnun nnnncn                                                     16

<210> SEQ ID NO 2
<211> LENGTH: 26
<212> TYPE: RNA
<213> ORGANISM: artificial
<220> FEATURE:
<223> OTHER INFORMATION: histone stem-loop sequence according to formula
      (IIc): metazoan and protozoan histone stem-loop consensus sequence
      with stem bordering elements
<220> FEATURE:
<221> NAME/KEY: misc_feature
<222> LOCATION: (1)..(6)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (15)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (21)..(26)
<223> OTHER INFORMATION: n is selected from a nucleotide selected from
      A, U, T, G and C, or a nucleotide analogue thereof

<400> SEQUENCE: 2
nnnnnngnnn nnnunnnnnc nnnnnn                                          26

<210> SEQ ID NO 3
```

```
<211> LENGTH: 16
<212> TYPE: RNA
<213> ORGANISM: artificial
<220> FEATURE:
<223> OTHER INFORMATION: histone stem-loop sequence according to formula
      (Id): without stem bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (3)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (10)..(14)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (16)..(16)
<223> OTHER INFORMATION: n is selected from a nucleotide selected from
      A, U, T, G and C, or a nucleotide analogue thereof

<400> SEQUENCE: 3
ncnnnnnnun nnnngn                                              16

<210> SEQ ID NO 4
<211> LENGTH: 26
<212> TYPE: RNA
<213> ORGANISM: artificial
<220> FEATURE:
<223> OTHER INFORMATION: histone stem-loop sequence according to formula
      (IId): with stem bordering elements
<220> FEATURE:
<221> NAME/KEY: misc_feature
<222> LOCATION: (1)..(6)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (15)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (21)..(26)
<223> OTHER INFORMATION: n is selected from a nucleotide selected from
      A, U, T, G and C, or a nucleotide analogue thereof

<400> SEQUENCE: 4
nnnnnncnnn nnnunnnnng nnnnnn                                   26

<210> SEQ ID NO 5
<211> LENGTH: 16
<212> TYPE: RNA
<213> ORGANISM: artificial
<220> FEATURE:
<223> OTHER INFORMATION: histone stem-loop sequence according to formula
      (Ie): protozoan histone stem-loop consensus sequence without stem
      bordering elements
<220> FEATURE:
<221> NAME/KEY: misc_feature
<222> LOCATION: (3)..(8)
<223> OTHER INFORMATION: n is selected from a nucleotide selected from
      A, U, T, G and C, or a nucleotide analogue thereof
<220> FEATURE:
```

```
<221> NAME/KEY: misc_feature
<222> LOCATION: (10)..(14)
<223> OTHER INFORMATION: n is selected from a nucleotide selected from
      A, U, T, G and C, or a nucleotide analogue thereof

<400> SEQUENCE: 5
dgnnnnnnun nnnnch                                                 16

<210> SEQ ID NO 6
<211> LENGTH: 26
<212> TYPE: RNA
<213> ORGANISM: artificial
<220> FEATURE:
<223> OTHER INFORMATION: histone stem-loop sequence according to formula
      (IIe): protozoan histone stem-loop consensus sequence with stem
      bordering elements
<220> FEATURE:
<221> NAME/KEY: misc_feature
<222> LOCATION: (1)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (15)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (22)..(26)
<223> OTHER INFORMATION: n is selected from a nucleotide selected from
      A, U, T, G and C, or a nucleotide analogue thereof

<400> SEQUENCE: 6
nnnnndgnnn nnnunnnnnc hnnnnn                                      26

<210> SEQ ID NO 7
<211> LENGTH: 16
<212> TYPE: RNA
<213> ORGANISM: artificial
<220> FEATURE:
<223> OTHER INFORMATION: histone stem-loop sequence according to formula
      (If): metazoan histone stem-loop consensus sequence without stem
      bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (3)..(3)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (7)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (10)..(10)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (12)..(12)
<223> OTHER INFORMATION: n is selected from a nucleotide selected from
      A, U, T, G and C, or a nucleotide analogue thereof
<220> FEATURE:
<221> NAME/KEY: misc_feature
```

```
<222> LOCATION: (14)..(14)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (16)..(16)
<223> OTHER INFORMATION: n is selected from a nucleotide selected from
      A, U, T, G and C, or a nucleotide analogue thereof

<400> SEQUENCE: 7
ngnbyynnun vndncn                                                   16

<210> SEQ ID NO 8
<211> LENGTH: 26
<212> TYPE: RNA
<213> ORGANISM: artificial
<220> FEATURE:
<223> OTHER INFORMATION: histone stem-loop sequence according to formula
      (IIf): metazoan histone stem-loop consensus sequence with stem
      bordering elements
<220> FEATURE:
<221> NAME/KEY: misc_feature
<222> LOCATION: (1)..(6)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (12)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (15)..(15)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (17)..(17)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (19)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (21)..(26)
<223> OTHER INFORMATION: n is selected from a nucleotide selected from
      A, U, T, G and C, or a nucleotide analogue thereof

<400> SEQUENCE: 8
nnnnnngnby ynnunvndnc nnnnnn                                        26

<210> SEQ ID NO 9
<211> LENGTH: 16
<212> TYPE: RNA
<213> ORGANISM: artificial
<220> FEATURE:
<223> OTHER INFORMATION: histone stem-loop sequence according to formula
      (Ig): vertebrate histone stem-loop consensus sequence without stem
      bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(8)
```

```
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (16)..(16)
<223> OTHER INFORMATION: n is selected from a nucleotide selected from
      A, U, T, G and C, or a nucleotide analogue thereof

<400> SEQUENCE: 9
nghyyydnuh abrdcn                                                         16

<210> SEQ ID NO 10
<211> LENGTH: 26
<212> TYPE: RNA
<213> ORGANISM: artificial
<220> FEATURE:
<223> OTHER INFORMATION: histone stem-loop sequence according to formula
      (IIg): vertebrate histone stem-loop consensus sequence with stem
      bordering elements
<220> FEATURE:
<221> NAME/KEY: misc_feature
<222> LOCATION: (1)..(2)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (4)..(6)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (13)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (21)..(25)
<223> OTHER INFORMATION: n is selected from a nucleotide selected from
      A, U, T, G and C, or a nucleotide analogue thereof

<400> SEQUENCE: 10
nnhnnnghyy ydnuhabrdc nnnnnh                                              26

<210> SEQ ID NO 11
<211> LENGTH: 16
<212> TYPE: RNA
<213> ORGANISM: artificial
<220> FEATURE:
<223> OTHER INFORMATION: histone stem-loop sequence according to formula
      (Ih): humane histone stem-loop consensus sequence (Homo sapiens)
      without stem bordering elements

<400> SEQUENCE: 11
dghycudyuh asrrcc                                                         16

<210> SEQ ID NO 12
<211> LENGTH: 26
<212> TYPE: RNA
<213> ORGANISM: artificial
<220> FEATURE:
<223> OTHER INFORMATION: histone stem-loop sequence according to formula
      (IIh): human histone stem-loop consensus sequence (Homo sapiens)
      with stem bordering elements
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (25)..(25)
<223> OTHER INFORMATION: n is selected from a nucleotide selected from
      A, U, T, G and C, or a nucleotide analogue thereof
```

-continued

```
<400> SEQUENCE: 12
nhaahdghyc udyuhasrrc cvhbnh                                          26

<210> SEQ ID NO 13
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ic)

<400> SEQUENCE: 13
vgyyyyhhth rvvrcb                                                     16

<210> SEQ ID NO 14
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ic)

<400> SEQUENCE: 14
sgyyyttytm arrrcs                                                     16

<210> SEQ ID NO 15
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ic)

<400> SEQUENCE: 15 sgyyctttttm agrrcs                                                    16

<210> SEQ ID NO 16
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ie)
<220> FEATURE:
<221> NAME/KEY: misc_feature
<222> LOCATION: (3)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (7)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (12)..(14)
<223> OTHER INFORMATION: n is selected from a nucleotide selected from
      A, U, T, G and C, or a nucleotide analogue thereof

<400> SEQUENCE: 16
dgnnnbnnth vnnnch                                                     16

<210> SEQ ID NO 17
<211> LENGTH: 16
<212> TYPE: DNA
<213> ORGANISM: artificial
<220> FEATURE:
<223> OTHER INFORMATION: histone stem-loop sequences (without stem-
```

-continued

```
      bordering elements) according to formula (Ie)
<220> FEATURE:
<221> NAME/KEY: misc_feature
<222> LOCATION: (3)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (13)..(14)
<223> OTHER INFORMATION: n is selected from a nucleotide selected from
      A, U, T, G and C, or a nucleotide analogue thereof

<400> SEQUENCE: 17
rgnnnyhbth rdnncy                                                     16

<210> SEQ ID NO 18
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ie)
<220> FEATURE:
<221> NAME/KEY: misc_feature
<222> LOCATION: (3)..(3)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (14)..(14)
<223> OTHER INFORMATION: n is selected from a nucleotide selected from
      A, U, T, G and C, or a nucleotide analogue thereof

<400> SEQUENCE: 18
rgndbyhyth rdhncy                                                     16

<210> SEQ ID NO 19
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (If)

<400> SEQUENCE: 19
vgyyytyhth rvrrcb                                                     16

<210> SEQ ID NO 20
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (If)

<400> SEQUENCE: 20
sgyycttytm agrrcs                                                     16

<210> SEQ ID NO 21
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (If)

<400> SEQUENCE: 21 sgyyctttm agrrcs                                                      16
```

```
<210> SEQ ID NO 22
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ig)

<400> SEQUENCE: 22
ggyycttyth agrrcc                                                     16

<210> SEQ ID NO 23
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ig)

<400> SEQUENCE: 23
ggcycttytm agrgcc                                                     16

<210> SEQ ID NO 24
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ig)

<400> SEQUENCE: 24
ggctcttttm agrgcc                                                     16

<210> SEQ ID NO 25
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ih)

<400> SEQUENCE: 25
dghyctdyth asrrcc                                                     16

<210> SEQ ID NO 26
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ih)

<400> SEQUENCE: 26
ggcyctttth agrgcc                                                     16

<210> SEQ ID NO 27
<211> LENGTH: 16
<212> TYPE: DNA
<213> ORGANISM: artificial
<220> FEATURE:
<223> OTHER INFORMATION: histone stem-loop sequences (without stem-
      bordering elements) according to formula (Ih)

<400> SEQUENCE: 27 ggcyctttm agrgcc                                                      16

<210> SEQ ID NO 28
```

```
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIc)
<220> FEATURE:
<221> NAME/KEY: misc_feature
<222> LOCATION: (25)..(26)
<223> OTHER INFORMATION: n is selected from a nucleotide selected from
      A, U, T, G and C, or a nucleotide analogue thereof

<400> SEQUENCE: 28
hhhhvvgyyy yhhthrvvrc bvhhnn                                          26

<210> SEQ ID NO 29
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIc)

<400> SEQUENCE: 29
mhmhmsgyyy ttytmarrrc smchhh                                          26

<210> SEQ ID NO 30
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIc)

<400> SEQUENCE: 30
mmmmmsgyyc ttttmagrrc sachmh                                          26

<210> SEQ ID NO 31
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIe)
<220> FEATURE:
<221> NAME/KEY: misc_feature
<222> LOCATION: (1)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(10)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (12)..(13)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (17)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (22)..(22)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (24)..(26)
<223> OTHER INFORMATION: n is selected from a nucleotide selected from
```

A, U, T, G and C, or a nucleotide analogue thereof

<400> SEQUENCE: 31
nnnnndgnnn bnnthvnnnc hnhnnn         26

<210> SEQ ID NO 32
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIe)
<220> FEATURE:
<221> NAME/KEY: misc_feature
<222> LOCATION: (1)..(2)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (5)..(5)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(10)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (18)..(19)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (25)..(26)
<223> OTHER INFORMATION: n is selected from a nucleotide selected from
      A, U, T, G and C, or a nucleotide analogue thereof

<400> SEQUENCE: 32
nnhhnrgnnn yhbthrdnnc ydhhnn         26

<210> SEQ ID NO 33
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIe)
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (8)..(8)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (19)..(19)
<223> OTHER INFORMATION: n is selected from a nucleotide selected from
      A, U, T, G and C, or a nucleotide analogue thereof

<400> SEQUENCE: 33
nhhhvrgndb yhythrdhnc yrhhhh         26

<210> SEQ ID NO 34
<211> LENGTH: 26
<212> TYPE: DNA
<213> ORGANISM: artificial
<220> FEATURE:
<223> OTHER INFORMATION: histone stem-loop sequence (with stem bordering elements) according to formula (IIf)
<220> FEATURE:
<221> NAME/KEY: misc_feature
<222> LOCATION: (26)..(26)
<223> OTHER INFORMATION: n is selected from a nucleotide selected from
      A, U, T, G and C, or a nucleotide analogue thereof

<400> SEQUENCE: 34
hhmhmvgyyy tyhthrvrrc bvmhhn                                           26

<210> SEQ ID NO 35
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIf)

<400> SEQUENCE: 35
mmmmmsgyyc ttytmagrrc smchhh                                           26

<210> SEQ ID NO 36
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIf)

<400> SEQUENCE: 36
mmmmmsgyyc ttttmagrrc sachmh                                           26

<210> SEQ ID NO 37
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIg)
<220> FEATURE:
<221> NAME/KEY: misc_feature
<222> LOCATION: (24)..(25)
<223> OTHER INFORMATION: n is selected from a nucleotide selected from
      A, U, T, G and C, or a nucleotide analogue thereof

<400> SEQUENCE: 37
hhmamggyyc ttythagrrc cvhnnm                                           26

<210> SEQ ID NO 38
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIg)

<400> SEQUENCE: 38
hhaamggcyc ttytmagrgc cvchhm                                           26

<210> SEQ ID NO 39
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIg)

<400> SEQUENCE: 39

```
mmaamggctc ttttmagrgc cmcymm                                     26
```

<210> SEQ ID NO 40
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIh)
<220> FEATURE:
<221> NAME/KEY: misc_feature
<222> LOCATION: (1)..(1)
<223> OTHER INFORMATION: n is selected from a nucleotide selected from
      A, U, T, G and C, or a nucleotide analogue thereof
<220> FEATURE:
<221> NAME/KEY: misc_feature
<222> LOCATION: (25)..(25)
<223> OTHER INFORMATION: n is selected from a nucleotide selected from
      A, U, T, G and C, or a nucleotide analogue thereof

<400> SEQUENCE: 40

```
nhaahdghyc tdythasrrc cvhbnh                                     26
```

<210> SEQ ID NO 41
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIh)
<220> FEATURE:
<221> NAME/KEY: misc_feature
<222> LOCATION: (25)..(25)
<223> OTHER INFORMATION: n is selected from a nucleotide selected from
      A, U, T, G and C, or a nucleotide analogue thereof

<400> SEQUENCE: 41

```
hhaamggcyc tttthagrgc cvmynm                                     26
```

<210> SEQ ID NO 42
<211> LENGTH: 26
<212> TYPE: DNA
<213> ORGANISM: artificial
<220> FEATURE:
<223> OTHER INFORMATION: histone stem-loop sequence (with stem bordering
      elements) according to formula (IIh)

<400> SEQUENCE: 42

```
hmaaaggcyc ttttmagrgc crmyhm                                     26
```

<210> SEQ ID NO 43
<211> LENGTH: 1747
<212> TYPE: RNA
<213> ORGANISM: artificial
<220> FEATURE:
<223> OTHER INFORMATION: mRNA sequence of ppLuc(GC)-ag

<400> SEQUENCE: 43

```
gggagaaagc uugaggaugg aggacgccaa gaacaucaag aagggcccgg cgcccuucua    60
cccgcuggag gacgggaccg ccggcgagca gcuccacaag gccaugaagc gguacgcccu   120
ggugccgggc acgaucgccu ucaccgacgc ccacaucgag gucgacauca ccuacgcgga   180
guacuucgag augagcgugc gccuggccga ggccaugaag cgguacggcc ugaacaccaa   240
ccaccggauc gugguguhcu cggagaacag ccugcaguuc uucaugccgg ugcugggcgc   300
ccucuucauc ggcguggccg ucgccccggc gaacgacauc uacaacgagc gggagcugcu   360
gaacagcaug gggaucagcc agccgaccgu ggguucgug agcaagaagg gccugcagaa   420
```

```
gauccugaac gugcagaaga agcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg acaagacca ucgcccugau     600 caugaacagc agcggcagca ccggccugcc aaggggggug gcccugccgc accgaccgc     660 cugcgugcgc uucucgcacg cccgggaccc caucuucggc aaccagauca ucccggacac    720
cgccauccug agcguggugc cguuccacca cggcuucggc auguucacga cccugggcua    780
ccucaucugc ggcuuccggg uggaccugau guaccgguuc gaggaggagc uguuccugcg    840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg aggugggcga ggccguggcc aagcgguucc accucccggg   1020
cauccgccag ggcuacggcc ugaccgagac cacgagcgcg auccugauca cccccgaggg   1080
ggacgacaag ccgggcgccg ugggcaaggu ggucccguuc uucgaggcca ggugguggaa   1140
ccuggacacc ggcaagaccc ugggcgugaa ccagcggggc gagcugugcg ugcggggggcc   1200 gaugaucaug agcggcuacg ugaacaaccc ggaggccacc aacgcccuca ucgacaagga   1260
cggcuggcug cacagcggcg acaucgccua cugggacgag gacgagcacu ucuucaucgu   1320
cgaccggcug aagucgcuga ucaaguacaa gggcuaccag guggcgccgg ccgagcugga   1380
gagcauccug cuccagcacc ccaacaucuu cgacgccggc guggccgggc ugccggacga   1440
cgacgccggc gagcugccgg ccgcgguggu ggugcuggag cacggcaaga ccaugacgga   1500
gaaggagauc gucgacuacg uggccagcca ggugaccacc gccaagaagc ugcggggcgg   1560
cguggguuuc guggacgagg ucccgaaggg ccugaccggg aagcucgacg cccggaagau   1620
ccgcgagauc cugaucaagg ccaagaaggg cggcaagauc gccguguaag acuaguuaua   1680
agacugacua gcccgauggg ccucccaacg ggcccuccuc cccuccuugc accgagauua   1740
auagauc                                                            1747
```

<210> SEQ ID NO 44
<211> LENGTH: 1806
<212> TYPE: RNA
<213> ORGANISM: artificial
<220> FEATURE:
<223> OTHER INFORMATION: mRNA sequence of ppLuc(GC)-ag-A64

<400> SEQUENCE: 44

```
gggagaaagc uugaggaugg aggacgccaa gaacaucaag aagggcccgg cgcccuucua     60
cccgcuggag gacgggaccg ccggcgagca gcuccacaag gccaugaagc gguacgcccu    120
ggugccgggc acgaucgccu ucaccgacgc ccacaucgag gucgacauca ccuacgcgga    180
guacuucgag augagcgugc gccuggccga ggccaugaag cgguacggcc ugaacaccaa    240
ccaccggauc gugguguvcu cggagaacag ccugcaguuc uucaugccgg ugcugggcgc    300
ccucuucauc ggcguggccg ucgccccggc gaacgacauc uacaacgagc gggagcugcu    360
gaacagcaug gggaucagcc agccgaccgu ggugvucgug agcaagaagg gccugcagaa    420
gauccugaac gugcagaaga agcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg acaagacca ucgcccugau     600 caugaacagc agcggcagca ccggccugcc aaggggggug gcccugccgc accgaccgc     660
```

| | |
|---|---|
| cugcgugcgc uucucgcacg cccgggaccc caucuucggc aaccagauca ucccggacac | 720 |
| cgccauccug agcguggugc cguuccacca cggcuucggc auguuacgca cccugggcua | 780 |
| ccucaucugc ggcuuccggg uggaccugau guaccgguuc gaggaggagc uguuccugcg | 840 |
| gagccugcag gacuacaaga uccagagcgc gcugcucgug ccgacccugu ucagcuucuu | 900 |
| cgccaagagc acccugaucg acaaguacga ccugucgaac cugcacgaga ucgccagcgg | 960 |
| gggcgccccg cugagcaagg aggugggcga ggccguggcc aagcgguucc accucccggg | 1020 |
| cauccgccag ggcuacggcc ugaccgagac cacgagcgcg auccugauca cccccgaggg | 1080 |
| ggacgacaag ccgggcgccg ugggcaaggu gguccccguuc uucgaggcca agguggugga | 1140 |
| ccuggacacc ggcaagaccc ugggcgugaa ccagcggggc gagcugugcg ugcggggggcc | 1200 |
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag cacggcaaga ccaugacgga | 1500 |
| gaaggagauc gucgacuacg uggccagcca ggugaccacc gccaagaagc ugcggggcgg | 1560 |
| cgugguguuc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgauggg ccucccaacg ggcccuccuc cccuccuugc accgagauua | 1740 |
| auaaaaaaaa aaaaaaaaaa aaaaaaaaaa aaaaaaaaaa aaaaaaaaaa aaaaaaaaaa | 1800 |
| aaaaaa | 1806 |

<210> SEQ ID NO 45
<211> LENGTH: 1772
<212> TYPE: RNA
<213> ORGANISM: artificial
<220> FEATURE:
<223> OTHER INFORMATION: mRNA sequence of ppLuc(GC)-ag-histoneSL

<400> SEQUENCE: 45

| | |
|---|---|
| gggagaaagc uugaggaugg aggacgccaa gaacaucaag aagggcccgg cgcccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacgccc ugaacaccaa | 240 |
| ccaccggauc guggugugcu cggagaacag ccugcaguuc uucaugccgg ugcugggcgc | 300 |
| ccucuucauc ggcguggccg ucgccccggc gaacgacauc uacaacgagc gggagcugcu | 360 |
| gaacagcaug gggaucagcc agccgaccgu ggguuucgug agcaagaagg gccugcagaa | 420 |
| gauccugaac gugcagaaga gcugcccau cauccagaag aucaucauca uggacagcaa | 480 |
| gaccgacuac cagggcuucc agucgaugua cacguucgug accagccacc uccgccgggg | 540 |
| cuucaacgag uacgacuucg ucccggagag cuucgaccgg acaagaccca ucgcccugau | 600 |
| caugaacagc agcggcagca ccggccugcc gaaggggggug gcccugccgc accgaccgc | 660 |
| cugcgugcgc uucucgcacg cccgggaccc caucuucggc aaccagauca ucccggacac | 720 |
| cgccauccug agcguggugc cguuccacca cggcuucggc auguuacgca cccugggcua | 780 |
| ccucaucugc ggcuuccggg uggaccugau guaccgguuc gaggaggagc uguuccugcg | 840 |
| gagccugcag gacuacaaga uccagagcgc gcugcucgug ccgacccugu ucagcuucuu | 900 |

```
cgccaagagc acccugaucg acaaguacga ccugucgaac cugcacgaga ucgccagcgg    960
gggcgccccg cugagcaagg aggugggcga ggccguggcc aagcgguucc accucccggg   1020
cauccgccag ggcuacggcc ugaccgagac cacgagcgcg auccugauca ccccgaggg    1080
ggacgacaag ccgggcgccg ugggcaaggu gguccccguuc uucgaggcca agguggugga  1140
ccuggacacc ggcaagaccc ugggcgugaa ccagcggggc gagcugugcg ugcgggggcc   1200
gaugaucaug agcggcuacg ugaacaaccc ggaggccacc aacgcccuca ucgacaagga   1260
cggcuggcug cacagcggcg acaucgccua cugggacgag gacgagcacu ucuucaucgu   1320
cgaccggcug aagucgcuga ucaaguacaa gggcuaccag guggcgccgg ccgagcugga   1380
gagcauccug cuccagcacc ccaacaucuu cgacgccggc guggccgggc ugccggacga   1440
cgacgccggc gagcugccgg ccgcgguggu ggugcuggag cacggcaaga ccaugacgga   1500
gaaggagauc gucgacuacg uggccagcca ggugaccacc gccaagaagc ugcggggcgg   1560
cguggugusc guggacgagg ucccgaaggg ccugaccggg aagcucgacg cccggaagau   1620
ccgcgagauc cugaucaagg ccaagaaggg cggcaagauc gccguguaag acuaguuaua   1680
agacugacua gcccgauggg ccucccaacg ggcccuccuc cccuccuugc accgagauua   1740
auagaucuca aaggcucuuu ucagagccac ca                                 1772

<210> SEQ ID NO 46
<211> LENGTH: 1835
<212> TYPE: RNA
<213> ORGANISM: artificial
<220> FEATURE:
<223> OTHER INFORMATION: mRNA sequence of ppLuc(GC)-ag-A64-histoneSL

<400> SEQUENCE: 46
gggagaaagc uugaggaugg aggacgccaa gaacaucaag aagggcccgg cgcccuucua     60
cccgcuggag gacgggaccg ccggcgagca gcuccacaag gccaugaagc gguacgcccu    120
ggugccgggc acgaucgccu ucaccgacgc ccacaucgag gucgacauca ccuacgcgga    180
guacuucgag augagcgugc gccuggccga ggccaugaag cgguacgccc ugaacaccaa    240
ccaccggauc gugguguggcu cggagaacag ccugcaguuc uucaugccgg ugcugggcgc    300
ccucuucauc ggcguggccg ucgccccggc gaacgacauc uacaacgagc gggagcugcu    360
gaacagcaug gggaucagcc agccgaccgu ggiguuccgug agcaagaagg ccugcagaa    420
gauccugaac gugcagaaga agcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg gacaagacca ucgcccugau    600
caugaacagc agcggcagca ccggccgcc gaaggggggug gccccgccgc accgaccgc     660
cugcgugcgc uucucgcacg cccgggaccc caucuucggc aaccagauca ucccggacac    720
cgccauccug agcguggugc cguuccacca cggcuucggc auguucacga cccugggcua    780
ccucaucugc ggcuuccggg uguccugau guaccgguuc gaggaggagc uguuccugcg    840
gagccugcag gacuacaaga uccagagcgc gcucucgug ccgacccggu ucagcuucuu    900
cgccaagagc acccugaucg acaaguacga ccugucgaac cugcacgaga ucgccagcgg    960
gggcgccccg cugagcaagg aggugggcga ggccguggcc aagcgguucc accucccggg   1020
cauccgccag ggcuacggcc ugaccgagac cacgagcgcg auccugauca ccccgaggg    1080
ggacgacaag ccgggcgccg ugggcaaggu gguccccguuc uucgaggcca agguggugga  1140
```

| | |
|---|---:|
| ccuggacacc ggcaagaccc ugggcgugaa ccagcggggc gagcugugcg ugcggggggcc | 1200 |
| gaugaucaug agcggcuacg ugaacaaccc ggaggccacc aacgcccuca ucgacaagga | 1260 |
| cggcuggcug cacagcggcg acaucgccua cuggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag cacggcaaga ccaugacgga | 1500 |
| gaaggagauc gucgacuacg uggccagcca ggugaccacc gccaagaagc ugcggggcgg | 1560 |
| cguggugcuuc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgauggg ccucccaacg ggcccuccuc cccuccuugc accgagauua | 1740 |
| auaaaaaaaa aaaaaaaaaa aaaaaaaaaa aaaaaaaaaa aaaaaaaaaa aaaaaaaaaa | 1800 |
| aaaaaaugca ucaaaggcuc uuuucagagc cacca | 1835 |

<210> SEQ ID NO 47
<211> LENGTH: 1869
<212> TYPE: RNA
<213> ORGANISM: artificial
<220> FEATURE:
<223> OTHER INFORMATION: mRNA sequence of ppLuc(GC)-ag-A120

<400> SEQUENCE: 47

| | |
|---|---:|
| gggagaaagc uugaggaugg aggacgccaa gaacaucaag aagggcccgg cgcccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacgccc ugaacaccaa | 240 |
| ccaccggauc guggugugcu cggagaacag ccugcaguuc uucaugccgg ugcugggcgc | 300 |
| ccucuucauc ggcguggccg ugccccggc gaacgacauc uacaacgagc gggagcugcu | 360 |
| gaacagcaug gggaucagcc agccgaccgu ggnguucgug agcaagaagg ccugcagaa | 420 |
| gauccugaac gugcagaaga agcugcccau cauccgaag aucaucauca uggacagcaa | 480 |
| gaccgacuac cagggcuucc agucgaugua cacguucgug accagccacc ucccgccggg | 540 |
| cuucaacgag uacgacuucg ucccggagag cuucgaccgg acaagacca ucgcccugau | 600 |
| caugaacagc agcggcagca ccggccugcc gaagggggug gcccugccgc accggaccgc | 660 |
| cugcgugcgc uucucgcacg cccgggaccc caucuucggc aaccagauca ucccggacac | 720 |
| cgccauccug agcgugguc gguuccacca cggcuucggc auguucacga cccugggcua | 780 |
| ccucaucugc ggcuuccggg ugguccugau guaccgguuc gaggaggagc uguuccugcg | 840 |
| gagccugcag gacuacaaga uccagagcgc gcugcucgug ccgacccugu cagcuucuu | 900 |
| cgccaagagc acccugaucg acaaguacga ccugucgaac cugcacgaga ucgccagcgg | 960 |
| gggcgccccg cugagcaagg agggggcgga ggccguggcc aagcgguucc accucccggg | 1020 |
| cauccgccag ggcuacggcc ugaccgagac cacgagcgcg auccugauca ccccccgaggg | 1080 |
| ggacgacaag ccgggcgccg ugggcaaggu ggucccguuc uucgaggcca aggugguga | 1140 |
| ccuggacacc ggcaagaccc ugggcgugaa ccagcggggc gagcugugcg ugcggggggcc | 1200 |
| gaugaucaug agcggcuacg ugaacaaccc ggaggccacc aacgcccuca ucgacaagga | 1260 |
| cggcuggcug cacagcggcg acaucgccua cuggacgag gacgagcacu ucuucaucgu | 1320 |
| cgaccggcug aagucgcuga ucaaguacaa gggcuaccag guggcgccgg ccgagcugga | 1380 |

-continued

```
gagcauccug cuccagcacc ccaacaucuu cgacgccggc guggccgggc ugccggacga   1440
cgacgccggc gagcugccgg ccgcgguggu ggugcuggag cacggcaaga ccaugacgga   1500
gaaggagauc gucgacuacg uggccagcca ggugaccacc gccaagaagc ugcggggcgg   1560
cguggucuuc guggacgagg ucccgaaggg ccugaccggg aagcucgacg cccggaagau   1620
ccgcgagauc cugaucaagg ccaagaaggg cggcaagauc ccgguguaag acuaguuaua   1680
agacugacua gcccgauggg ccucccaacg ggcccuccuc cccuccuugc accgagauua   1740
auagaucuaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaa                                                           1869
```

<210> SEQ ID NO 48
<211> LENGTH: 1858
<212> TYPE: RNA
<213> ORGANISM: artificial
<220> FEATURE:
<223> OTHER INFORMATION: mRNA sequence of ppLuc(GC)-ag-A64-ag

<400> SEQUENCE: 48

```
gggagaaagc uugaggaugg aggacgccaa gaacaucaag aagggcccgg cgcccuucua     60
cccgcuggag gacgggaccg ccggcgagca gcuccacaag gccaugaagc gguacgcccu    120
ggugccgggc acgaucgccu ucaccgacgc ccacaucgag gucgacauca ccuacgcgga    180
guacuucgag augagcgugc gccuggccga ggccaugaag cgguacgccc ugaacaccaa    240
ccaccggauc guggugugcu cggagaacag ccugcaguuc uucaugccgg ugcugggcgc    300
ccucuucauc ggcguggccg ucgccccggc gaacgacauc uacaacgagc gggagcugcu    360
gaacagcaug gggaucagcc agccgaccgu ggucuucgug agcaagaagg ccugcagaa    420 gauccugaac gugcagaaga gcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg acaagacca ucgcccugau    600 caugaacagc agcggcagca ccggccugcc gaagggggug gccugccgc accgaccgc    660 cugcgugcgc uucucgcacg cccgggaccc caucuucggc aaccagauca ucccggacac    720
cgccauccug agcgugguge cguuccacca cggcuucggc auguucacga cccugggcua    780
ccucaucugc ggcuuccggg ugguccugau guaccgguuc gaggaggagc uguuccugcg    840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg agguggggcga ggccgguggcc aagcgguucc accucccggg   1020
cauccgccag ggcuacggcc ugaccgagac cacgagcgcg auccugauca ccccccgaggg   1080 ggacgacaag ccgggcgccg ugggcaaggu ggucccguuc uucgaggcca ggugguggga   1140
ccuggacacc ggcaagaccc ugggcgugaa ccagcggggc gagcugugcg ucgggggcc    1200 gaugaucaug agcggcuacg ugaacaaccc ggaggccacc aacgcccuca ucgacaagga   1260
cggcuggcug cacagcggcg acaucgccua cugggacgag gacgagcacu ucuucaucgu   1320
cgaccggcug aagucgcuga ucaaguacaa gggcuaccag guggcgccgg ccgagcugga   1380
gagcauccug cuccagcacc ccaacaucuu cgacgccggc guggccgggc ugccggacga   1440
cgacgccggc gagcugccgg ccgcgguggu ggugcuggag cacggcaaga ccaugacgga   1500
```

```
gaaggagauc gucgacuacg uggccagcca ggugaccacc gccaagaagc ugcggggcgg   1560 cguggucguuc guggacgagg ucccgaaggg ccugaccggg aagcucgacg cccggaagau   1620
```



```
gaaggagauc gucgacuacg uggccagcca ggugaccacc gccaagaagc ugcggggcgg   1560
cgugguguuc guggacgagg ucccgaaggg ccugaccggg aagcucgacg cccggaagau   1620
ccgcgagauc cugaucaagg ccaagaaggg cggcaagauc gccguguaag acuaguuaua   1680
agacugacua gcccgauggg ccucccaacg ggccuccuc cccuccuugc accgagauua   1740
auaaaaaaaa aaaaaaaaaa aaaaaaaaaa aaaaaaaaaa aaaaaaaaaa aaaaaaaaaa   1800
aaaaaaugca uccugcccga ugggccuccc aacgggcccu ccuccccucc uugcaccg    1858
```

<210> SEQ ID NO 49
<211> LENGTH: 1894
<212> TYPE: RNA
<213> ORGANISM: artificial
<220> FEATURE:
<223> OTHER INFORMATION: mRNA sequence of ppLuc(GC)-ag-A64-aCPSL

<400> SEQUENCE: 49

```
gggagaaagc uugaggaugg aggacgccaa gaacaucaag aagggcccgg cgcccuucua     60
cccgcuggag gacgggaccg ccggcagca gcuccacaag gccaugaagc gguacgcccu    120
ggugccgggc acgaucgccu ucaccgacgc ccacaucgag gucgacauca ccuacgcgga    180
guacuucgag augagcgugc gccuggccga ggccaugaag cgguacggcc ugaacaccaa    240
ccaccggauc guggugugcu cggagaacag ccugcaguuc uucaugccgg ugcugggcgc    300
ccucuucauc ggcguggccg ucgccccggc gaacgacauc uacaacgagc gggagcugcu    360
gaacagcaug gggaucagcc agccgaccgu ggucuucgug agcaagaagg gccugcagaa    420
gauccugaac gugcagaaga agcugcccau cauccgaaag aucaucauca uggacagcaa    480
gaccgacuac cagggcuucc agucgaugua cacguucgug accagccacc ucccgccggg    540
cuucaacgag uacgacuucg ucccggagag cuucgaccgg gacaagacca ucgcccugau    600
cauggacagc agcggcagca ccggccugcc gaaggggggug gcccugccgc accggaccgc    660
cugcgugcgc uucucgcacg cccgggaccc caucuucggc aaccagauca ucccggacac    720
cgccauccug agcguggugc cguuccacca cggcuucggc auguucacga cccugggcua    780
ccucaucugc ggcuuccggg uggcccugau guaccgguuc gaggaggagc uguuccugcg    840
gagccugcag gacuacaaga uccagagcgc gcugcucgug ccgacccugu ucagcuucuu    900
cgccaagagc acccgaucg acaaguacga ccugucgaac cugcacgaga ucgccagcgg    960
gggcgccccg cugagcaagg aggugggcga ggccguggcc aagcgguucc accucccggg   1020
cauccgccag ggcuacggcc ugaccgagac cacgagcgcg auccugauca cccccgaggg   1080
ggacgacaag ccgggcgccg ugggcaaggu ggucccguuc uucgaggcca ggugguugga   1140
ccuggacacc ggcaagaccc ugggcgugaa ccagcggggc gagcugugcg ugcggggcc   1200 gaugaucaug agcggcuacg ugaacaaccc ggaggccacc aacgcccuca ucgacaagga   1260
cggcuggcug cacagcggcg acaucgccua cugggacgag gacgagcacu ucuucaucgu   1320
cgaccggcug aagucgcuga ucaaguacaa gggcuaccag guggcgccgg ccgagcugga   1380
gagcauccug cuccagcacc ccaacaucuu cgacgccggc guggccgggc ugccggacga   1440
cgacgccggc gagcugccgg ccgcggugu ggugcuggag cacggcaaga ccaugacgga   1500
gaaggagauc gucgacuacg uggccagcca ggugaccacc gccaagaagc ugcggggcgg   1560
cgugguguuc guggacgagg ucccgaaggg ccugaccggg aagcucgacg cccggaagau   1620
ccgcgagauc cugaucaagg ccaagaaggg cggcaagauc gccguguaag acuaguuaua   1680
agacugacua gcccgauggg ccucccaacg ggccuccuc cccuccuugc accgagauua   1740
```

```
auaaaaaaaa aaaaaaaaaa aaaaaaaaaa aaaaaaaaaa aaaaaaaaaa aaaaaaaaaa    1800
aaaaaaugca ucaauuccua cacgugaggc gcugugauuc ccuauccccc uucauucccu    1860
auacauuagc acagcgccau ugcauguagg aauu                                1894
```

```
<210> SEQ ID NO 50
<211> LENGTH: 1909
<212> TYPE: RNA
<213> ORGANISM: artificial
<220> FEATURE:
<223> OTHER INFORMATION: mRNA sequence of ppLuc(GC)-ag-A64-PolioCL

<400> SEQUENCE: 50
```

```
gggagaaagc uugaggaugg aggacgccaa gaacaucaag aagggcccgg cgcccuucua      60
cccgcuggag gacgggaccg ccggcgagca gcuccacaag gccaugaagc gguacgcccu     120
ggugccgggc acgaucgccu ucaccgacgc ccacaucgag gucgacauca ccuacgcgga     180
guacuucgag augagcgugc gccuggccga ggccaugaag cgguacggcc ugaacaccaa     240
ccaccggauc guggugugcu cggagaacag ccugcaguuc uucaugccgg ugcugggcgc     300
ccucuucauc ggcguggccg ucgccccggc gaacgacauc uacaacgagc gggagcugcu     360
gaacagcaug gggaucagcc agccgaccgu ggucuucgug agcaagaagg ccugcagaa     420 gauccugaac gugcagaaga gcugcccau cauccgaag aucaucauca uggacagcaa     480
gaccgacuac cagggcuucc agucgaugua cacguucgug accagccacc ucccgccggg     540
cuucaacgag uacgacuucg ucccggagag cuucgaccgg acaagacca ucgcccugau     600 caugaacagc agcggcagca ccggccugcc gaaggggggug gcccugccgc accggaccgc     660
cugcgugcgc uucucgcacg cccgggaccc caucuucggc aaccagauca ucccggacac     720
cgccauccug agcguggugc cguuccacca cggcuucggc auguucacga cccugggcua     780
ccucaucugc ggcuuccggg uggucccgau guaccggguc gaggaggagc uguuccugcg     840
gagccugcag gacuacaaga uccagagcgc gcugcucgug ccgacccugu ucagcuucuu     900
cgccaagagc acccugaucg acaaguacga ccugucgaac cugcacgaga ucgccagcgg     960
gggcgccccg cugagcaagg agguggggcga ggccguggcc aagcgguucc accucccggg    1020
cauccgccag ggcuacggcc ugaccgagac cacgagcgcg auccugauca ccccgagggg    1080
ggacgacaag ccgggcgccg ugggcaaggu gguccccguuc uucgagggcca aggugguga    1140 ccuggacacc ggcaagaccc ugggcguga ccagcggggc gagcugugcg ugcggggcc    1200 gauaucaug agcggcuacg ugaacaaccc ggaggccacc aacgcccuca ucgacaagga    1260
cggcuggcug cacagcggcg acaucgccua cugggacgag gacgagcacu ucuucaucgu    1320
cgaccggcug aagucgcuga ucaaguacaa gggcuaccag guggcgccgg ccgagcugga    1380
gagcauccug cuccagcacc ccaacaucuu cgacgccggc guggccgggc ugccggacga    1440
cgacgccggc gagcugccgg ccgcgguggu ggugcuggag cacggcaaga ccaugacgga    1500
gaaggagauc gucgacuacg uggccagcca ggugaccacc gccaagaagc ugcggggcgg    1560
cgugguguuc guggacgagg ucccgaaggg ccugaccggg aagcucgacg cccggaagau    1620
ccgcgagauc cugaucaagg ccaagaaggg cggcaagauc gccguguaag acuaguuaua    1680
agacugacua gcccgauggg ccucccaacg ggcccuccuc cccuccuugc accgagauua    1740
auaaaaaaaa aaaaaaaaaa aaaaaaaaaa aaaaaaaaaa aaaaaaaaaa aaaaaaaaaa    1800
aaaaaaugca ucaauucuaa aacagcucug ggguuguacc cacccagag gcccacgugg    1860
```

```
cggcuaguac uccgguauug cgguacccuu guacgccugu uuuagaauu        1909
```

<210> SEQ ID NO 51
<211> LENGTH: 1841
<212> TYPE: RNA
<213> ORGANISM: artificial
<220> FEATURE:
<223> OTHER INFORMATION: mRNA sequence of ppLuc(GC)-ag-A64-G30

<400> SEQUENCE: 51

```
gggagaaagc uugaggaugg aggacgccaa gaacaucaag aagggcccgg cgcccuucua      60
cccgcuggag gacgggaccg ccggcgagca gcuccacaag gccaugaagc gguacgcccu     120
ggugccgggc acgaucgccu ucaccgacgc ccacaucgag gucgacauca ccuacgcgga     180
guacuucgag augagcgugc gccuggccga ggccaugaag cgguacggcc ugaacaccaa     240
ccaccggauc guggugugcu cggagaacag ccugcaguuc uucaugccgg ugcugggcgc     300
ccucuucauc ggcguggccg ucgccccggc gaacgacauc uacaacgagc gggagcugcu     360
gaacagcaug gggaucagcc agccgaccgu ggugucgug agcaagaagg gccugcagaa     420
gauccugaac gugcagaaga agcugcccau caucagaag ucaucauca uggacagcaa     480
gaccgacuac cagggcuucc agucgaugua cacguucgug accagccacc ucccgccggg     540
cuucaacgag uacgacuucg ucccggagag cuucgaccgg gacaagacca ucgcccugau     600
caugaacagc agcggcagca ccggccugcc gaagggggug gcccgccgc accgaccgc     660
cugcgugcgc uucucgcacg cccgggaccc caucuucggc aaccagauca ucccggacac     720
cgccauccug agcguggugc cguuccacca cggcuucggc auguucacga cccugggcua     780
ccucaucugc ggcuuccggg ugguccugau guaccgguuc gaggaggagc uguuccugcg     840
gagccugcag gacuacaaga uccagagcgc gcugcucgug ccgacccugu ucagcuucuu     900
cgccaagagc acccugaucg acaaguacga ccugucgaac cugcacgaga ucgccagcgg     960
gggcgccccg cugagcaagg agugggcga ggccgguggcc aagcgguucc accucccggg    1020
cauccgccag ggcuacggcc ugaccgagac cacgagcgcg auccugauca ccccccgaggg    1080
ggacgacaag ccgggcgccg ugggcaaggu gguccguuc uucgaggcca agguggugga    1140
ccuggacacc ggcaagaccc ugggcgugaa ccagcggggc gagcugugcg ugcggggcc    1200
gaugaucaug agcggcuacg ugaacaaccc ggaggccacc aacgcccuca ucgacaagga    1260
cggcuggcug cacagcggcg acaucgccua cugggacgag gacgagcacu ucuucaucgu    1320
cgaccggcug aagucgcuga ucaaguacaa gggcuaccag guggcgccgg ccgagcugga    1380
gagcauccug cuccagcacc caacaucuu cgacgccggc guggccgggc ugccggacga    1440
cgacgccggc gagcugccgg ccgcgguggu ggugcuggag cacggcaaga ccaugacgga    1500
gaaggagauc gucgacuacg uggccagcca ggugaccacc gccaagaagc ugcggggcgg    1560
cguggguuuc guggacgagg ucccgaaggg ccugaccggg aagcucgacg cccggaagau    1620
ccgcgagauc cugaucaagg ccaagaaggg cggcaagauc gccguguaag acuaguuaua    1680
agacugacua gcccgauggg ccucccaacg ggcccuccuc cccuccuugc accgagauua    1740
auaaaaaaaa aaaaaaaaaa aaaaaaaaaa aaaaaaaaaa aaaaaaaaaa aaaaaaaaaa    1800
aaaaaaugca ugggggggggg gggggggggg gggggggggg g                       1841
```

<210> SEQ ID NO 52
<211> LENGTH: 1841
<212> TYPE: RNA
<213> ORGANISM: artificial

```
<220> FEATURE:
<223> OTHER INFORMATION: mRNA sequence of ppLuc(GC)-ag-A64-U30

<400> SEQUENCE: 52
gggagaaagc uugaggaugg aggacgccaa gaacaucaag aagggcccgg cgcccuucua      60
cccgcuggag gacgggaccg ccggcgagca gcuccacaag gccaugaagc gguacgcccu     120
ggugccgggc acgaucgccu ucaccgacgc ccacaucgag gucgacauca ccuacgcgga     180
guacuucgag augagcgugc gccuggccga ggccaugaag cgguacgcc ugaacaccaa      240
ccaccggauc guggugugcu cggagaacag ccugcaguuc uucaugccgg ugcugggcgc     300
ccucuucauc ggcguggccg ucgccccggc gaacgacauc uacaacgagc gggagcugcu     360
gaacagcaug gggaucagcc agccgaccgu gguguucgug agcaagaagg ccugcagaa      420
gauccugaac gugcagaaga gcugcccau cauccagaag aucaucauca uggacagcaa      480
gaccgacuac cagggcuucc agucgaugua cacguucgug accagccacc ucccgccggg     540
cuucaacgag uacgacuucg ucccggagag cuucgaccgg gacaagacca ucgcccugau     600
caugaacagc agcggcagca ccggccugcc gaaggggug gcccugccgc accggaccgc      660
cugcgugcgc uucucgcacg cccgggaccc caucuucggc aaccagauca ucccggacac     720
cgccauccug agcguggugc cguuccacca cggcuucggc auguucacga cccugggcua     780
ccucaucugc ggcuuccggg ugguccugau guaccggguu cgaggaggag cuuccugcg     840
gagccugcag gacuacaaga uccagagcgc gcugcucgug ccgacccugu ucagcuucuu     900
cgccaagagc acccugaucg acaaguacga ccugucgaac cugcacgaga ucgccagcgg     960
gggcgccccg cugagcaagg aggugggcga ggccguggcc aagcgguucc accuccgggg    1020
cauccgccag ggcuacggcc ugaccgagac cacgagcgcg auccugauca cccccgaggg    1080
ggacgacaag ccgggcgccg ugggcaaggu ggucccguuc uucgaggcca gguggugga    1140
ccuggacacc ggcaagaccc ugggcgugaa ccagcggggc gagcugugcg ugcggggcc     1200
gaugaucaug agcggcuacg ugaacaaccc ggaggccacc aacgcccuca ucgacaagga    1260
cggcuggcug cacagcggcg acaucgccua cugggacgag gacgagcacu ucuucaucgu    1320
cgaccggcug aagucgcuga ucaaguacaa gggcuaccag gugcgccgg ccgagcugga    1380
gagcauccug cuccagcacc ccaacaucuu cgacgccggc guggccgggc ugccggacga    1440
cgacgccggc gagcugccgg ccgcggugg gugcuggag cacggcaaga ccaugacgga    1500
gaaggagauc gucgacuacg uggccagcca ggugaccacc gccaagaagc ugcggggcgg    1560
cguggguuuc guggacgagg ucccgaaggg ccugaccggg aagcucgacg cccggaagau    1620
ccgcgagauc cugaucaagg ccaagaaggg cggcaagauc gccguguaag acuaguuaua    1680
agacugacua gcccgaugggg ccucccaacg ggccuccuc cccuccuugc accgagauua    1740
auaaaaaaaa aaaaaaaaaa aaaaaaaaaa aaaaaaaaaa aaaaaaaaaa aaaaaaaaaa    1800
aaaaaaugca uuuuuuuuuu uuuuuuuuuu uuuuuuuuuu u                        1841

<210> SEQ ID NO 53
<211> LENGTH: 1857
<212> TYPE: RNA
<213> ORGANISM: artificial
<220> FEATURE:
<223> OTHER INFORMATION: mRNA sequence of ppLuc(GC)-ag-A64-SL

<400> SEQUENCE: 53
gggagaaagc uugaggaugg aggacgccaa gaacaucaag aagggcccgg cgcccuucua      60
```

| | |
|---|---|
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacggcc ugaacaccaa | 240 |
| ccaccggauc guggugugcu cggagaacag ccugcaguuc uucaugccgg ugcugggcgc | 300 |
| ccucuucauc ggcguggccg ucgccccggc gaacgacauc uacaacgagc gggagcugcu | 360 |
| gaacagcaug gggaucagcc agccgaccgu gguguucgug agcaagaagg gccugcagaa | 420 |
| gauccugaac gugcagaaga gcugcccau cauccagaag aucaucauca uggacagcaa | 480 |
| gaccgacuac cagggcuucc agucgaugua cacguucgug accagccacc ucccgccggg | 540 |
| cuucaacgag uacgacuucg ucccggagag cuucgaccgg acaagacca ucgcccugau | 600 |
| caugaacagc agcggcagca ccggccugcc gaagggggug gcccugccgc accgaccgc | 660 |
| cugcgugcgc uucucgcacg cccgggaccc caucuucggc aaccagauca ucccggacac | 720 |
| cgccauccug agcguggugc cguuccacca cggcuucggc auguuacga cccugggcua | 780 |
| ccucaucugc ggcuuccggg ugguccugau guaccgguuc gaggaggagc uguuccugcg | 840 |
| gagccugcag gacuacaaga uccagagcgc gcugcucgug ccgacccugu ucagcuucuu | 900 |
| cgccaagagc acccugaucg acaaguacga ccugucgaac cugcacgaga ucgccagcgg | 960 |
| gggcgccccg cugagcaagg aggugggcga ggccguggcc aagcgguucc accucccggg | 1020 |
| cauccgccag ggcuacggcc ugaccgagac cacgagcgcg auccgaucga cccccgaggg | 1080 |
| ggacgacaag ccgggcgccg ugggcaaggu ggucccguuc uucgaggcca aggugguga | 1140 |
| ccuggacacc ggcaagaccc uggcgcgaa ccagcggggc gagcugugcg ugcgggggcc | 1200 |
| gaugaucaug agcggcuacg ugaacaaccc ggaggccacc aacgcccuca ucgacaagga | 1260 |
| cggcuggcuc cacagcggcg acaucgccua cugggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcgguggu ggugcuggag cacggcaaga ccaugacgga | 1500 |
| gaaggagauc gucgacuacg uggccagcca ggugaccacc gccaagaagc ugcggggcgg | 1560 |
| cguggugụuc guggacgagg ucccgaaggg ccugaccggg aagcucgacg cccggaagau | 1620 |
| ccgcgagauc cugaucaagg ccaagaaggg cggcaagauc gccguguaag acuaguuaua | 1680 |
| agacugacua gcccgauggg ccucccaacg ggccccccuc cccuccuugc accgagauua | 1740 |
| auaaaaaaaa aaaaaaaaaa aaaaaaaaaa aaaaaaaaaa aaaaaaaaaa aaaaaaaaaa | 1800 |
| aaaaaaugca uuauggcggc cgugccacc acggauauca ccgugguggaCgcggcc | 1857 |

<210> SEQ ID NO 54
<211> LENGTH: 1838
<212> TYPE: RNA
<213> ORGANISM: artificial
<220> FEATURE:
<223> OTHER INFORMATION: ppLuc(GC)-ag-A64-N32

<400> SEQUENCE: 54

| | |
|---|---|
| gggagaaagc uugaggaugg aggacgccaa gaacaucaag aagggcccgg cgcccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacggcc ugaacaccaa | 240 |
| ccaccggauc guggugugcu cggagaacag ccugcaguuc uucaugccgg ugcugggcgc | 300 |

-continued

```
ccucuucauc ggcguggccg ucgccccggc gaacgacauc uacaacgagc gggagcugcu    360
gaacagcaug gggaucagcc agccgaccgu ggguuucgug agcaagaagg gccugcagaa    420
gauccugaac gugcagaaga agcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg gacaagacca ucgcccugau    600
caugaacagc agcggcagca ccggccugcc gaaggggugu gcccugccgc accgaccgc     660 cugcgugcgc uucucgcacg cccgggaccc caucuucggc aaccagauca ucccggacac    720
cgccauccug agcguggugc cguuccacca cggcuucggc auguucacga cccugggcua    780
ccucaucugc ggcuuccggg ugguccugau guaccgguuc gaggaggagc uguuccugcg    840
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg aggugggcga ggccgguggcc aagcgguucc accucccggg   1020
cauccgccag ggcuacggcc ugaccgagac cacgagcgcg auccugauca cccccgaggg    1080
ggacgacaag ccgggcgccg ugggcaaggu ggucccguuc uucgaggcca aggugguuga    1140
ccuggacacc ggcaagaccc ugggcgugaa ccagcggggc gagcugugcg ucgggggcc     1200 gaugaucaug agcggcuacg ugaacaaccc ggaggccacc aacgcccuca ucgacaagga    1260
cggcuggcug cacagcggcg acaucgccua cuggacgag gacgagcacu ucuucaucgu     1320
cgaccggcug aagucgcuga ucaaguacaa gggcuaccag guggcgccgg ccgagcugga    1380
gagcauccug cuccagcacc ccaacaucuu cgacgccggc guggccgggc ugccggacga    1440
cgacgccggc gagcugccgg ccgcgguggu ggugcuggag cacggcaaga ccaugacgga    1500
gaaggagauc gucgacuacg uggccagcca ggugaccacc gccaagaagc ugcggggcgg    1560
cguggugaac guggacgagg ucccgaaggg ccugaccggg aagcucgacg cccggaagau    1620
ccgcgagauc cugaucaagg ccaagaaggg cggcaagauc gccguguaag acuaguuaua    1680
agacugacua gcccgauggg ccucccaacg ggcccuccuc cccuccuugc accgagauua    1740
auaaaaaaaa aaaaaaaaaa aaaaaaaaaa aaaaaaaaaa aaaaaaaaaa aaaaaaaaaa    1800
aaaaaaugca uccccucua gacaauugga auuccaua                             1838
```

<210> SEQ ID NO 55
<211> LENGTH: 1902
<212> TYPE: RNA
<213> ORGANISM: artificial
<220> FEATURE:
<223> OTHER INFORMATION: mRNA sequence of HA (H1N1/PR8) (GC)-ag-A64-C30

<400> SEQUENCE: 55

```
gggagaaagc uuaccaugaa ggccaaccug cucgugcugc ugugcgcccu cgcggccgcc    60
gacgccgaca ccaucugcau cggcuaccac gccaacaaca gcaccgacac ggucgacacc    120
gugcuggaga agaacgugac cgucacccac uccgugaacc ugcucgagga cagccacaac    180
gggaagcugu gccggcugaa gggcaucgcg cccucccagc uggggaagug caacaucgcc    240
ggcuggcugc ucgggaaccc ggagugcgac ccccugcucc ccgugcgcuc cuggagcuac    300
aucgucgaga cgcccaacuc cgagaacggc aucugcuacc cgggcgacuu caucgacuac    360
gaggagcucc gggagcagcu gagcuccgug agcuccuucg agcgcuucga gaucuucccc    420
aaggagagcu ccuggcccaa ccacaacacc aacgggguga ccgccgccug cagccacgag    480
```

-continued

| | |
|---|---|
| ggcaagucca gcuucuaccg gaaccugcuc uggcugaccg agaaggaggg guccuacccc | 540 |
| aagcugaaga acagcuacgu caacaagaag ggcaaggagg ugcucgugcu guggggggauc | 600 |
| caccacccgc ccaacuccaa ggagcagcag aaccuguacc agaacgagaa cgcguacguc | 660 |
| agcgugguga cguccaacua caaccgccgg uucacccccg agaucgccga gcgccccaag | 720 |
| guccgggacc aggccggccg caugaacuac uacuggaccc uccugaagcc gggcgacacc | 780 |
| aucaucuucg aggccaacgg gaaccugauc gccccgaugu acgcguucgc ccucagccgg | 840 |
| ggcuucggga gcggcaucau cacguccaac gccagcaugc acgagugcaa caccaagugc | 900 |
| cagacccccc ugggcgccau caacuccagc cugcccuacc agaacaucca cccсggugacc | 960 |
| aucggggagu gccccaagua cgugcgcucc gccaagcucc ggauggucac gggccugcgc | 1020 |
| aacaacccca gcauccaguc ccggggggcug uucggcgcga ucgccgдgguu caucgagggc | 1080 |
| ggcuggaccg ggaugaucga cggcugguac ggguaccacc accagaacga gcagggcagc | 1140 |
| ggguacgccg ccgaccagaa guccacccag aacgccauca acggcaucac caacaagguG | 1200 |
| aacacgguga ucgagaagau gaacauccag uucaccgcgg ucggcaagga guucaacaag | 1260 |
| cucgagaagc gcauggagaa ccugaacaag aagguggacg acgggguuccu ggacaucugg | 1320 |
| accuacaacg ccgagcuccu ggugcugcuc gagaacgagc ggacccugga cuuccacgac | 1380 |
| agcaacguca agaaccugua cgagaagguG aagucccagc ucaagaacaa cgccaaggag | 1440 |
| aucggcaacg ggugcuucga guucuaccac aagugcgaca cgagugcau ggagagcguc | 1500 |
| cgcaacggca cguacgacua ccccaaguac uccgaggaga gcaagcugaa ccgggagaag | 1560 |
| guggacgggg ugaagcugga guccauggGc aucuaccaga uccucgccau cuacагсасс | 1620 |
| gucgccucca gccuggugcu gcuggugucc cucggcgcga ucagcuucug gaugugcagc | 1680 |
| aacggguccc ugcagugccg caucugcauc ugaccacuag uuauaagacu gacuagcccg | 1740 |
| augggccucc caacgggccc uccuccccuc cuugcaccga gauuaauaaa aaaaaaaaaa | 1800 |
| aaaaaaaaaa aaaaaaaaaa aaaaaaaaaa aaaaaaaaaa aaaaaaaaaa auauuccccc | 1860 |
| cccccccccc cccccccccc ccccccucuag acaauuggaa uu | 1902 |

<210> SEQ ID NO 56
<211> LENGTH: 1915
<212> TYPE: RNA
<213> ORGANISM: artificial
<220> FEATURE:
<223> OTHER INFORMATION: mRNA sequence of HA (H1N1/PR8) (GC)-ag-A64-C30-histoneSL

<400> SEQUENCE: 56

| | |
|---|---|
| gggagaaagc uuaccaugaa ggccaaccug cucgugcugc ugugcgcccu cgcggccgcc | 60 |
| gacgccgaca ccaucugcau cggcuaccac gccaacaaca gcaccgacac ggucgacacc | 120 |
| gugcuggaga agaacgugac cgucacccac uccgugaacc ugcucgagga cagccacaac | 180 |
| gggaagcugu gccggcugaa gggcaucgcg ccccuccagc uggggaagug caacaucgcc | 240 |
| ggcuggcugc ucgggaaccc ggagugcgac ccccugcugc ccgugcgcuc cuggagcuac | 300 |
| aucgucgaga cgcccaacuc cgagaacggc aucugcuacc cggcgacuu caucgacuac | 360 |
| gaggagcucc gggagcagcu gagcuccgug agccccuucg agcgcuucga gaucuucccc | 420 |
| aaggagagcu ccuggcccaa ccacaacacc aacggguga ccgccgccug cagccacgag | 480 |
| ggcaagucca gcuucuaccg gaaccugcuc uggcugaccg agaaggaggg guccuacccc | 540 |
| aagcugaaga acagcuacgu caacaagaag ggcaaggagg ugcucgugcu guggggggauc | 600 |

```
caccacccgc ccaacuccaa ggagcagcag aaccuguacc agaacgagaa cgcguacguc    660
agcgugguga cguccaacua caaccgccgg uucaccccg  agaucgccga gcgcccaag     720 guccgggacc aggccggccg caugaacuac uacuggaccc uccugaagcc gggcgacacc    780
aucaucuucg aggccaacgg gaaccugauc gccccgaugu acgcguucgc ccucagccgg    840
ggcuucggga gcggcaucau cacguccaac gccagcaugc acgagugcaa caccaagugc    900 cagaccccc  ugggcgccau caacuccagc cugcccuacc agaacaucca cccggugacc    960
aucggggagu gccccaagua cgugcgcucc gccaagcucc ggauggucac gggccugcgc   1020
aacaacccca gcauccaguc ccggggcug  uucggcgcga ucgccggguu caucgagggc   1080
ggcuggaccg ggaugaucga cggcugguac ggguaccacc accagaacga gcagggcagc   1140
ggguacgccg ccgaccagaa guccacccag aacgccauca acggcaucac caacaaggug   1200
aacacgguga ucgagaagau gaacauccag uucaccgcgg ucggcaagga guucaacaag   1260
cucgagaagc gcauggagaa ccugaacaag aagguggacg acggguuccu ggacaucugg   1320
accuacaacg ccgagcuccu ggugcugcuc gagaacgagc ggacccugga cuuccacgac   1380
agcaacguca agaaccugua cgagaaggug aaguccagc  ucaagaacaa cgccaaggag   1440
aucggcaacg ggugcuucga guucuaccac aagugcgaca cgagugcau  ggagagcguc   1500 cgcaacggca cguacgacua ccccaaguac uccgaggaga gcaagcugaa ccgggagaag   1560
guggacgggu ugaagcugga guccauggc  aucuaccaga uccucgccau cuacagcacc   1620
gucgccucca gccuggugcu gcuggugucc cucggcgcga ucagcuucug gaugugcagc   1680 aacgggucc  ugcagugccg caucugcauc ugaccacuag uuauaagacu gacuagcccg   1740
augggccucc caacgggccc uccuccccuc cuugcaccga gauuaauaaa aaaaaaaaa    1800 aaaaaaaaa  aaaaaaaaaa aaaaaaaaaa aaaaaaaaa  aaaaaaaaaa augcaucccc   1860 ccccccccc  cccccccccc cccccccaaa ggcucuuuuc agagccacca gaauu         1915

<210> SEQ ID NO 57
<211> LENGTH: 10
<212> TYPE: RNA
<213> ORGANISM: Artificial Sequence
<220> FEATURE:
<223> OTHER INFORMATION: Stem1 sequence

<400> SEQUENCE: 57
accuuucucc                                                           10

<210> SEQ ID NO 58
<211> LENGTH: 11
<212> TYPE: RNA
<213> ORGANISM: Artificial Sequence
<220> FEATURE:
<223> OTHER INFORMATION: Stem2 sequence

<400> SEQUENCE: 58
uggagaaagg u                                                         11
```

NUCLEIC ACID COMPRISING OR CODING FOR A HISTONE STEM-LOOP AND A POLY(A) SEQUENCE OR A POLYADENYLATION SIGNAL FOR INCREASING THE EXPRESSION OF AN ENCODED PATHOGENIC ANTIGEN

This application is a divisional of U.S. Application Ser. No. 16/938,136, filed Jul. 24, 2020, now U.S. Pat. No. 10,912,826, which is a continuation of U.S. application Ser. No. 15/892,330, filed Feb. 8, 2018, now U.S. Pat. No. 10,799,577, which is a continuation of U.S. application Ser. No. 15/465,322, filed Mar. 21, 2017, now U.S. Pat. No. 10,166,283, which is a continuation of U.S. application Ser. No. 14/378,538, filed Dec. 8, 2014, now U.S. Pat. No. 9,669,089, which is a national phase application under 35 U.S.C. § 371 of International Application No. PCT/EP2013/000460, filed Feb. 15, 2013, which is a continuation of International Application No. PCT/EP2012/000673, filed Feb. 15, 2012. The entire text of each of the above referenced disclosures is specifically incorporated herein by reference.

The present invention relates to a nucleic acid sequence, comprising or coding for a coding region, encoding at least one peptide or protein comprising a pathogenic antigen or a fragment, variant or derivative thereof, at least one histone stem-loop and a poly(A) sequence or a polyadenylation signal. Furthermore the present invention provides the use of the nucleic acid for increasing the expression of said encoded peptide or protein. It also discloses its use for the preparation of a pharmaceutical composition, especially a vaccine, e.g. for use in the treatment of infectious diseases. The present invention further describes a method for increasing the expression of a peptide or protein comprising a pathogenic antigen or a fragment, variant or derivative thereof, using the nucleic acid comprising or coding for a histone stem-loop and a poly(A) sequence or a polyadenylation signal.

Augmenting adaptive immunity by vaccination aims to promote effective responses against specific antigens present in pathogens in vivo. Traditional vaccination methods, using live attenuated or heat-killed pathogens, have been successful in preventing and treating infectious diseases such as smallpox, polio and diphtheria, but there are major diseases where no effective vaccine is available (e.g. malaria and HIV), or the available vaccine only gives transient or partial protection (e.g. cholera and flu). Newer strategies are aimed at targeting selected antigens to antigen presenting cell subsets and directing the immune system towards the Th1 and/or Th2 type immune responses associated with protection against the specific pathogen. These narrowly aimed strategies may also lead to the development of therapeutic vaccines able to overcome some of the immune deficiencies induced by pathogens for immune evasion (Gamvrellis, A., D. Leong et al. (2004), Immunology and Cell Biology 82, 506-516). One of these new strategies is genetic vaccination.

Gene therapy and genetic vaccination are methods of molecular medicine which already have been proven in the therapy and prevention of diseases and generally exhibit a considerable effect on daily medical practice, in particular on the treatment of diseases as mentioned above. Both methods, gene therapy and genetic vaccination, are based on the introduction of nucleic acids into the patient's cells or tissue and subsequent processing of the information coded for by the nucleic acid that has been introduced into the cells or tissue, that is to say the (protein) expression of the desired polypeptides.

In gene therapy approaches, typically DNA is used even though RNA is also known in recent developments. Importantly, in all these gene therapy approaches mRNA functions as messenger for the sequence information of the encoded protein, irrespectively if DNA, viral RNA or mRNA is used.

In general RNA is considered an unstable molecule: RNases are ubiquitous and notoriously difficult to inactivate. Furthermore, RNA is also chemically more labile than DNA. Thus, it is perhaps surprising that the "default state" of an mRNA in a eukaryotic cell is characterized by a relative stability and specific signals are required to accelerate the decay of individual mRNAs. The main reason for this finding appears to be that mRNA decay within cells is catalyzed almost exclusively by exonucleases. However, the ends of eukaryotic mRNAs are protected against these enzymes by specific terminal structures and their associated proteins: a m7GpppN CAP at the 5' end and typically a poly(A) sequence at the 3' end. Removal of these two terminal modifications is thus considered rate limiting for mRNA decay. Although a stabilizing element has been characterized in the 3' UTR of the alpha-globin mRNA, RNA sequences affecting turnover of eukaryotic mRNAs typically act as a promoter of decay usually by accelerating deadenylation (reviewed in Meyer, S., C. Temme, et al. (2004), Crit Rev Biochem Mol Biol 39(4): 197-216).

As mentioned above, the 5' ends of eukaryotic mRNAs are typically modified post transcriptionally to carry a methylated CAP structure, e.g. m7GpppN. Aside from roles in RNA splicing, stabilization, and transport, the CAP structure significantly enhances the recruitment of the 40S ribosomal subunit to the 5' end of the mRNA during translation initiation. The latter function requires recognition of the CAP structure by the eukaryotic initiation factor complex eIF4F. The poly(A) sequence additionally stimulates translation via increased 40S subunit recruitment to mRNAs, an effect that requires the intervention of poly(A) binding protein (PABP). PABP, in turn, was recently demonstrated to interact physically with eIF4G, which is part of the CAP-bound eIF4F complex. Thus, a closed loop model of translation initiation on capped, polyadenylated mRNAs was postulated (Michel, Y. M., D. Poncet, et al. (2000), J Biol Chem 275(41): 32268-76).

Nearly all eukaryotic mRNAs end with such a poly(A) sequence that is added to their 3' end by the ubiquitous cleavage/polyadenylation machinery. The presence of a poly (A) sequence at the 3' end is one of the most recognizable features of eukaryotic mRNAs. After cleavage, most pre-mRNAs, with the exception of replication-dependent histone transcripts, acquire a polyadenylated tail. In this context, 3' end processing is a nuclear co-transcriptional process that promotes transport of mRNAs from the nucleus to the cytoplasm and affects the stability and the translation of mRNAs. Formation of this 3' end occurs in a two step reaction directed by the cleavage/polyadenylation machinery and depends on the presence of two sequence elements in mRNA precursors (pre-mRNAs); a highly conserved hexanucleotide AAUAAA (polyadenylation signal) and a downstream G/U-rich sequence. In a first step, pre-mRNAs are cleaved between these two elements. In a second step tightly coupled to the first step the newly formed 3' end is extended by addition of a poly(A) sequence consisting of 200-250 adenylates which affects subsequently all aspects of mRNA metabolism, including mRNA export, stability and translation (Dominski, Z. and W. F. Marzluff (2007), Gene 396(2): 373-90).

The only known exception to this rule are the replication-dependent histone mRNAs which end with a histone stem-loop instead of a poly(A) sequence. Exemplary histone stem-loop sequences are described in López et al. (Dávila López, M., & Samuelsson, T. (2008), RNA (New York, N.Y.), 14(1), 1-10. doi:10.1261/rna.782308).

The stem-loops in histone pre-mRNAs are typically followed by a purine-rich sequence known as the histone downstream element (HDE). These pre-mRNAs are processed in the nucleus by a single endonucleolytic cleavage approximately 5 nucleotides downstream of the stem-loop, catalyzed by the U7 snRNP through base pairing of the U7 snRNA with the HDE. The 3'-UTR sequence comprising the histone stem-loop structure and the histone downstream element (HDE) (binding site of the U7 snRNP) were usually termed as histone 3'-processing signal (see e.g. Chodchoy, N., N. B. Pandey, et al. (1991). Mol Cell Biol 11(1): 497-509).

Due to the requirement to package newly synthesized DNA into chromatin, histone synthesis is regulated in concert with the cell cycle. Increased synthesis of histone proteins during S phase is achieved by transcriptional activation of histone genes as well as posttranscriptional regulation of histone mRNA levels. It could be shown that the histone stem-loop is essential for all posttranscriptional steps of histone expression regulation. It is necessary for efficient processing, export of the mRNA into the cytoplasm, loading onto polyribosomes, and regulation of mRNA stability.

In the above context, a 32 kDa protein was identified, which is associated with the histone stem-loop at the 3'-end of the histone messages in both the nucleus and the cytoplasm. The expression level of this stem-loop binding protein (SLBP) is cell-cycle regulated and is highest during S-phase when histone mRNA levels are increased. SLBP is necessary for efficient 3'-end processing of histone pre-mRNA by the U7 snRNP. After completion of processing, SLBP remains associated with the stem-loop at the end of mature histone mRNAs and stimulates their translation into histone proteins in the cytoplasm. (Dominski, Z. and W. F. Marzluff (2007), Gene 396(2): 373-90). Interestingly, the RNA binding domain of SLBP is conserved throughout metazoa and protozoa (Dávila López, M., & Samuelsson, T. (2008), RNA (New York, N.Y.), 14(1), 1-10. doi:10.1261/rna.782308) and it could be shown that its binding to the histone stem-loop sequence is dependent on the stem-loop structure and that the minimum binding site contains at least 3 nucleotides 5' and 2 nucleotides 3' of the stem-loop (Pandey, N. B., et al. (1994), *Molecular and Cellular Biology*, 14(3), 1709-1720 and Williams, A. S., & Marzluff, W. F., (1995), *Nucleic Acids Research*, 23(4), 654-662).

Even though histone genes are generally classified as either "replication-dependent", giving rise to mRNA ending in a histone stem-loop, or "replacement-type", giving rise to mRNA bearing a poly(A)-tail instead, naturally occurring mRNAs containing both a histone stem-loop and poly(A) or oligo(A) 3' thereof have been identified in some very rare cases. Sanchez et al. examined the effect of naturally occurring oligo(A) tails appended 3' of the histone stem-loop of histone mRNA during *Xenopus oogenesis* using Luciferase as a reporter protein and found that the oligo(A) tail is an active part of the translation repression mechanism that silences histone mRNA during oogenesis and its removal is part of the mechanism that activates translation of histone mRNAs (Sanchez, R. and W. F. Marzluff (2004), Mol Cell Biol 24(6): 2513-25).

Furthermore, the requirements for regulation of replication dependent histones at the level of pre-mRNA processing and mRNA stability have been investigated using artificial constructs coding for the marker protein alpha Globin, taking advantage of the fact that the globin gene contains introns as opposed to the intron-less histone genes. For this purpose constructs were generated in which the alpha globin coding sequence was followed by a histone stem-loop signal (histone stem-loop followed by the histone downstream element) and a polyadenylation signal (Whitelaw, E., et al. (1986). Nucleic Acids Research, 14(17), 7059-7070; Pandey, N. B., & Marzluff, W. F. (1987). Molecular and Cellular Biology, 7(12), 4557-4559; Pandey, N. B., et al. (1990). Nucleic Acids Research, 18(11), 3161-3170).

In another approach Lüscher et al. investigated the cell-cycle dependent regulation of a recombinant histone H4 gene. Constructs were generated in which the H4 coding sequence was followed by a histone stem-loop signal and a polyadenylation signal, the two processing signals incidentally separated by a galactokinase coding sequence (Lüscher, B. et al., (1985). Proc. Natl. Acad. Sci. USA, 82(13), 4389-4393).

Additionally, Stauber et al. identified the minimal sequence required to confer cell-cycle regulation on histone H4 mRNA levels. For these investigations constructs were used, comprising a coding sequence for the selection marker Xanthine:guanine phosphoribosyl transferase (GPT) preceding a histone stem-loop signal followed by a polyadenylation signal (Stauber, C. et al., (1986). EMBO J, 5(12), 3297-3303).

Examining histone pre-mRNA processing Wagner et al. identified factors required for cleavage of histone pre-mRNAs using a reporter construct placing EGFP between a histone stem-loop signal and a polyadenylation signal, such that EGFP was expressed only in case histone pre-mRNA processing was disrupted (Wagner, E. J. et al., (2007). Mol Cell 28(4), 692-9).

To be noted, translation of polyadenylated mRNA usually requires the 3' poly(A) sequence to be brought into proximity of the 5' CAP. This is mediated through protein-protein interaction between the poly(A) binding protein and eukaryotic initiation factor eIF4G. With respect to replication-dependent histone mRNAs, an analogous mechanism has been uncovered. In this context, Gallie et al. show that the histone stem-loop is functionally similar to a poly(A) sequence in that it enhances translational efficiency and is co-dependent on a 5'-CAP in order to establish an efficient level of translation. They showed that the histone stem-loop is sufficient and necessary to increase the translation of a reporter mRNA in transfected Chinese hamster ovary cells but must be positioned at the 3'-terminus in order to function optimally. Therefore, similar to the poly(A) tail on other mRNAs, the 3' end of these histone mRNAs appears to be essential for translation in vivo and is functionally analogous to a poly(A) tail (Gallie, D. R., Lewis, N. J., & Marzluff, W. F. (1996), Nucleic Acids Research, 24(10), 1954-1962).

Additionally, it could be shown that SLBP is bound to the cytoplasmic histone mRNA and is required for its translation. Even though SLBP does not interact directly with eIF4G, the domain required for translation of histone mRNA interacts with the recently identified protein SLIP1. In a further step, SLIP1 interacts with eIF4G and allows to circularize histone mRNA and to support efficient translation of histone mRNA by a mechanism similar to the translation of polyadenylated mRNAs.

As mentioned above, gene therapy approaches normally use DNA to transfer the coding information into the cell which is then transcribed into mRNA, carrying the naturally occurring elements of an mRNA, particularly the 5'-CAP structure and the 3' poly(A) sequence to ensure expression of the encoded therapeutic or antigenic protein.

However, in many cases expression systems based on the introduction of such nucleic acids into the patient's cells or tissue and the subsequent expression of the desired polypeptides coded for by these nucleic acids do not exhibit the desired, or even the required, level of expression which may allow for an efficient therapy, irrespective as to whether DNA or RNA is used.

In the prior art, different attempts have hitherto been made to increase the yield of the expression of an encoded protein, in particular by use of improved expression systems, both in vitro and/or in vivo. Methods for increasing expression described generally in the prior art are conventionally based on the use of expression vectors or cassettes containing specific promoters and corresponding regulation elements. As these expression vectors or cassettes are typically limited to particular cell systems, these expression systems have to be adapted for use in different cell systems. Such adapted expression vectors or cassettes are then usually transfected into the cells and typically treated in dependence of the specific cell line. Therefore, preference is given primarily to those nucleic acid molecules which are able to express the encoded proteins in a target cell by systems inherent in the cell, independent of promoters and regulation elements which are specific for particular cell types. In this context, there can be distinguished between mRNA stabilizing elements and elements which increase translation efficiency of the mRNA.

mRNAs which are optimized in their coding sequence and which are in general suitable for such a purpose are described in application WO 02/098443 (CureVac GmbH). For example, WO 02/098443 describes mRNAs that are stabilised in general form and optimised for translation in their coding regions. WO 02/098443 further discloses a method for determining sequence modifications. WO 02/098443 additionally describes possibilities for substituting adenine and uracil nucleotides in mRNA sequences in order to increase the guanine/cytosine (G/C) content of the sequences. According to WO 02/098443, such substitutions and adaptations for increasing the G/C content can be used for gene therapeutic applications but also genetic vaccines in the treatment of cancer or infectious diseases. In this context, WO 02/098443 generally mentions sequences as a base sequence for such modifications, in which the modified mRNA codes for at least one biologically active peptide or polypeptide, which is translated in the patient to be treated, for example, either not at all or inadequately or with faults. Alternatively, WO 02/098443 proposes mRNAs coding for antigens e.g. pathogenic antigens or viral antigens as a base sequence for such modifications.

In a further approach to increase the expression of an encoded protein the application WO 2007/036366 describes the positive effect of long poly(A) sequences (particularly longer than 120 bp) and the combination of at least two 3' untranslated regions of the beta globin gene on mRNA stability and translational activity.

However, even though all these latter prior art documents already try to provide quite efficient tools for gene therapy approaches and additionally improved mRNA stability and translational activity, there still remains the problem of a generally lower stability of RNA-based applications versus DNA vaccines and DNA based gene therapeutic approaches. Accordingly, there still exists a need in the art to provide improved tools for gene therapy approaches and genetic vaccination or as a supplementary therapy for conventional treatments as discussed above, which allow for better provision of encoded proteins in vivo, e.g. via a further improved mRNA stability and/or translational activity, preferably for gene therapy and genetic vaccination.

Furthermore despite of all progress in the art, efficient expression of an encoded peptide or protein in cell-free systems, cells or organisms (recombinant expression) is still a challenging problem.

The object underlying the present invention is, therefore, to provide additional and/or alternative methods to increase expression of an encoded protein, preferably via further stabilization of the mRNA and/or an increase of the translational efficiency of such an mRNA with respect to such nucleic acids known from the prior art for the use in genetic vaccination in the therapeutic or prophylactic treatment of infectious diseases.

This object is solved by the subject matter of the attached claims. Particularly, the object underlying the present invention is solved according to a first aspect by an inventive nucleic acid sequence comprising or coding for a) a coding region, encoding at least one peptide or protein which comprises a pathogenic antigen or a fragment, variant or derivative thereof;
b) at least one histone stem-loop, and
c) a poly(A) sequence or a polyadenylation signal, preferably for increasing the expression of said encoded peptide or protein.

Alternatively, any appropriate stem loop sequence other than a histone stem loop sequence (derived from histone genes, in particular histone genes of the families H1, H2A, H2B, H3 and H4) may be employed by the present invention in all of its aspects and embodiments.

In this context, it is particularly preferred that the inventive nucleic acid according to the first aspect of the present invention is produced at least partially by DNA or RNA synthesis, preferably as described herein or is an isolated nucleic acid.

The present invention is based on the surprising finding of the present inventors, that the combination of a poly(A) sequence or polyadenylation signal and at least one histone stem-loop, even though both representing alternative mechanisms in nature, acts synergistically as this combination increases the protein expression manifold above the level observed with either of the individual elements. The synergistic effect of the combination of poly(A) and at least one histone stem-loop is seen irrespective of the order of poly(A) and histone stem-loop and irrespective of the length of the poly(A) sequence.

Therefore it is particularly preferred that the inventive nucleic acid sequence comprises or codes for a) a coding region, encoding at least one peptide or protein which comprises a pathogenic antigen or a fragment, variant or derivative thereof; b) at least one histone stem-loop, and c) a poly(A) sequence or polyadenylation sequence; preferably for increasing the expression level of said encoded peptide or protein, wherein the encoded protein is preferably no histone protein, in particular no histone protein of the H4, H3, H2A and/or H2B histone family or a fragment, derivative or variant thereof retaining histone(-like) function), namely forming a nucleosome. Also, the encoded protein typically does not correspond to a histone linker protein of the H1 histone family. The inventive nucleic acid molecule does typically not contain any regulatory signals (5' and/or, particularly, 3' of a mouse histone gene, in particular not of a mouse histone gene H2A and, further, most preferably not of the mouse histone gene H2A614. In particular, it does not contain a histone stem loop and/or a histone stem loop processing signal from a mouse histone gene, in particular not of mouse histone gene H2A und, most preferably not of mouse histone gene H2A614.

Also, the inventive nucleic acid typically does not provide a reporter protein (e.g. Luciferase, GFP, EGFP, β-Galactosidase, particularly EGFP), galactokinase (galK) and/or marker or selection protein (e.g. alpha-Globin, Galactokinase and Xanthine:Guanine phosphoribosyl transferase (GPT)) or a bacterial reporter protein, e.g. chloramphenicol acetyl transferase (CAT) or other bacterial antibiotics resistance proteins, e.g. derived from the bacterial neo gene in its element (a).

A reporter, marker or selection protein is typically understood not to be an antigenic protein according to the invention. A reporter, marker or selection protein or its underlying gene is commonly used as a research tool in bacteria, cell culture, animals or plants. They confer on organisms (preferably heterologously) expressing them an easily identifiable property, which may be measured or which allows for selection. Specifically, marker or selection proteins exhibit a selectable function. Typically, such selection, marker or reporter proteins do not naturally occur in humans or other mammals, but are derived from other organisms, in particular from bacteria or plants. Accordingly, proteins with selection, marker or reporter function originating from lower species (e.g. bacteria) are preferably excluded from being understood as "antigenic protein" according to the present invention. An antigenic protein in this regard is meant to correspond to a protein, which triggers an immunological reaction which allows to immunologically protect the subject against an infection by an organism or virus which exerts a pathological reaction in the subject resulting in a disease state. In particular, a selection, marker or reporter protein allows to identify transformed cells by in vitro assays based e.g. on fluorescence or other spectroscopic techniques and resistance towards antibiotics. Selection, reporter or marker genes awarding such properties to transformed cells are therefore typically not understood to be a pathogenic antigenic protein according to the invention.

In any case, reporter, marker or selection proteins do usually not exert any antigenic effect as a result of the immunological response (of the subject to be treated) towards the pathogenic antigen. If any single reporter, marker or selection protein should nevertheless do so (in addition to its reporter, selection or marker function), such a reporter, marker or selection protein is preferably not understood to be a "pathogenic antigen" within the meaning of the present invention.

In contrast, a pathogenic antigen (including its fragments, variants and derivatives), in particular excluding histone genes of the families H1, H2A, H2B, H3 and H4, according to the present invention does typically not exhibit a selection, marker or reporter function. If any single "pathogenic antigen" nevertheless should do so (in addition to its antigenic function), such a pathogenic antigen is preferably not understood to be a "selection, marker or reporter protein" within the meaning of the present invention.

It is most preferably understood that a pathogenic antigen according to the invention is derived from pathogenic organisms, preferably, bacteria or viruses, exerting an immunological function. Typically, such antigens do not qualify as selection, marker or reporter protein.

Accordingly, it is preferred that the coding region (a) encoding at least one peptide or protein is heterologous to at least (b) the at least one histone stem loop, or more broadly, to any appropriate stem loop. In other words, "heterologous" in the context of the present invention means that the at least one stem loop sequence does not naturally occur as a (regulatory) sequence (e.g. at the 3'UTR) of the specific gene, which encodes the (pathogenic) antigenic protein or peptide of element (a) of the inventive nucleic acid. Accordingly, the (histone) stem loop of the inventive nucleic acid is derived preferably from the 3' UTR of a gene other than the one comprising the coding region of element (a) of the inventive nucleic acid. E.g., the coding region of element (a) will not encode a histone protein or a fragment, variant or derivative thereof (retaining the function of a histone protein), if the inventive nucleic is heterologous, but will encode any other peptide or sequence (of the same or another species) which exerts a biological function, preferably an antigenic function other than a histone(-like) function, e.g. will encode an antigenic protein (exerting an antigenic function, e.g. by triggering the reaction of the subject's immune system, e.g. by an antibody reaction, thereby enabling the inventive nucleic acid to act as a vaccine in e.g. mammalians, in particular in humans.

In this context it is particularly preferred that the inventive nucleic acid comprises or codes for in 5'- to 3'-direction:
a) a coding region, encoding at least one peptide or protein which comprises a pathogenic antigen or a fragment, variant or derivative thereof;
b) at least one histone stem-loop, optionally without a histone downstream element (HDE) 3' to the histone stem-loop
c) a poly(A) sequence or a polyadenylation signal.

The term "histone downstream element (HDE) refers to a purine-rich polynucleotide stretch of about 15 to 20 nucleotides 3' of naturally occurring histone stem-loops, which represents the binding site for the U7 snRNA involved in processing of histone pre-mRNA into mature histone mRNA. For example in sea urchins the HDE is CAAGAAAGA (Dominski, Z. and W. F. Marzluff (2007), Gene 396(2): 373-90).

Furthermore it is preferable that the inventive nucleic acid according to the first aspect of the present invention does not comprise an intron.

In another particular preferred embodiment, the inventive nucleic acid sequence according to the first aspect of the present invention comprises or codes for from 5' to 3':
a) a coding region, preferably encoding at least one peptide or protein which comprises a pathogenic antigen or a fragment, variant or derivative thereof;
c) a poly(A) sequence; and
b) at least one histone stem-loop.

The inventive nucleic acid sequence according to the first embodiment of the present invention comprise any suitable nucleic acid, selected e.g. from any (single-stranded or double-stranded) DNA, preferably, without being limited thereto, e.g. genomic DNA, plasmid DNA, single-stranded DNA molecules, double-stranded DNA molecules, or may be selected e.g. from any PNA (peptide nucleic acid) or may be selected e.g. from any (single-stranded or double-stranded) RNA, preferably a messenger RNA (mRNA); etc. The inventive nucleic acid sequence may also comprise a viral RNA (vRNA). However, the inventive nucleic acid sequence may not be a viral RNA or may not contain a viral RNA. More specifically, the inventive nucleic acid sequence may not contain viral sequence elements, e.g. viral enhancers or viral promotors (e.g. no inactivated viral promoter or sequence elements, more specifically not inactivated by replacement strategies), or other viral sequence elements, or viral or retroviral nucleic acid sequences. More specifically, the inventive nucleic acid sequence may not be a retroviral or viral vector or a modified retroviral or viral vector.

In any case, the inventive nucleic acid sequence may or may not contain an enhancer and/or promoter sequence, which may be modified or not or which may be activated or not. The enhancer and or promoter may be plant expressible or not expressible, and/or in eukaryotes expressible or not expressible and/or in prokaryotes expressible or not expressible. The inventive nucleic acid sequence may contain a sequence encoding a (self-splicing) ribozyme or not.

In specific embodiments the inventive nucleic acid sequence may be or may comprise a self-replicating RNA (replicon).

Preferably, the inventive nucleic acid sequence is a plasmid DNA, or an RNA, particularly an mRNA.

In particular embodiments of the first aspect of the present invention, the inventive nucleic acid is a nucleic acid sequence comprised in a nucleic acid suitable for in vitro transcription, particularly in an appropriate in vitro transcription vector (e.g. a plasmid or a linear nucleic acid sequence comprising specific promoters for in vitro transcription such as T3, T7 or Sp6 promoters).

In further particular preferred embodiments of the first aspect of the present invention, the inventive nucleic acid is comprised in a nucleic acid suitable for transcription and/or translation in an expression system (e.g. in an expression vector or plasmid), particularly a prokaryotic (e.g. bacteria like *E. coli*) or eukaryotic (e g mammalian cells like CHO cells, yeast cells or insect cells or whole organisms like plants or animals) expression system.

The term "expression system" means a system (cell culture or whole organisms) which is suitable for production of peptides, proteins or RNA particularly mRNA (recombinant expression).

The inventive nucleic acid sequence according to the first aspect of the present invention comprises or codes for at least one histone stem-loop. In the context of the present invention, such a histone stem-loop is typically derived from histone genes and comprises an intramolecular base pairing of two neighbored entirely or partially reverse complementary sequences, thereby forming a stem-loop. A stem-loop in general irrespective of whether it is a histone stem loop or not, can occur in single-stranded DNA or, more commonly, in RNA. The structure is also known as a hairpin or hairpin loop and usually consists of a stem and a (terminal) loop within a consecutive sequence, wherein the stem is formed by two neighbored entirely or partially reverse complementary sequences separated by a short sequence as sort of spacer, which builds the loop of the stem-loop structure. The two neighbored entirely or partially reverse complementary sequences may be defined as e.g. stem loop elements stem1 and stem2. The stem loop is formed when these two neighbored entirely or partially reverse complementary sequences, e.g. stem loop elements stem1 and stem2, form base-pairs with each other, leading to a double stranded nucleic acid sequence stretch comprising an unpaired loop at its terminal ending formed by the short sequence located between stem loop elements stem1 and stem2 on the consecutive sequence. The unpaired loop thereby typically represents a region of the nucleic acid which is not capable of base pairing with either of these stem loop elements. The resulting lollipop-shaped structure is a key building block of many RNA secondary structures. The formation of a stem-loop structure is thus dependent on the stability of the resulting stem and loop regions, wherein the first prerequisite is typically the presence of a sequence that can fold back on itself to form a paired double strand. The stability of paired stem loop elements is determined by the length, the number of mismatches or bulges it contains (a small number of mismatches is typically tolerable, especially in a long double stranded stretch), and the base composition of the paired region. In the context of the present invention, a loop length of 3 to 15 bases is conceivable, while a more preferred optimal loop length is 3-10 bases, more preferably 3 to 8, 3 to 7, 3 to 6 or even more preferably 4 to 5 bases, and most preferably 4 bases. The stem sequence forming the double stranded structure typically has a length of between 5 to 10 bases, more preferably, between 5 to 8 bases.

In the context of the present invention, a histone stem-loop is typically derived from histone genes (e.g. genes from the histone families H1, H2A, H2B, H3, H4) and comprises an intramolecular base pairing of two neighbored entirely or partially reverse complementary sequences, thereby forming a stem-loop. Typically, a histone 3' UTR stem-loop is an RNA element involved in nucleocytoplasmic transport of the histone mRNAs, and in the regulation of stability and of translation efficiency in the cytoplasm. The mRNAs of metazoan histone genes lack polyadenylation and a poly-A tail, instead 3' end processing occurs at a site between this highly conserved stem-loop and a purine rich region around 20 nucleotides downstream (the histone downstream element, or HDE). The histone stem-loop is bound by a 31 kDa stem-loop binding protein (SLBP—also termed the histone hairpin binding protein, or HBP). Such histone stem-loop structures are preferably employed by the present invention in combination with other sequence elements and structures, which do not occur naturally (which means in untransformed living organisms/cells) in histone genes, but are combined—according to the invention—to provide an artificial, heterologous nucleic acid. Accordingly, the present invention is particularly based on the finding that an artificial (non-native) combination of a histone stem-loop structure with other heterologous sequence elements, which do not occur in histone genes or metazoan histone genes and are isolated from operational and/or regulatory sequence regions (influencing transcription and/or translation) of genes coding for proteins other than histones, provide advantageous effects. Accordingly, one aspect of the invention provides the combination of a histone stem-loop structure with a poly(A) sequence or a sequence representing a polyadenylation signal (3'-terminal of a coding region), which does not occur in metazoan histone genes. According to another preferred aspect of the invention, a combination of a histone stem-loop structure with a coding region coding for a pathogenic antigen, which does, preferably not occur in metazoan histone genes, is provided herewith (coding region and histone stem loop sequence are heterologous). It is preferred, if such pathogenic antigens do not occur in metazoa at all, but are derived from unicellular organisms, e.g. bacteria, or from viruses. In a still further preferred embodiment, all the elements (a), (b) and (c) of the inventive nucleic acid are heterologous to each other and are combined artificially from three different sources, e.g. the antigen coding region from bacteria or virus, the histone stem loop from a metazoan histone gene and the poly(A) sequence or the polyadenylation signal from e.g. a metazoan gene other than a histone gene.

A histone stem loop is, therefore, a stem-loop structure as described herein, which, if preferably functionally defined, exhibits/retains the property of binding to its natural binding partner, the stem-loop binding protein (SLBP—also termed the histone hairpin binding protein, or HBP).

According to the present invention the histone stem loop sequence according to component (b) of claim 1 may not derived from a mouse histone protein. More specifically, the histone stem loop sequence may not be derived from mouse histone gene H2A614. Also, the nucleic acid of the invention may neither contain a mouse histone stem loop sequence nor contain mouse histone gene H2A614. Further, the inventive nucleic acid sequence may not contain a stem-loop processing signal, more specifically, a mouse histone processing signal and, most specifically, may not contain mouse stem loop processing signal H2kA614, even if the inventive nucleic acid sequence may contain at least one mammalian histone gene. However, the at least one mammalian histone gene may not be Seq. ID No. 7 of WO 01/12824.

According to one preferred embodiment of the first inventive aspect, the inventive nucleic acid sequence comprises or codes for at least one histone stem-loop sequence, preferably according to at least one of the following formulae (I) or (II):

formula (I) (stem-loop sequence without stem bordering elements):

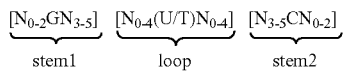

formula (II) (stem-loop sequence with stem bordering elements):

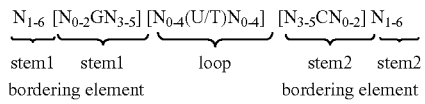

wherein:
stem1 or stem2 bordering elements $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;

stem1 $[N_{0-2}GN_{3-5}]$ is reverse complementary or partially reverse complementary with element stem2, and is a consecutive sequence between of 5 to 7 nucleotides;
wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;
wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and
wherein G is guanosine or an analogue thereof, and may be optionally replaced by a cytidine or an analogue thereof, provided that its complementary nucleotide cytidine in stem2 is replaced by guanosine;

loop sequence $[N_{0-4}(U/T)N_{0-4}]$ is located between elements stem1 and stem2, and is a consecutive sequence of 3 to 5 nucleotides, more preferably of 4 nucleotides;
wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine;

stem2 $[N_{3-5}CN_{0-2}]$ is reverse complementary or partially reverse complementary with element stem1, and is a consecutive sequence between of 5 to 7 nucleotides;
wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;
wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and
wherein C is cytidine or an analogue thereof, and may be optionally replaced by a guanosine or an analogue thereof provided that its complementary nucleotide guanosine in stem1 is replaced by cytidine;

wherein
stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one or more bases in one stem do not have a complementary base in the reverse complementary sequence of the other stem.

In the above context, a wobble base pairing is typically a non-Watson-Crick base pairing between two nucleotides. The four main wobble base pairs in the present context, which may be used, are guanosine-uridine, inosine-uridine, inosine-adenosine, inosine-cytidine (G-U/T, I-U/T, I-A and I-C) and adenosine-cytidine (A-C).

Accordingly, in the context of the present invention, a wobble base is a base, which forms a wobble base pair with a further base as described above. Therefore non-Watson-Crick base pairing, e.g. wobble base pairing, may occur in the stem of the histone stem-loop structure according to the present invention.

In the above context a partially reverse complementary sequence comprises maximally 2, preferably only one mismatch in the stem-structure of the stem-loop sequence formed by base pairing of stem1 and stem2. In other words, stem1 and stem2 are preferably capable of (full) base pairing with each other throughout the entire sequence of stem1 and stem2 (100% of possible correct Watson-Crick or non-Watson-Crick base pairings), thereby forming a reverse complementary sequence, wherein each base has its correct Watson-Crick or non-Watson-Crick base pendant as a complementary binding partner.

Alternatively, stem1 and stem2 are preferably capable of partial base pairing with each other throughout the entire sequence of stem1 and stem2, wherein at least about 70%, 75%, 80%, 85%, 90%, or 95% of the 100% possible correct Watson-Crick or non-Watson-Crick base pairings are occupied with the correct Watson-Crick or non-Watson-Crick base pairings and at most about 30%, 25%, 20%, 15%, 10%, or 5% of the remaining bases are unpaired.

According to a preferred embodiment of the first inventive aspect, the at least one histone stem-loop sequence (with stem bordering elements) of the inventive nucleic acid sequence as defined herein comprises a length of about 15 to about 45 nucleotides, preferably a length of about 15 to about 40 nucleotides, preferably a length of about 15 to about 35 nucleotides, preferably a length of about 15 to about 30 nucleotides and even more preferably a length of about 20 to about 30 and most preferably a length of about 24 to about 28 nucleotides.

According to a further preferred embodiment of the first inventive aspect, the at least one histone stem-loop sequence (without stem bordering elements) of the inventive nucleic acid sequence as defined herein comprises a length of about 10 to about 30 nucleotides, preferably a length of about 10 to about 20 nucleotides, preferably a length of about 12 to about 20 nucleotides, preferably a length of about 14 to about 20 nucleotides and even more preferably a length of about 16 to about 17 and most preferably a length of about 16 nucleotides.

According to a further preferred embodiment of the first inventive aspect, the inventive nucleic acid sequence according to the first aspect of the present invention may comprise or code for at least one histone stem-loop sequence according to at least one of the following specific formulae (Ia) or (IIa):

formula (Ia) (stem-loop sequence without stem bordering elements):

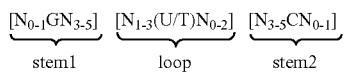

formula (IIa) (stem-loop sequence with stem bordering elements):

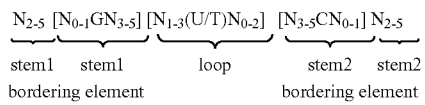

wherein:
N, C, G, T and U are as defined above.

According to a further more particularly preferred embodiment of the first aspect, the inventive nucleic acid sequence may comprise or code for at least one histone stem-loop sequence according to at least one of the following specific formulae (Ib) or (IIb):

formula (Ib) (stem-loop sequence without stem bordering elements):

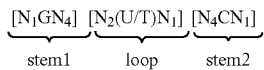

formula (IIb) (stem-loop sequence with stem bordering elements):

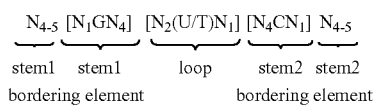

wherein: N, C, G, T and U are as defined above.

According to an even more preferred embodiment of the first inventive aspect, the inventive nucleic acid sequence according to the first aspect of the present invention may comprise or code for at least one histone stem-loop sequence according to at least one of the following specific formulae (Ic) to (Ih) or (IIc) to (IIh), shown alternatively in its stem-loop structure and as a linear sequence representing histone stem-loop sequences as generated according to Example 1 formula (Ic): (metazoan and protozoan histone stem-loop consensus sequence without stem bordering elements):

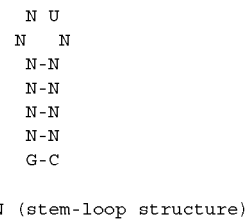

N-N (stem-loop structure)

(SEQ ID NO: 1)
NGNNNNNNUNNNNNCN
(linear sequence)

formula (IIc): (metazoan and protozoan histone stem-loop consensus sequence with stem bordering elements):

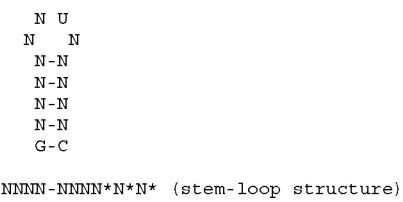

N*N*NNNN-NNNN*N*N* (stem-loop structure)

(SEQ ID NO: 2)
N*N*NNNNGNNNNNNUNNNNNCNNNN*N*N*
(linear sequence)

formula (Id): (without stem bordering elements)

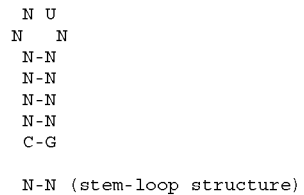

N-N (stem-loop structure)

(SEQ ID NO: 3)
NCNNNNNNUNNNNNGN
(linear sequence)

formula (IId): (with stem bordering elements)

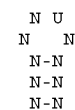

-continued
```
        N-N
        C-G

N*N*NNNN-NNNN*N*N* (stem-loop structure)
                                        (SEQ ID NO: 4)
N*N*NNNNCNNNNNNUNNNNNGNNNN*N*N*
(linear sequence)
``` formula (Ie): (protozoan histone stem-loop consensus sequence without stem bordering elements)

```
          N U
         N   N
        N-N
        N-N
        N-N
        N-N
        G-C

D-H (stem-loop structure)
                                        (SEQ ID NO: 5)
DGNNNNNNUNNNNNCH
(linear sequence)
``` formula (IIe): (protozoan histone stem-loop consensus sequence with stem bordering elements)

```
          N U
         N   N
        N-N
        N-N
        N-N
        N-N
        G-C

N*N*NNND-HNNN*N*N* (stem-loop structure)
                                        (SEQ ID NO: 6)
N*N*NNNDGNNNNNNUNNNNNCHNNN*N*N*
(linear sequence)
``` formula (If): (metazoan histone stem-loop consensus sequence without stem bordering elements)

```
          N U
         N   N
        Y-V
        Y-N
        B-D
        N-N
        G-C

N-N (stem-loop structure)
                                        (SEQ ID NO: 7)
NGNBYYNNUNVNDNCN
(linear sequence)
``` formula (IIf): (metazoan histone stem-loop consensus sequence with stem bordering elements)

```
          N U
         N   N
        Y-V
        Y-N
        B-D
```

```
        N-N
        G-C

N*N*NNNN-NNNN*N*N* (stem-loop structure)
                                        (SEQ ID NO: 8)
N*N*NNNNGNBYYNNUNVNDNCNNNN*N*N*
(linear sequence)
``` formula (Ig): (vertebrate histone stem-loop consensus sequence without stem bordering elements)

```
          N U
         D   H
        Y-A
        Y-B
        Y-R
        H-D
        G-C

N-N (stern-loop structure)
                                        (SEQ ID NO: 9)
NGHYYYDNUHABRDCN
(linear sequence)
``` formula (IIg): (vertebrate histone stem-loop consensus sequence with stem bordering elements)

```
          N U
         D   H
        Y-A
        Y-B
        Y-R
        H-D
        G-C

N*N*HNNN-NNNN*N*H* (stem-loop structure)
                                        (SEQ ID NO: 10)
N*N*HNNNGHYYYDNUHABRDCNNNN*N*H*
(linear sequence)
``` formula (Ih): (human histone stem-loop consensus sequence (*Homo sapiens*) without stem bordering elements)

```
          Y U
         D   H
        U-A
        C-S
        Y-R
        H-R
        G-C

D-C (stern-loop structure)
                                        (SEQ ID NO: 11)
DGHYCUDYUHASRRCC
(linear sequence)
``` formula (IIh): (human histone stem-loop consensus sequence (*Homo sapiens*) with stem bordering elements)

```
          Y U
         D   H
        U-A
        C-S
        Y-R
```

```
       H-R
       G-C

N*H*AAHD-CVHB*N*H* (stem loop structure)
                                      (SEQ ID NO: 12)
N*H*AAHDGHYCUDYUHASRRCCVHB*N*H*
(linear sequence)
``` wherein in each of above formulae (Ic) to (Ih) or (IIc) to (IIh): N, C, G, A, T and U are as defined above; each U may be replaced by T; each (highly) conserved G or C in the stem elements 1 and 2 may be replaced by its complementary nucleotide base C or G, provided that its complementary nucleotide in the corresponding stem is replaced by its complementary nucleotide in parallel; and/or G, A, T, U, C, R, Y, M, K, S, W, H, B, V, D, and N are nucleotide bases as defined in the following Table:

| abbreviation | Nucleotide bases | remark |
| --- | --- | --- |
| G | G | Guanine |
| A | A | Adenine |
| T | T | Thymine |
| U | U | Uracile |
| C | C | Cytosine |
| R | G or A | Purine |
| Y | T/U or C | Pyrimidine |
| M | A or C | Amino |
| K | G or T/U | Keto |
| S | G or C | Strong (3H bonds) |
| W | A or T/U | Weak (2H bonds) |
| H | A or C or T/U | Not G |
| B | G or T/U or C | Not A |
| V | G or C or A | Not T/U |
| D | G or A or T/U | Not C |
| N | G or C or T/U or A | Any base |
| * | Present or not | Base may be present or not |

In this context it is particularly preferred that the histone stem-loop sequence according to at least one of the formulae (I) or (Ia) to (Ih) or (II) or (IIa) to (IIh) of the present invention is selected from a naturally occurring histone stem loop sequence, more particularly preferred from protozoan or metazoan histone stem-loop sequences, and even more particularly preferred from vertebrate and mostly preferred from mammalian histone stem-loop sequences especially from human histone stem-loop sequences.

According to a particularly preferred embodiment of the first aspect, the histone stem-loop sequence according to at least one of the specific formulae (I) or (Ia) to (Ih) or (II) or (IIa) to (IIh) of the present invention is a histone stem-loop sequence comprising at each nucleotide position the most frequently occurring nucleotide, or either the most frequently or the second-most frequently occurring nucleotide of naturally occurring histone stem-loop sequences in metazoa and protozoa (FIG. 1), protozoa (FIG. 2), metazoa (FIG. 3), vertebrates (FIG. 4) and humans (FIG. 5) as shown in FIG. 1-5. In this context it is particularly preferred that at least 80%, preferably at least 85%, or most preferably at least 90% of all nucleotides correspond to the most frequently occurring nucleotide of naturally occurring histone stem-loop sequences.

In a further particular embodiment of the first aspect, the histone stem-loop sequence according to at least one of the specific formulae (I) or (Ia) to (Ih) of the present invention is selected from following histone stem-loop sequences (without stem-bordering elements) representing histone stem-loop sequences as generated according to Example 1:

```
                            (SEQ ID NO: 13 according to formula (Ic))
VGYYYYHHTHRVVRCB (SEQ ID NO: 14 according to formula (Ic))
SGYYYTTYTMARRRCS (SEQ ID NO: 15 according to formula (Ic))
SGYYCTTTTMAGRRCS (SEQ ID NO: 16 according to formula (Ie))
DGNNNBNNTHVNNNCH (SEQ ID NO: 17 according to formula (Ie))
RGNNNYHBTHRDNNCY (SEQ ID NO: 18 according to formula (Ie))
RGNDBYHYTHRDHNCY (SEQ ID NO: 19 according to formula (If))
VGYYYTYHTHRVRRCB (SEQ ID NO: 20 according to formula (If))
SGYYCTTYTMAGRRCS (SEQ ID NO: 21 according to formula (If))
SGYYCTTTTMAGRRCS (SEQ ID NO: 22 according to formula (Ig))
GGYYCTTYTHAGRRCC (SEQ ID NO: 23 according to formula (Ig))
GGCYCTTYTMAGRGCC (SEQ ID NO: 24 according to formula (Ig))
GGCTCTTTTMAGRGCC (SEQ ID NO: 25 according to formula (Ih))
DGHYCTDYTHASRRCC (SEQ ID NO: 26 according to formula (Ih))
GGCYCTTTTHAGRGCC (SEQ ID NO: 27 according to formula (Ih))
GGCYCTTTTMAGRGCC
```

Furthermore in this context following histone stem-loop sequences (with stem bordering elements) as generated according to Example 1 according to one of specific formulae (II) or (IIa) to (IIh) are particularly preferred:

```
                            (SEQ ID NO: 28 according to formula (IIc))
H*H*HHVVGYYYYHHTHRVVRCBVHH*N*N*

(SEQ ID NO: 29 according to formula (IIc))
M*H*MHMSGYYYTTYTMARRRCSMCH*H*H*

(SEQ ID NO: 30 according to formula (IIc))
M*M*MMMSGYYCTTTTMAGRRCSACH*M*H*

(SEQ ID NO: 31 according to formula (IIe))
N*N*NNNDGNNNBNNTHVNNNCHNHN*N*N*

(SEQ ID NO: 32 according to formula (IIe))
N*N*HHNRGNNNYHBTHRDNNCYDHH*N*N*

(SEQ ID NO: 33 according to formula (IIe))
N*H*HHVRGNDBYHYTHRDHNCYRHH*H*H*

(SEQ ID NO: 34 according to formula (IIf))
H*H*MHMVGYYYTYHTHRVRRCBVMH*H*N*

(SEQ ID NO: 35 according to formula (IIf))
M*M*MMMSGYYCTTYTMAGRRCSMCH*H*H*

(SEQ ID NO: 36 according to formula (IIf))
M*M*MMMSGYYCTTTTMAGRRCSACH*M*H*

(SEQ ID NO: 37 according to formula (IIg))
H*H*MAMGGYYCTTYTHAGRRCCVHN*N*M*
```

-continued (SEQ ID NO: 38 according to formula (IIg))
H*H*AAMGGCYCTTYTMAGRGCCVCH*H*M*

(SEQ ID NO: 39 according to formula (IIg))
M*M*AAMGGCTCTTTTMAGRGCCMCY*M*M*

(SEQ ID NO: 40 according to formula (IIh))
N*H*AAHDGHYCTDYTHASRRCCVHB*N*H*

(SEQ ID NO: 41 according to formula (IIh))
H*H*AAMGGCYCTTTTHAGRGCCVMY*N*M*

(SEQ ID NO: 42 according to formula (IIh))
H*M*AAAGGCYCTTTTMAGRGCCRMY*H*M*

According to a further preferred embodiment of the first inventive aspect, the inventive nucleic acid sequence comprises or codes for at least one histone stem-loop sequence showing at least about 80%, preferably at least about 85%, more preferably at least about 90%, or even more preferably at least about 95%, sequence identity with the not to 100% conserved nucleotides in the histone stem-loop sequences according to at least one of specific formulae (I) or (Ia) to (Ih) or (II) or (IIa) to (IIh) or with a naturally occurring histone stem-loop sequence.

In a preferred embodiment, the histone stem loop sequence does not contain the loop sequence 5'-UUUC-3'. More specifically, the histone stem loop does not contain the stem/sequence 5'-GGCUCU-3' and/or the stem2 sequence 5'-AGAGCC-3', respectively. In another preferred embodiment, the stem loop sequence does not contain the loop sequence 5'-CCUGCCC-3' or the loop sequence 5'-UGAAU-3'. More specifically, the stem loop does not contain the stem/sequence 5'-CCUGAGC-3' or does not contain the stem/sequence 5'-ACCUUUCUCCA-3' (SEQ ID NO: 57) and/or the stem2 sequence 5'-GCUCAGG-3' or 5'-UGGAGAAAGGU-3' (SEQ ID NO: 58), respectively. Also, as far as the invention is not limited to histone stem loop sequences specifically, stem loop sequences are preferably not derived from a mammalian insulin receptor 3'-untranslated region. Also, preferably, the inventive nucleic acid may not contain histone stem loop processing signals, in particular not those derived from mouse histone gene H2A614 gene (H2kA614).

The inventive nucleic acid sequence according to the first aspect of the present invention may optionally comprise or code for a poly(A) sequence. When present, such a poly(A) sequence comprises a sequence of about 30 or, more preferably, of about 25 to about 400 adenosine nucleotides, preferably a sequence of about 50 to about 400 adenosine nucleotides, more preferably a sequence of about 50 to about 300 adenosine nucleotides, even more preferably a sequence of about 50 to about 250 adenosine nucleotides, most preferably a sequence of about 60 to about 250 adenosine nucleotides. In this context the term "about" refers to a deviation of ±10% of the value(s) it is attached to. Accordingly, the poly(A) sequence contains at least 25 or more than 25, more preferably, at least 30, more preferably at least 50 adenosine nucleotides. Therefore, such a poly (A) sequence does typically not contain less than 20 adenosine nucleotides. More particularly, it does not contain 10 and/or less than 10 adenosine nucleotides.

Preferably, the nucleic acid according of the present invention does not contain one or two or at least one or all but one or all of the components of the group consisting of: a sequence encoding a ribozyme (preferably a self-splicing ribozyme), a viral nucleic acid sequence, a histone stem-loop processing signal, in particular a histone-stem loop processing sequence derived from mouse histone H2A614 gene, a Neo gene, an inactivated promoter sequence and an inactivated enhancer sequence. Even more preferably, the nucleic acid according to the invention does not contain a ribozyme, preferably a self-splicing ribozyme, and one of the group consisting of: a Neo gene, an inactivated promoter sequence, an inactivated enhancer sequence, a histone stem-loop processing signal, in particular a histone-stem loop processing sequence derived from mouse histone H2A614 gene. Accordingly, the nucleic acid may in a preferred mode neither contain a ribozyme, preferably a self-splicing ribozyme, nor a Neo gene or, alternatively, neither a ribozyme, preferably a self-splicing ribozyme, nor any resistance gene (e.g. usually applied for selection). In another preferred mode, the nucleic acid of the invention may neither contain a ribozyme, preferably a self-splicing ribozyme nor a histone stem-loop processing signal, in particular a histone-stem loop processing sequence derived from mouse histone H2A614 gene Alternatively, according to the first aspect of the present invention, the inventive nucleic sequence optionally comprises a polyadenylation signal which is defined herein as a signal which conveys polyadenylation to a (transcribed) mRNA by specific protein factors (e.g. cleavage and polyadenylation specificity factor (CPSF), cleavage stimulation factor (CstF), cleavage factors I and II (CF I and CF II), poly(A) polymerase (PAP)). In this context a consensus polyadenylation signal is preferred comprising the NN(U/T)ANA consensus sequence. In a particular preferred aspect the polyadenylation signal comprises one of the following sequences: AA(U/T)AAA or A(U/T)(U/T)AAA (wherein uridine is usually present in RNA and thymidine is usually present in DNA). In some embodiments, the polyadenylation signal used in the inventive nucleic acid does not correspond to the U3 snRNA, U5, the polyadenylation processing signal from human gene G-CSF, or the SV40 polyadenylation signal sequences. In particular, the above polyadenylation signals are not combined with any antibiotics resistance gene (or any other reporter, marker or selection gene), in particular not with the resistance neo gene (neomycin phosphotransferase) (as the gene of the coding region according to element (a) of the inventive nucleic acid. And any of the above polyadenylation signals (which typically do not occur in the inventive nucleic acid) are preferably not combined with the histone stem loop or the histone stem loop processing signal from mouse histone gene H2A614 in an inventive nucleic acid.

The inventive nucleic acid sequence according to the first aspect of the present invention may furthermore encode a protein or a peptide, which comprises a pathogenic antigen or a fragment, variant or derivative thereof. Such pathogenic antigens are derived from pathogenic organisms, in particular bacterial, viral or protozoological (multicellular) pathogenic organisms, which evoke an immunological reaction by subject, in particular a mammalian subject, more particularly a human More specifically, pathogenic antigens are preferably surface antigens, e.g. proteins (or fragments of proteins, e.g. the exterior portion of a surface antigen) located at the surface of the virus or the bacterial or protozoological organism.

Pathogenic antigens are peptide or protein antigens preferably derived from a pathogen associated with infectious disease which are preferably selected from antigens derived from the pathogens *Acinetobacter baumannii*, *Anaplasma* genus, *Anaplasma phagocytophilum*, *Ancylostoma braziliense*, *Ancylostoma duodenale*, *Arcanobacterium haemolyticum*, *Ascaris lumbricoides*, *Aspergillus* genus, Astroviridae,

*Babesia* genus, *Bacillus anthracis, Bacillus cereus, Bartonella henselae*, BK virus, *Blastocystis hominis, Blastomyces dermatitidis, Bordetella pertussis, Borrelia burgdorferi, Borrelia* genus, *Borrelia* spp, *Brucella* genus, *Brugia malayi*, Bunyaviridae family, *Burkholderia cepacia* and other *Burkholderia* species, *Burkholderia mallei, Burkholderia pseudomallei*, Caliciviridae family, *Campylobacter* genus, *Candida albicans, Candida* spp, *Chlamydia trachomatis, Chlamydophila pneumoniae, Chlamydophila psittaci*, CJD prion, *Clonorchis sinensis, Clostridium botulinum, Clostridium difficile, Clostridium perfringens, Clostridium perfringens, Clostridium* spp, *Clostridium tetani, Coccidioides* spp, coronaviruses, *Corynebacterium diphtheriae, Coxiella burnetii*, Crimean-Congo hemorrhagic fever virus, *Cryptococcus neoformans, Cryptosporidium* genus, Cytomegalovirus (CMV), Dengue viruses (DEN-1, DEN-2, DEN-3 and DEN-4), *Dientamoeba fragilis*, Ebolavirus (EBOV), *Echinococcus* genus, *Ehrlichia chaffeensis, Ehrlichia ewingii, Ehrlichia* genus, *Entamoeba histolytica, Enterococcus* genus, Enterovirus genus, Enteroviruses, mainly Coxsackie A virus and Enterovirus 71 (EV71), *Epidermophyton* spp, Epstein-Barr Virus (EBV), *Escherichia coli* O157:H7, O111 and 0104:H4, *Fasciola hepatica* and *Fasciola gigantica*, FFI prion, Filarioidea superfamily, Flaviviruses, *Francisella tularensis, Fusobacterium* genus, *Geotrichum candidum, Giardia intestinalis, Gnathostoma* spp, GSS prion, Guanarito virus, *Haemophilus ducreyi, Haemophilus influenzae, Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Japanese encephalitis virus, JC virus, Junin virus, Kingella kingae, *Klebsiella granulomatis*, Kuru prion, Lassa virus, *Legionella pneumophila, Leishmania* genus, *Leptospira* genus, *Listeria monocytogenes*, Lymphocytic choriomeningitis virus (LCMV), Machupo virus, *Malassezia* spp, Marburg virus, Measles virus, *Metagonimus yokagawai*, Microsporidia phylum, Molluscum contagiosum virus (MCV), Mumps virus, *Mycobacterium leprae* and *Mycobacterium lepromatosis, Mycobacterium tuberculosis, Mycobacterium ulcerans, Mycoplasma pneumoniae, Naegleria fowleri, Necator americanus, Neisseria gonorrhoeae, Neisseria meningitidis, Nocardia asteroides, Nocardia* spp, *Onchocerca volvulus, Orientia tsutsugamushi*, Orthomyxoviridae family (Influenza), *Paracoccidioides brasiliensis, Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari, Rickettsia* genus, *Rickettsia prowazekii, Rickettsia rickettsii, Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii, Staphylococcus* genus, *Staphylococcus* genus, *Streptococcus agalactiae, Streptococcus pneumoniae, Streptococcus pyogenes, Strongyloides stercoralis, Taenia* genus, *Taenia solium*, Tick-borne encephalitis virus (TBEV), *Toxocara canis* or *Toxocara cati, Toxoplasma gondii, Treponema pallidum, Trichinella spiralis, Trichomonas vaginalis, Trichophyton* spp, *Trichuris trichiura, Trypanosoma brucei, Trypanosoma cruzi, Ureaplasma urealyticum*, Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica, Yersinia pestis*, and *Yersinia pseudotuberculosis*.

In this context particularly preferred are antigens from the pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus.

Furthermore, the pathogenic antigen (antigen derived from a pathogen associated with infectious disease) may be preferably selected from the following antigens: Outer membrane protein A OmpA, biofilm associated protein Bap, transport protein MucK (*Acinetobacter baumannii, Acinetobacter* infections)); variable surface glycoprotein VSG, microtubule-associated protein MAPP15, trans-sialidase TSA (*Trypanosoma brucei*, African sleeping sickness (African trypanosomiasis)); HIV p24 antigen, HIV envelope proteins (Gp120, Gp41, Gp160), polyprotein GAG, negative factor protein Nef, trans-activator of transcription Tat (HIV (Human immunodeficiency virus), AIDS (Acquired immunodeficiency syndrome)); galactose-inhabitable adherence protein GIAP, 29 kDa antigen Eh29, Gal/GalNAc lectin, protein CRT, 125 kDa immunodominant antigen, protein M17, adhesin ADH112, protein STIRP (*Entamoeba histolytica*, Amoebiasis); Major surface proteins 1-5 (MSP1a, MSP1b, MSP2, MSP3, MSP4, MSPS), type IV secretion system proteins (VirB2, VirB7, VirB11, VirD4) (*Anaplasma* genus, Anaplasmosis); protective Antigen PA, edema factor EF, lethal factor LF, the S-layer homology proteins SLH (*Bacillus anthracis*, Anthrax); acranolysin, phospholipase D, collagen-binding protein CbpA (*Arcanobacterium haemolyticum, Arcanobacterium haemolyticum* infection); nucleocapsid protein NP, glycoprotein precursor GPC, glycoprotein GP1, glycoprotein GP2 (Junin virus, Argentine hemorrhagic fever); chitin-protein layer proteins, 14 kDa surface antigen A14, major sperm protein MSP, MSP polymerization-organizing protein MPOP, MSP fiber protein 2 MFP2, MSP polymerization-activating kinase MPAK, ABA-1-like protein ALB, protein ABA-1, cuticulin CUT-1 (*Ascaris lumbricoides*, Ascariasis); 41 kDa allergen Asp v13, allergen Asp f3, major conidial surface protein rodlet A, protease Pep1p, GPI-anchored protein Gel1p, GPI-anchored protein Crf1p (*Aspergillus* genus, Aspergillosis); family VP26 protein, VP29 protein (Astroviridae, Astrovirus infection); Rhoptry-associated protein 1 RAP-1, merozoite surface antigens MSA-1, MSA-2 (a1, a2, b, c), 12D3, 1105, 21B4, P29, variant erythrocyte surface antigen VESA1, Apical Membrane Antigen 1 AMA-1 (*Babesia* genus, Babesiosis); hemolysin, enterotoxin C, PXO1-51, glycolate oxidase, ABC-transporter, penicillin-binding protein, zinc transporter family protein, pseudouridine synthase Rsu, plasmid replication protein RepX, oligoendopeptidase F, prophage membrane protein, protein HemK, flagellar antigen H, 28.5-kDa cell surface antigen (*Bacillus cereus, Bacillus cereus* infection); large T antigen LT, small T antigen, capsid protein VP1, capsid protein VP2 (BK virus, BK virus infection); 29 kDa-protein, caspase-3-like antigens, glycoproteins (*Blastocystis hominis, Blastocystis hominis* infection); yeast surface adhesin WI-1 (*Blastomyces dermatitidis*, Blastomycosis); nucleoprotein N, polymerase L, matrix protein Z, glycoprotein GP (Machupo virus, Bolivian hemorrhagic fever); outer surface protein A OspA, outer surface protein OspB, outer surface protein OspC, decorin binding protein A DbpA, decorin binding protein B DbpB, flagellar filament 41 kDa core protein Fla, basic membrane protein A precursor BmpA (Immunodominant antigen P39), outer surface 22 kDa lipoprotein precursor (antigen IPLA7), variable surface lipoprotein vlsE (*Borrelia* genus, *Borrelia* infection); Botulinum neurotoxins BoNT/A1, BoNT/A2, BoNT/A3, BoNT/B, BoNT/C, BoNT/D, BoNT/E, BoNT/F, BoNT/G, recombinant botulinum toxin F Hc domain FHc (*Clostridium botulinum*, Botulism (and Infant botulism)); nucleocapsid, glycoprotein precursor (Sabia virus, Brazilian hemorrhagic fever); copper/Zinc superoxide dismutase SodC, bacterioferritin Bfr, 50S ribosomal protein Rp1L, OmpA-like transmembrane domain-containing protein Omp31, immunogenic 39-kDa protein M5 P39, zinc ABC transporter periplasmic zinc-binding protein znuA, periplasmic immunogenic protein Bp26, 30S ribosomal protein S12 RpsL, glyceraldehyde-3-phosphate dehydrogenase Gap, 25 kDa outer-membrane immunogenic protein precursor Omp25, invasion protein B IalB, trigger factor Tig, molecular chaperone DnaK, putative peptidyl-prolyl cis-trans isomerase SurA, lipoprotein Omp19, outer membrane protein MotY Omp16, conserved outer membrane protein D15, malate dehydrogenase Mdh, component of the Type-IV secretion system (T4SS) VirJ, lipoprotein of unknown function BAB1_0187 (*Brucella* genus, Brucellosis); members of the ABC transporter family (LolC, OppA, and PotF), putative lipoprotein releasing system transmembrane protein LolC/E, flagellin FliC, *Burkholderia* intracellular motility A BimA, bacterial Elongation factor-Tu EF-Tu, 17 kDa OmpA-like protein, boaA coding protein, boaB coding protein (*Burkholderia cepacia* and other *Burkholderia* species, *Burkholderia* infection); mycolyl-transferase Ag85A, heat-shock protein Hsp65, protein TB10.4, 19 kDa antigen, protein PstS3, heat-shock protein Hsp70 (*Mycobacterium ulcerans*, Buruli ulcer); norovirus major and minor viral capsid proteins VP1 and VP2, genome polyprotein, Sapoviurus capsid protein VP1, protein Vp3, genome polyprotein (Caliciviridae family, Calicivirus infection (Norovirus and Sapovirus)); major outer membrane protein PorA, flagellin FlaA, surface antigen CjaA, fibronectin binding protein CadF, aspartate/glutamate-binding ABC transporter protein Peb1A, protein FspA1, protein FspA2 (*Campylobacter* genus, Campylobacteriosis); glycolytic enzyme enolase, secreted aspartyl proteinases SAP1-10, glycophosphatidylinositol (GPI)-linked cell wall protein, protein Hyr1, complement receptor 3-related protein CR3-RP, adhesin Als3p, heat shock protein 90 kDa hsp90, cell surface hydrophobicity protein CSH (usually *Candida albicans* and other *Candida* species, Candidiasis); 17-kDa antigen, protein P26, trimeric autotransporter adhesins TAAs, *Bartonella* adhesin A BadA, variably expressed outer-membrane proteins Vomps, protein Pap3, protein HbpA, envelope-associated protease HtrA, protein OMP89, protein GroEL, protein La1B, protein OMP43, dihydrolipoamide succinyltransferase SucB (*Bartonella henselae*, Cat-scratch disease); amastigote surface protein-2, amastigote-specific surface protein SSP4, cruzipain, trans-sialidase TS, trypomastigote surface glycoprotein TSA-1, complement regulatory protein CRP-10, protein G4, protein G2, paraxonemal rod protein PAR2, paraflagellar rod component Par1, mucin-Associated Surface Proteins MPSP (*Trypanosoma cruzi*, Chagas Disease (American trypanosomiasis)); envelope glycoproteins (gB, gC, gE, gH, gI, gK, gL) (Varicella zoster virus (VZV), Chickenpox); major outer membrane protein MOMP, probable outer membrane protein PMPC, outer membrane complex protein B OmcB, heat shock proteins Hsp60 HSP10, protein IncA, proteins from the type III secretion system, ribonucleotide reductase small chain protein NrdB, plasmid protein Pgp3, chlamydial outer protein N CopN, antigen CT521, antigen CT425, antigen CT043, antigen TC0052, antigen TC0189, antigen TC0582, antigen TC0660, antigen TC0726, antigen TC0816, antigen TC0828 (*Chlamydia trachomatis*, Chlamydia); low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 Omp2, polymorphic membrane protein family (Pmp1, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20, Pmp21) (*Chlamydophila pneumoniae*, *Chlamydophila pneumoniae* infection); cholera toxin B CTB, toxin coregulated pilin A TcpA, toxin coregulated pilin TcpF, toxin co-regulated pilus biosynthesis protein F TcpF, cholera enterotoxin subunit A, cholera enterotoxin subunit B, Heat-stable enterotoxin ST, mannose-sensitive hemagglutinin MSHA, outer membrane protein U Porin ompU, Poring B protein, polymorphic membrane protein-D (*Vibrio cholerae*, Cholera); propionyl-CoA carboxylase PCC, 14-3-3 protein, prohibitin, cysteine proteases, glutathione transferases, gelsolin, cathepsin L proteinase CatL, Tegumental Protein 20.8 kDa TP20.8, tegumental protein 31.8 kDa TP31.8, lysophosphatidic acid phosphatase LPAP, (*Clonorchis sinensis*, Clonorchiasis); surface layer proteins SLPs, glutamate dehydrogenase antigen GDH, toxin A, toxin B, cysteine protease Cwp84, cysteine protease Cwp13, cysteine protease Cwp19, Cell Wall Protein CwpV, flagellar protein FliC, flagellar protein FliD (*Clostridium difficile*, *Clostridium difficile* infection); rhinoviruses: capsid proteins VP1, VP2, VP3, VP4; coronaviruses: spike proteins S, envelope proteins E, membrane proteins M, nucleocapsid proteins N (usually rhinoviruses and coronaviruses, Common cold (Acute viral rhinopharyngitis; Acute coryza)); prion protein Prp (CJD prion, Creutzfeldt-Jakob disease (CJD)); envelope protein Gc, envelope protein Gn, nucleocapsid proteins (Crimean-Congo hemorrhagic fever virus, Crimean-Congo hemorrhagic fever (CCHF)); virulence-associated DEAD-box RNA helicase VAD1, galactoxylomannan-protein GalXM, glucuronoxylomannan GXM, mannoprotein MP (*Cryptococcus neoformans*, Cryptococcosis); acidic ribosomal protein P2 CpP2, mucin antigens Muc1, Muc2, Muc3 Muc4, Muc5, Muc6, Muc7, surface adherence protein CP20, surface adherence protein CP23, surface protein CP12, surface protein CP21, surface protein CP40, surface protein CP60, surface protein CP15, surface-associated glycopeptides gp40, surface-associated glycopeptides gp15, oocyst wall protein AB, profilin PRF, apyrase (*Cryptosporidium* genus, Cryptosporidiosis); fatty acid and retinol binding protein-1 FAR-1, tissue inhibitor of metalloproteinase TIMP (TMP), cysteine proteinase ACEY-1, cysteine proteinase ACCP-1, surface antigen Ac-16, secreted protein 2 ASP-2, metalloprotease 1 MTP-1, aspartyl protease inhibitor API-1, surface-associated antigen SAA-1, adult-specific secreted factor Xa serine protease inhibitor anticoagulant AP, cathepsin D-like aspartic protease ARR-1 (usually *Ancylostoma braziliense*; multiple other parasites, Cutaneous larva migrans (CLM)); cathepsin L-like proteases, 53/25-kDa antigen, 8 kDa family members, cysticercus protein with a marginal trypsin-like activity TsAg5, oncosphere protein TSOL18, oncosphere protein TSOL45-1A, lactate dehydrogenase A LDHA, lactate dehydrogenase B LDHB (*Taenia solium*, Cysticercosis); pp65 antigen, membrane protein pp15, capsid-proximal tegument protein pp150, protein M45, DNA polymerase UL54, helicase UL105, glycoprotein gM, glycoprotein gN, glcoprotein H, glycoprotein B gB, protein UL83, protein UL94, protein UL99 (Cytomegalovirus (CMV), Cytomegalovirus infection); capsid protein C, pre-membrane protein prM, membrane protein M, envelope protein E (domain I, domain II, domain II), protein NS1, protein NS2A, protein NS2B, protein NS3, protein NS4A, protein 2K, protein NS4B, protein NS5 (Dengue viruses (DEN-1, DEN-2, DEN-3 and DEN-4)-Flaviviruses, Dengue fever); 39 kDa protein (*Dientamoeba fragilis*, Dientamoebiasis); diphtheria toxin precursor Tox, diphteria toxin DT, pilin-specific sortase SrtA, shaft pilin protein SpaA, tip pilin protein SpaC, minor pilin protein SpaB, surface-associated protein DIP1281 (*Corynebacterium diphtheriae*, Diphtheria); glycoprotein GP, nucleoprotein NP, minor matrix protein VP24, major matrix protein VP40, transcription activator VP30, polymerase cofactor VP35, RNA polymerase L (Ebolavirus (EBOV), Ebola hemorrhagic fever); prion protein (vCJD prion, Variant Creutzfeldt-Jakob disease (vCJD, nvCJD)); UvrABC system protein B, protein Flp1, protein Flp2, protein Flp3, protein TadA, hemoglobin receptor HgbA, outer membrane protein TdhA, protein CpsRA, regulator CpxR, protein SapA, 18 kDa antigen, outer membrane protein NcaA, protein LspA, protein LspA1, protein LspA2, protein LspB, outer membrane component DsrA, lectin DltA, lipoprotein Hlp, major outer membrane protein OMP, outer membrane protein OmpA2 (*Haemophilus ducreyi*, Chancroid); aspartyl protease 1 Pep1, phospholipase B PLB, alpha-mannosidase 1 AMN1, glucanosyltransferase GEL1, urease URE, peroxisomal matrix protein Pmp1, proline-rich antigen Pra, humal T-cell reactive protein TcrP (*Coccidioides immitis* and *Coccidioides posadasii*, Coccidioidomycosis); allergen Tri r 2, heat shock protein 60 Hsp60, fungal actin Act, antigen Tri r2, antigen Tri r4, antigen Tri t1, protein IV, glycerol-3-phosphate dehydrogenase Gpd1, osmosensor HwSho1A, osmosensor HwSho1B, histidine kinase HwHhk7B, allergen Mala s 1, allergen Mala s 11, thioredoxin Trx Mala s 13, allergen Mala f, allergen Mala s (usually *Trichophyton* spp, *Epidermophyton* spp., *Malassezia* spp., *Hortaea werneckii*, Dermatophytosis); protein EG95, protein EG10, protein EG18, protein EgA31, protein EM18, antigen EPC1, antigen B, antigen 5, protein P29, protein 14-3-3, 8-kDa protein, myophilin, heat shock protein 20 HSP20, glycoprotein GP-89, fatty acid binding protein FAPB (*Echinococcus* genus, Echinococcosis); major surface protein 2 MSP2, major surface protein 4 MSP4, MSP variant SGV1, MSP variant SGV2, outer membrane protein OMP, outer membraned protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia* genus, Ehrlichiosis); secreted antigen SagA, sagA-like proteins Sa1A and Sa1B, collagen adhesin Scm, surface proteins Fms1 (EbpA(fm), Fms5 (EbpB(fm), Fms9 (EpbC(fm) and Fms10, protein EbpC(fm), 96 kDa immunoprotective glycoprotein G1 (*Enterococcus* genus, *Enterococcus* infection); genome polyprotein, polymerase 3D, viral capsid protein VP1, viral capsid protein VP2, viral capsid protein VP3, viral capsid protein VP4, protease 2A, protease 3C (Enterovirus genus, Enterovirus infection); outer membrane proteins OM, 600 kDa outer membrane protein, cell surface antigen OmpA, cell surface antigen OmpB (sca5), 134 kDa outer membrane protein, 31 kDa outer membrane protein, 29.5 kDa outer membrane protein, cell surface protein SCA4, cell surface protein Add (RP827), cell surface protein Adr2 (RP828), cell surface protein SCA1, Invasion protein invA, cell division protein fts, secretion proteins sec 0family, virulence proteins virB, tlyA, tlyC, parvulin-like protein Plp, preprotein translocase SecA, 120-kDa surface protein antigen SPA, 138 kD complex antigen, major 100-kD protein (protein I), intracytoplasmic protein D, protective surface protein antigen SPA (*Rickettsia prowazekii*, Epidemic typhus); Epstein-Barr nuclear antigens (EBNA-1, EBNA-2, EBNA-3A, EBNA-3B, EBNA-3C, EBNA-leader protein (EBNA-LP)), latent membrane proteins (LMP-1, LMP-2A, LMP-2B), early antigen EBV-EA, membrane antigen EBV-MA, viral capsid antigen EBV-VCA, alkaline nuclease EBV-AN, glycoprotein H, glycoprotein gp350, glycoprotein gp110, glycoprotein gp42, glycoprotein gHgL, glycoprotein gB (Epstein-Barr Virus (EBV), Epstein-Barr Virus Infectious Mononucleosis); capsid protein VP2, capsid protein VP1, major protein NS1 (Parvovirus B19, Erythema infectiosum (Fifth disease)); pp65 antigen, glycoprotein 105, major capsid protein, envelope glycoprotein H, protein U51 (Human herpesvirus 6 (HHV-6) and Human herpesvirus 7 (HHV-7), Exanthem subitum); thioredoxin-glutathione reductase TGR, cathepsins L1 and L2, Kunitz-type protein KTM, leucine aminopeptidase LAP, cysteine proteinase Fas2, saposin-like protein-2 SAP-2, thioredoxin peroxidases TPx, Prx-1, Prx-2, cathepsin 1 cysteine proteinase CL3, protease cathepsin L CL1, phosphoglycerate kinase PGK, 27-kDa secretory protein, 60 kDa protein HSP35alpha, glutathione transferase GST, 28.5 kDa tegumental antigen 28.5 kDa TA, cathepsin B3 protease CatB3, Type I cystatin stefin-1, cathepsin L5, cathepsin L1g and cathepsin B, fatty acid binding protein FABP, leucine aminopeptidases LAP (*Fasciola hepatica* and *Fasciola gigantica*, Fasciolosis); prion protein (FFI prion, Fatal familial insomnia (FFI)); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, secreted larval acidic proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 (Filarioidea superfamily, Filariasis); phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, Fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm (*Clostridium perfringens*, Food poisoning by *Clostridium perfringens*); leukotoxin lktA, adhesion FadA, outer membrane protein RadD, high-molecular weight arginine-binding protein (*Fusobacterium* genus, *Fusobacterium* infection); phospholipase C PLC, heat-labile enterotoxin B, Iota toxin component Ib, protein CPE1281, pyruvate ferredoxin oxidoreductase, elongation factor G EF-G, perfringolysin O Pfo, glyceraldehyde-3-phosphate dehydrogenase GapC, fructose-bisphosphate aldolase Alf2, *Clostridium perfringens* enterotoxin CPE, alpha toxin AT, alpha toxoid ATd, epsilon-toxoid ETd, protein HP, large cytotoxin TpeL, endo-beta-N-acetylglucosaminidase Naglu, phosphoglyceromutase Pgm (usually *Clostridium perfringens*; other *Clostridium* species, Gas gangrene (Clostridial myonecrosis)); lipase A, lipase B, peroxidase Dec1 (*Geotrichum candidum*, Geotrichosis); prion protein (GSS prion, Gerstmann-Sträussler-Scheinker syndrome (GSS)); cyst wall proteins CWP1, CWP2, CWP3, variant surface protein VSP, VSP1, VSP2, VSP3, VSP4, VSP5, VSP6, 56 kDa antigen, pyruvate ferredoxin oxidoreductase PFOR, alcohol dehydrogenase E ADHE, alpha-giardin, alpha8-giardin, alpha1-giardin, beta-giardin, cystein proteases, glutathione-S-transferase GST, arginine deiminase ADI, fructose-1,6-bisphosphat aldolase FBA, *Giardia* trophozoite antigens GTA (GTA1, GTA2), ornithine carboxyl transferase OCT, striated fiber-asseblin-like protein SALP, uridine phosphoryl-like protein UPL, alpha-tubulin, beta-tubulin (*Giardia intestinalis*, Giardiasis); members of the ABC transporter family (LolC, OppA, and PotF), putative lipoprotein releasing system transmembrane protein LolC/E, flagellin FliC, *Burkholderia* intracellular motility A BimA, bacterial Elongation factor-Tu EF-Tu, 17 kDa OmpA-like protein, boaA coding protein (*Burkholderia mallei*, Glanders); cyclophilin CyP, 24 kDa third-stage larvae protein GS24, excretion-secretion products ESPs (40, 80, 120 and 208 kDa) (*Gnathostoma spinigerum* and *Gnathostoma hispidum*, Gnathostomiasis); pilin proteins, minor pilin-associated subunit pilC, major pilin subunit and variants pilE, pilS, phase variation protein porA, Porin B PorB, protein TraD, Neisserial outer membrane antigen H.8, 70 kDa antigen, major outer membrane protein PI, outer membrane proteins P1A and P1B, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR (*Neisseria gonorrhoeae*, Gonorrhea); outer membrane protein A OmpA, outer membrane protein C OmpC, outer membrane protein K17 OmpK17 (*Klebsiella granulomatis*, Granuloma inguinale (Donovanosis)); fibronectin-binding protein Sfb, fibronectin/fibrinogen-binding protein FBP54, fibronectin-binding protein FbaA, M protein type 1 Emm1, M protein type 6 Emm6, immunoglobulin-binding protein 35 Sib35, Surface protein R28 Spr28, superoxide dismutase SOD, C5a peptidase ScpA, antigen I/II AgI/II, adhesin AspA, G-related alpha2-macroglobulin-binding protein GRAB, surface fibrillar protein M5 (*Streptococcus pyogenes*, Group A streptococcal infection); C protein β antigen, arginine deiminase proteins, adhesin BibA, 105 kDA protein BPS, surface antigens c, surface antigens R, surface antigens X, trypsin-resistant protein R1, trypsin-resistant protein R3, trypsin-resistant protein R4, surface immunogenic protein Sip, surface protein Rib, Leucine-rich repeats protein LrrG, serine-rich repeat protein Srr-2, C protein alpha-antigen Bca, Beta antigen Bag, surface antigen Epsilon, alpha-like protein ALP1, alpha-like protein ALP5 surface antigen delta, alpha-like protein ALP2, alpha-like protein ALP3, alpha-like protein ALP4, Cbeta protein Bac (*Streptococcus agalactiae*, Group B streptococcal infection); transferrin-binding protein 2 Tbp2, phosphatase P4, outer membrane protein P6, peptidoglycan-associated lipoprotein Pal, protein D, protein E, adherence and penetration protein Hap, outer membrane protein 26 Omp26, outer membrane protein P5 (Fimbrin), outer membrane protein D15, outer membrane protein OmpP2, 5'-nucleotidase NucA, outer membrane protein P1, outer membrane protein P2, outer membrane lipoprotein Pcp, Lipoprotein E, outer membrane protein P4, fuculokinase FucK, [Cu,Zn]-superoxide dismutase SodC, protease HtrA, protein 0145, alpha-galactosylceramide (*Haemophilus influenzae, Haemophilus influenzae* infection); polymerase 3D, viral capsid protein VP1, viral capsid protein VP2, viral capsid protein VP3, viral capsid protein VP4, protease 2A, protease 3C (Enteroviruses, mainly Coxsackie A virus and Enterovirus 71 (EV71), Hand, foot and mouth disease (HFMD)); RNA polymerase L, protein L, glycoprotein Gn, glycoprotein Gc, nucleocapsid protein S, envelope glycoprotein G1, nucleoprotein NP, protein N, polyprotein M (Sin Nombre virus, Hantavirus, Hantavirus Pulmonary Syndrome (HPS)); heat shock protein HspA, heat shock protein HspB, citrate synthase GltA, protein UreB, heat shock protein Hsp60, neutrophil-activating protein NAP, catalase KatA, vacuolating cytotoxin VacA, urease alpha UreA, urease beta Ureb, protein Cpn10, protein groES, heat shock protein Hsp10, protein MopB, cytotoxicity-associated 10 kDa protein CAG, 36 kDa antigen, beta-lactamase HcpA, Beta-lactamase HcpB (*Helicobacter pylori, Helicobacter pylori* infection); integral membrane proteins, aggregation-prone proteins, 0-antigen, toxin-antigens Stx2B, toxin-antigen Stx1B, adhesion-antigen fragment Int28, protein EspA, protein EspB, Intimin, protein Tir, protein IntC300, protein Eae (*Escherichia coli* O157:H7, O111 and 0104:H4, Hemolytic-uremic syndrome (HUS)); RNA polymerase L, protein L, glycoprotein Gn, glycoprotein Gc, nucleocapsid protein S, envelope glycoprotein G1, nucleoprotein NP, protein N, polyprotein M (Bunyaviridae family, Hemorrhagic fever with renal syndrome (HFRS)); glycoprotein G, matrix protein M, nucleoprotein N, fusion protein F, polymerase L, protein W, proteinC, phosphoprotein p, non-structural protein V (Henipavirus (Hendra virus Nipah virus), Henipavirus infections); polyprotein, glycoproten Gp2, hepatitis A surface antigen HBAg, protein 2A, virus protein VP1, virus protein VP2, virus protein VP3, virus protein VP4, protein P1B, protein P2A, protein P3AB, protein P3D (Hepatitis A Virus, Hepatitis A); hepatitis B surface antigen HBsAg, Hepatitis B core antigen HbcAg, polymerase, protein Hbx, preS2 middle surface protein, surface protein L, large S protein, virus protein VP1, virus protein VP2, virus protein VP3, virus protein VP4 (Hepatitis B Virus (HBV), Hepatitis B); envelope glycoprotein E1 gp32 gp35, envelope glycoprotein E2 NS1 gp68 gp70, capsid protein C, core protein Core, polyprotein, virus protein VP1, virus protein VP2, virus protein VP3, virus protein VP4, antigen G, protein NS3, protein NS5A, (Hepatitis C Virus, Hepatitis C); virus protein VP1, virus protein VP2, virus protein VP3, virus protein VP4, large hepatitis delta antigen, small hepatitis delta antigen (Hepatitis D Virus, Hepatitis D); virus protein VP1, virus protein VP2, virus protein VP3, virus protein VP4, capsid protein E2 (Hepatitis E Virus, Hepatitis E); glycoprotein L UL1, uracil-DNA glycosylase UL2, protein UL3, protein UL4, DNA replication protein UL5, portal protein UL6, virion maturation protein UL7, DNA helicase UL8, replication origin-binding protein UL9, glycoprotein M UL10, protein UL11, alkaline exonuclease UL12, serine-threonine protein kinase UL13, tegument protein UL14, terminase UL15, tegument protein UL16, protein UL17, capsid protein VP23 UL18, major capsid protein VP5 UL19, membrane protein UL20, tegument protein UL21, Glycoprotein H (UL22), Thymidine Kinase UL23, protein UL24, protein UL25, capsid protein P40 (UL26, VP24, VP22A), glycoprotein B (UL27), ICP18.5 protein (UL28), major DNA-binding protein ICP8 (UL29), DNA polymerase UL30, nuclear matrix protein UL31, envelope glycoprotein UL32, protein UL33, inner nuclear membrane protein UL34, capsid protein VP26 (UL35), large tegument protein UL36, capsid assembly protein UL37, VP19C protein (UL38), ribonucleotide reductase (Large subunit) UL39, ribonucleotide reductase (Small subunit) UL40, tegument protein/virion host shutoff VHS protein (UL41), DNA polymerase processivity factor UL42, membrane protein UL43, glycoprotein C (UL44), membrane protein UL45, tegument proteins VP11/12 (UL46), tegument protein VP13/14 (UL47), virion maturation protein VP16 (UL48, Alpha-TIF), envelope protein UL49, dUTP diphosphatase UL50, tegument protein UL51, DNA helicase/primase complex protein UL52, glycoprotein K (UL53), transcriptional regulation protein I E63 (ICP27, UL54), protein UL55, protein UL56, viral replication protein ICP22 (1E68, US1), protein US2, serine/threonine-protein kinase US3, glycoprotein G (US4), glycoprotein J (US5), glycoprotein D (US6), glycoprotein I (US7), glycoprotein E (US8), tegument protein US9, capsid/tegument protein US10, Vmw21 protein (US11), ICP47 protein (IE12, US12), major transcriptional activator ICP4 (1E175, RS1), E3 ubiquitin ligase ICP0 (IE110), latency-related protein 1 LRP1, latency-related protein 2 LRP2, neurovirulence factor RL1 (ICP34.5), latency-associated transcript LAT (Herpes simplex virus 1 and 2 (HSV-1 and HSV-2), Herpes simplex); heat shock protein Hsp60, cell surface protein H1C, dipeptidyl peptidase type IV DppIV, M antigen, 70 kDa protein, 17 kDa histone-like protein (*Histoplasma capsulatum*, Histoplasmosis); fatty acid and retinol binding protein-1 FAR-1, tissue inhibitor of metalloproteinase TIMP (TMP), cysteine proteinase ACEY-1, cysteine proteinase ACCP-1, surface antigen Ac-16, secreted protein 2 ASP-2, metalloprotease 1 MTP-1, aspartyl protease inhibitor API-1, surface-associated antigen SAA-1, surface-associated antigen SAA-2, adult-specific secreted factor Xa, serine protease inhibitor anticoagulant AP, cathepsin D-like aspartic protease ARR-1, glutathione S-transferase GST, aspartic protease APR-1, acetylcholinesterase AChE (*Ancylostoma duodenale* and *Necator americanus*, Hookworm infection); protein NS1, protein NP1, protein VP1, protein VP2, protein VP3 (Human bocavirus (HBoV), Human bocavirus infection); major surface protein 2 MSP2, major surface protein 4 MSP4, MSP variant SGV1, MSP variant SGV2, outer membrane protein OMP, outer membraned protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia ewingii*, Human ewingii ehrlichiosis); major surface proteins 1-5 (MSP1a, MSP1b, MSP2, MSP3, MSP4, MSPS), type IV secretion system proteins VirB2, VirB7, VirB11, VirD4 (*Anaplasma phagocytophilum*, Human granulocytic anaplasmosis (HGA)); protein NS1, small hydrophobic protein NS2, SH protein, fusion protein F, glycoprotein G, matrix protein M, matrix protein M2-1, matrix protein M2-2, phosphoprotein P, nucleoprotein N, polymerase L (Human metapneumovirus (hMPV), Human metapneumovirus infection); major surface protein 2 MSP2, major surface protein 4 MSP4, MSP variant SGV1, MSP variant SGV2, outer membrane protein OMP, outer membraned protein 19 OMP-19, major antigenic protein MAP1, major antigenic protein MAP1-2, major antigenic protein MAP1B, major antigenic protein MAP1-3, Erum2510 coding protein, protein GroEL, protein GroES, 30-kDA major outer membrane proteins, GE 100-kDa protein, GE 130-kDa protein, GE 160-kDa protein (*Ehrlichia chaffeensis*, Human monocytic ehrlichiosis); replication protein E1, regulatory protein E2, protein E3, protein E4, protein E5, protein E6, protein E7, protein E8, major capsid protein L1, minor capsid protein L2 (Human papillomavirus (HPV), Human papillomavirus (HPV) infection); fusion protein F, hemagglutinin-neuramidase HN, glycoprotein G, matrix protein M, phosphoprotein P, nucleoprotein N, polymerase L (Human parainfluenza viruses (HPIV), Human parainfluenza virus infection); Hemagglutinin (HA), Neuraminidase (NA), Nucleoprotein (NP), M1 protein, M2 protein, NS1 protein, NS2 protein (NEP protein: nuclear export protein), PA protein, PB1 protein (polymerase basic 1 protein), PB1-F2 protein and PB2 protein (Orthomyxoviridae family, Influenza virus (flu)); genome polyprotein, protein E, protein M, capsid protein C (Japanese encephalitis virus, Japanese encephalitis); RTX toxin, type IV pili, major pilus subunit PilA, regulatory transcription factors PilS and PilR, protein sigma54, outer membrane proteins (Kingella kingae, Kingella kingae infection); prion protein (Kuru prion, Kuru); nucleoprotein N, polymerase L, matrix protein Z, glycoprotein GP (Lassa virus, Lassa fever); peptidoglycan-associated lipoprotein PAL, 60 kDa chaperonin Cpn60 (groEL, HspB), type IV pilin PilE, outer membrane protein MIP, major outer membrane protein MompS, zinc metalloproteinase MSP (*Legionella pneumophila*, Legionellosis (Legionnaires' disease, Pontiac fever)); P4 nuclease, protein WD, ribonucleotide reductase M2, surface membrane glycoprotein Pg46, cysteine proteinase CP, glucose-regulated protein 78 GRP-78, stage-specific S antigen-like protein A2, ATPase F1, beta-tubulin, heat shock protein 70 Hsp70, KMP-11, glycoprotein GP63, protein BT1, nucleoside hydrolase NH, cell surface protein B1, ribosomal protein P1-like protein P1, sterol 24-c-methyltransferase SMT, LACK protein, histone H1, SPB1 protein, thiol specific antioxidant TSA, protein antigen ST11, signal peptidase SP, histone H2B, surface antigen PSA-2, cystein proteinase b Cpb (*Leishmania* genus, Leishmaniasis); major membrane protein I, serine-rich antigen-45 kDa, 10 kDa caperonin GroES, HSP kDa antigen, amino-oxononanoate synthase AONS, protein recombinase A RecA, Acetyl-/propionyl-coenzyme A carboxylase alpha, alanine racemase, 60 kDa chaperonin 2, ESAT-6-like protein EcxB (L-ESAT-6), protein Lsr2, protein ML0276, Heparin-binding hemagglutinin HBHA, heat-shock protein 65 Hsp65, mycP1 or ML0041 coding protein, htrA2 or ML0176 coding protein, htrA4 or ML2659 coding protein, gcp or ML0379 coding protein, clpC or ML0235 coding protein (*Mycobacterium leprae* and *Mycobacterium* lepromatosis, Leprosy); outer membrane protein LipL32, membrane protein LIC10258, membrane protein LP30, membrane protein LIC12238, Ompa-like protein Lsa66, surface protein LigA, surface protein LigB, major outer membrane protein OmpL1, outer membrane protein LipL41, protein LigAni, surface protein LcpA, adhesion protein LipL53, outer membrane protein UpL32, surface protein Lsa63, flagellin FlaB 1, membrane lipoprotein LipL21, membrane protein pL40, leptospiral surface adhesin Lsa27, outer membrane protein OmpL36, outer membrane protein OmpL37, outer membrane protein OmpL47, outer membrane protein OmpL54, acyltransferase LpxA (Leptospira genus, Leptospirosis); listeriolysin O precursor Hly (LLO), invasion-associated protein Iap (P60), Listeriolysin regulatory protein PrfA, Zinc metalloproteinase Mpl, Phosphatidylinositol-specific phospholipase C PLC (PlcA, PlcB), 0-acetyltransferase Oat, ABC-transporter permease Im.G_1771, adhesion protein LAP, LAP receptor Hsp60, adhesin LapB, haemolysin listeriolysin O LLO, protein ActA, Internalin A In1A, protein In1B (*Listeria monocytogenes*, Listeriosis); outer surface protein A OspA, outer surface protein OspB, outer surface protein OspC, decorin binding protein A DbpA, decorin binding protein B DbpB, flagellar filament 41 kDa core protein Fla, basic membrane protein A BmpA (Immunodominant antigen P39), outer surface 22 kDa lipoprotein precursor (antigen IPLA7), variable surface lipoprotein vlsE (usually *Borrelia burgdorferi* and other *Borrelia* species, Lyme disease (Lyme borreliosis)); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, protein Cox-2 (*Wuchereria bancrofti* and *Brugia malayi*, Lymphatic filariasis (Elephantiasis)); glycoprotein GP, matrix protein Z, polymerase L, nucleoprotein N (Lymphocytic choriomeningitis virus (LCMV), Lymphocytic choriomeningitis); thrombospondin-related anonymous protein TRAP, SSP2 Sporozoite surface protein 2, apical membrane antigen 1 AMA1, rhoptry membrane antigen RMA1, acidic basic repeat antigen ABRA, cell-traversal protein PF, protein Pvs25, merozoite surface protein 1 MSP-1, merozoite surface protein 2 MSP-2, ring-infected erythrocyte surface antigen RESALiver stage antigen 3 LSA-3, protein Eba-175, serine repeat antigen 5 SERA-5, circumsporozoite protein CS, merozoite surface protein 3 MSP3, merozoite surface protein 8 MSPS, enolase PF10, hepatocyte erythrocyte protein 17 kDa HEP17, erythrocyte membrane protein 1 EMP1, protein Kbetamerozoite surface protein 4/5 MSP 4/5, heat shock protein Hsp90, glutamate-rich protein GLURP, merozoite surface protein 4 MSP-4, protein STARP, circumsporozoite protein-related antigen precursor CRA (*Plasmodium* genus, Malaria); nucleoprotein N, membrane-associated protein VP24, minor nucleoprotein VP30, polymerase cofactor VP35, polymerase L, matrix protein VP40, envelope glycoprotein GP (Marburg virus, Marburg hemorrhagic fever (MHF)); protein C, matrix protein M, phosphoprotein P, non-structural protein V, hemagglutinin glycoprotein H, polymerase L, nucleoprotein N, fusion protein F (Measles virus, Measles); members of the ABC transporter family (LolC, OppA, and PotF), putative lipoprotein releasing system transmembrane protein LolC/E, flagellin FliC, *Burkholderia* intracellular motility A BimA, bacterial Elongation factor-Tu EF-Tu, 17 kDa OmpA-like protein, boaA coding protein, boaB coding protein (*Burkholderia pseudomallei*, Meliodosis (Whitmore's disease)); pilin proteins, minor pilin-associated subunit pilC, major pilin subunit and variants pilE, pilS, phase variation protein porA, Porin B PorB, protein TraD, Neisserial outer membrane antigen H.8, 70 kDa antigen, major outer membrane protein PI, outer membrane proteins HA and P1B, W antigen, surface protein A NspA, transferrin binding protein TbpA, transferrin binding protein TbpB, PBP2, mtrR coding protein, ponA coding protein, membrane permease FbpBC, FbpABC protein system, LbpAB proteins, outer membrane protein Opa, outer membrane transporter FetA, iron-repressed regulator MpeR, factor H-binding protein fHbp, adhesin NadA, protein NhbA, repressor FarR (*Neisseria meningitidis*, Meningococcal disease); 66 kDa protein, 22 kDa protein (usually *Metagonimus yokagawai*, Metagonimiasis); polar tube proteins (34, 75, and 170 kDa in Glugea, 35, 55 and 150 kDa in Encephalitozoon), kinesin-related protein, RNA polymerase II largest subunit, similar of integral membrane protein YIPA, anti-silencing protein 1, heat shock transcription factor HSF, protein kinase, thymidine kinase, NOP-2 like nucleolar protein (Microsporidia phylum, Microsporidiosis); CASP8 and FADD-like apoptosis regulator, Glutathione peroxidase GPX1, RNA helicase NPH-II NPH2, Poly(A) polymerase catalytic subunit PAPL, Major envelope protein P43K, early transcription factor 70 kDa subunit VETFS, early transcription factor 82 kDa subunit VETFL, metalloendopeptidase G1-type, nucleoside triphosphatase I NPH1, replication protein A28-like MC134L, RNA polymerase 7 kDa subunit RPO7 (Molluscum contagiosum virus (MCV), Molluscum contagiosum (MC)); matrix protein M, phosphoprotein P/V, small hydrophobic protein SH, nucleoprotein N, protein V, fusion glycoprotein F, hemagglutinin-neuraminidase HN, RNA polymerase L (Mumps virus, Mumps); Outer membrane proteins OM, cell surface antigen OmpA, cell surface antigen OmpB (sca5), cell surface protein SCA4, cell surface protein SCA1, intracytoplasmic protein D, crystalline surface layer protein SLP, protective surface protein antigen SPA (*Rickettsia typhi*, Murine typhus (Endemic typhus)); adhesin P1, adhesion P30, protein p116, protein P40, cytoskeletal protein HMW1, cytoskeletal protein HMW2, cytoskeletal protein HMW3, MPN152 coding protein, MPN426 coding protein, MPN456 coding protein, MPN-500 coding protein (*Mycoplasma pneumoniae, Mycoplasma* pneumonia); NocA, Iron dependent regulatory protein, VapA, VapD, VapF, VapG, caseinolytic protease, filament tip-associated 43-kDa protein, protein P24, protein P61, 15-kDa protein, 56-kDa protein (usually *Nocardia asteroides* and other *Nocardia* species, Nocardiosis); venom allergen homolog-like protein VAL-1, abundant larval transcript ALT-1, abundant larval transcript ALT-2, thioredoxin peroxidase TPX, vespid allergen homologue VAH, thiordoxin peroxidase 2 TPX-2, antigenic protein SXP (peptides N, N1, N2, and N3), activation associated protein-1 ASP-1, Thioredoxin TRX, transglutaminase BmTGA, glutathione-S-transferases GST, myosin, vespid allergen homologue VAH, 175 kDa collagenase, glyceraldehyde-3-phosphate dehydrogenase GAPDH, cuticular collagen Col-4, Secreted Larval Acidic Proteins SLAPs, chitinase CHI-1, maltose binding protein MBP, glycolytic enzyme fructose-1,6-bisphosphate aldolase Fba, tropomyosin TMY-1, nematode specific gene product OvB20, onchocystatin CPI-2, Cox-2 (*Onchocerca volvulus*, Onchocerciasis (River blindness)); 43 kDa secreted glycoprotein, glycoprotein gp0, glycoprotein gp75, antigen Pb27, antigen Pb40, heat shock protein Hsp65, heat shock protein Hsp70, heat shock protein Hsp90, protein P10, triosephosphate isomerase TPI, N-acetyl-glucosamine-binding lectin Paracoccin, 28 kDa protein Pb28 (*Paracoccidioides brasiliensis*, Paracoccidioidomycosis (South American blastomycosis)); 28-kDa cruzipain-like cystein protease Pw28CCP (usually *Paragonimus westermani* and other *Paragonimus* species, Paragonimiasis); outer membrane protein OmpH, outer membrane protein Omp28, protein PM1539, protein PM0355, protein PM1417, repair protein MutL, protein BcbC, protein PM0305, formate dehydrogenase-N, protein PM0698, protein PM1422, DNA gyrase, lipoprotein PlpE, adhesive protein Cp39, heme acquisition system receptor HasR, 39 kDa capsular protein, iron-regulated OMP IROMP, outer membrane protein OmpA87, fimbrial protein Ptf, fimbrial subunit protein PtfA, transferrin binding protein Tbpl, esterase enzyme MesA, *Pasteurella multocida* toxin PMT, adhesive protein Cp39 (*Pasteurella* genus, Pasteurellosis); "filamentous hemagglutinin FhaB, adenylate cyclase CyaA, pertussis toxin subunit 4 precursor PtxD, pertactin precursor Prn, toxin subunit 1 PtxA, protein Cpn60, protein brkA, pertussis toxin subunit 2 precursor PtxB, pertussis toxin subunit 3 precursor PtxC, pertussis toxin subunit 5 precursor PtxE, pertactin Prn, protein Fim2, protein Fim3;" (*Bordetella pertussis*, Pertussis (Whooping cough)); "F1 capsule antigen, virulence-associated V antigen, secreted effector protein LcrV, V antigen, outer membrane protease Pla, secreted effector protein YopD, putative secreted protein-tyrosine phosphatase YopH, needle complex major subunit YscF, protein kinase YopO, putative autotransporter protein YapF, inner membrane ABC-transporter YbtQ (Irp7), putative sugar binding protein YP00612, heat shock protein 90 HtpG, putative sulfatase protein YdeN, outer-membrane lipoprotein carrier protein LolA, secretion chaperone YerA, putative lipoprotein YP00420, hemolysin activator protein HpmB, pesticin/yersiniabactin outer membrane receptor Psn, secreted effector protein YopE, secreted effector protein YopF, secreted effector protein YopK, outer membrane protein YopN, outer membrane protein YopM, Coagulase/fibrinolysin precursor Pla;" (*Yersinia pestis*, Plague); protein PhpA, surface adhesin PsaA, pneumolysin Ply, ATP-dependent protease Clp, lipoate-protein ligase Lp1A, cell wall surface anchored protein psrP, sortase SrtA, glutamyl-tRNA synthetase GltX, choline binding protein A CbpA, pneumococcal surface protein A PspA, pneumococcal surface protein C PspC, 6-phosphogluconate dehydrogenase Gnd, iron-binding protein PiaA, Murein hydrolase LytB, proteon LytC, protease A1 (*Streptococcus pneumoniae*, Pneumococcal infection); major surface protein B, kexin-like protease KEX1, protein A12, 55 kDa antigen P55, major surface glycoprotein Msg (*Pneumocystis jirovecii*, Pneumocystis pneumonia (PCP)); genome polyprotein, polymerase 3D, viral capsid protein VP1, viral capsid protein VP2, viral capsid protein VP3, viral capsid protein VP4, protease 2A, protease 3C (Poliovirus, Poliomyelitis); protein Nfa1, exendin-3, secretory lipase, cathepsin B-like protease, cysteine protease, cathepsin, peroxiredoxin, protein Cry1Ac (usually *Naegleria fowleri*, Primary amoebic meningoencephalitis (PAM)); agnoprotein, large T antigen, small T antigen, major capsid protein VP1, minor capsid protein Vp2 (JC virus, Progressive multifocal leukoencephalopathy); low calcium response protein E LCrE, chlamydial outer protein N CopN, serine/threonine-protein kinase PknD, acyl-carrier-protein S-malonyltransferase FabD, single-stranded DNA-binding protein Ssb, major outer membrane protein MOMP, outer membrane protein 2 Omp2, polymorphic membrane protein family (Pmp1, Pmp2, Pmp3, Pmp4, Pmp5, Pmp6, Pmp7, Pmp8, Pmp9, Pmp10, Pmp11, Pmp12, Pmp13, Pmp14, Pmp15, Pmp16, Pmp17, Pmp18, Pmp19, Pmp20, Pmp21) (*Chlamydophila psittaci*, Psittacosis); outer membrane protein P1, heat shock protein B HspB, peptide ABC transporter, GTP-binding protein, protein IcmB, ribonuclease R, phosphatas SixA, protein DsbD, outer membrane protein TolC, DNA-binding protein PhoB, ATPase DotB, heat shock protein B HspB, membrane protein Com1, 28 kDa protein, DNA-3-methyladenine glycosidase I, pouter membrane protein OmpH, outer membrane protein AdaA, glycine cleavage system T-protein (*Coxiella burnetii*, Q fever); nucleoprotein N, large structural protein L, phophoprotein P, matrix protein M, glycoprotein G (Rabies virus, Rabies); fusionprotein F, nucleoprotein N, matrix protein M, matrix protein M2-1, matrix protein M2-2, phophoprotein P, small hydrophobic protein SH, major surface glycoprotein G, polymerase L, non-structural protein 1 NS1, non-structural protein 2 NS2 (Respiratory syncytial virus (RSV), Respiratory syncytial virus infection); genome polyprotein, polymerase 3D, viral capsid protein VP1, viral capsid protein VP2, viral capsid protein VP3, viral capsid protein VP4, protease 2A, protease 3C (Rhinovirus, Rhinovirus infection); outer membrane proteins OM, cell surface antigen OmpA, cell surface antigen OmpB (sca5), cell surface protein SCA4, cell surface protein SCA1, protein PS120, intracytoplasmic protein D, protective surface protein antigen SPA (*Rickettsia* genus, Rickettsial infection); outer membrane proteins OM, cell surface antigen OmpA, cell surface antigen OmpB (sca5), cell surface protein SCA4, cell surface protein SCA1, intracytoplasmic protein D (*Rickettsia akari*, Rickettsialpox); envelope glycoprotein GP, polymerase L, nucleoprotein N, non-structural protein NSS (Rift Valley fever virus, Rift Valley fever (RVF)); outer membrane proteins OM, cell surface antigen OmpA, cell surface antigen OmpB (sca5), cell surface protein SCA4, cell surface protein SCA1, intracytoplasmic protein D (*Rickettsia rickettsii*, Rocky mountain spotted fever (RMSF)); "non-structural protein 6 NS6, non-structural protein 2 NS2, intermediate capsid protein VP6, inner capsid protein VP2, non-structural protein 3 NS3, RNA-directed RNA polymerase L, protein VP3, non-structural protein 1 NS1, non-structural protein 5 NSS, outer capsid glycoprotein VP7, non-structural glycoprotein 4 NS4, outer capsid protein VP4;" (Rotavirus, Rotavirus infection); polyprotein P200, glycoprotein E1, glycoprotein E2, protein NS2, capsid protein C (Rubella virus, Rubella); chaperonin GroEL (MopA), inositol phosphate phosphatase SopB, heat shock protein Hs1U, chaperone protein DnaJ, protein TviB, protein IroN, flagellin FliC, invasion protein SipC, glycoprotein gp43, outer membrane protein LamB, outer membrane protein PagC, outer membrane protein TolC, outer membrane protein NmpC, outer membrane protein FadL, transport protein SadA, transferase WgaP, effector proteins SifA, SteC, SseL, SseJ and SseF (*Salmonella* genus, Salmonellosis); "protein 14, non-structural protein NS7b, non-structural protein NS8a, protein 9b, protein 3a, nucleoprotein N, non-structural protein NS3b, non-structural protein NS6, protein 7a, non-structural protein NS 8b, membrane protein M, envelope small membrane protein EsM, replicase polyprotein 1a, spike glycoprotein S, replicase polyprotein 1ab;" (SARS coronavirus, SARS (Severe Acute Respiratory Syndrome)); serin protease, Atypical *Sarcoptes* Antigen 1 ASA1, glutathione S-transferases GST, cystein protease, serine protease, apolipoprotein (*Sarcoptes scabiei*, Scabies); glutathione S-transferases GST, paramyosin, hemoglbinase SM32, major egg antigen, 14 kDa fatty acid-binding protein Sm14, major larval surface antigen P37, 22.6 kDa tegumental antigen, calpain CANP, triphospate isomerase Tim, surface protein 9B, outer capsid protein VP2, 23 kDa integral membrane protein Sm23, Cu/Zn-superoxide dismutase, glycoprotein Gp, myosin (*Schistosoma* genus, Schistosomiasis (Bilharziosis)); 60 kDa chaperonin, 56 kDa type-specific antigen, pyruvate phosphate dikinase, 4-hydroxybenzoate octaprenyltransferase (*Orientia tsutsugamushi*, Scrub typhus); dehydrogenase GuaB, invasion protein Spa32, invasin IpaA, invasin IpaB, invasin IpaC, invasin IpaD, invasin IpaH, invasin IpaJ (*Shigella* genus, Shigellosis (Bacillary dysentery)); protein P53, virion protein US10 homolog, transcriptional regulator 1E63, transcriptional transactivator 1E62, protease P33, alpha trans-inducing factor 74 kDa protein, deoxyuridine 5'-triphosphate nucleotidohydrolase, transcriptional transactivator 1E4, membrane protein UL43 homolog, nuclear phosphoprotein UL3 homolog, nuclear protein UL4 homolog, replication origin-binding protein, membrane protein 2, phosphoprotein 32, protein 57, DNA polymerase processivity factor, portal protein 54, DNA primase, tegument protein UL14 homolog, tegument protein UL21 homolog, tegument protein UL55 homolog, tripartite terminase subunit UL33 homolog, tripartite terminase subunit UL15 homolog, capsid-binding protein 44, virion-packaging protein 43 (Varicella zoster virus (VZV), Shingles (Herpes zoster)); truncated 3-beta hydroxy-5-ene steroid dehydrogenase homolog, virion membrane protein A13, protein A19, protein A31, truncated protein A35 homolog, protein A37.5 homolog, protein A47, protein A49, protein A51, semaphorin-like protein A43, serine proteinase inhibitor 1, serine proteinase inhibitor 2, serine proteinase inhibitor 3, protein A6, protein B15, protein C1, protein C5, protein C6, protein F7, protein F8, protein F9, protein F11, protein F14, protein F15, protein F16 (Variola major or Variola minor, Smallpox (Variola)); adhesin/glycoprotein gp70, proteases (*Sporothrix schenckii*, Sporotrichosis); heme-iron binding protein IsdB, collagen adhesin Cna, clumping factor A ClfA, protein MecA, fibronectin-binding protein A FnbA, enterotoxin type A EntA, enterotoxin type B EntB, enterotoxin type C EntC1, enterotoxin type C EntC2, enterotoxin type D EntD, enterotoxin type E EntE, Toxic shock syndrome toxin-1 TSST-1, Staphylokinase, Penicillin binding protein 2a PBP2a (MecA), secretory antigen SssA (*Staphylococcus* genus, Staphylococcal food poisoning); heme-iron binding protein IsdB, collagen adhesin Cna, clumping factor A ClfA, protein MecA, fibronectin-binding protein A FnbA, enterotoxin type A EntA, enterotoxin type B EntB, enterotoxin type C EntC1, enterotoxin type C EntC2, enterotoxin type D EntD, enterotoxin type E EntE, Toxic shock syndrome toxin-1 TSST-1, Staphylokinase, Penicillin binding protein 2a PBP2a (MecA), secretory antigen SssA (*Staphylococcus* genus e.g. *aureus*, Staphylococcal infection); antigen Ss-IR, antigen NIE, strongylastacin, Na+-K+ATPase Sseat-6, tropomyosin SsTmy-1, protein LEC-5, 41 kDa aantigen P5, 41-kDa larval protein, 31-kDa larval protein, 28-kDa larval protein (*Strongyloides stercoralis*, Strongyloidiasis); glycerophosphodiester phosphodiesterase GlpQ (Gpd), outer membrane protein TmpB, protein Tp92, antigen TpF1, repeat protein Tpr, repeat protein F TprF, repeat protein G TprG, repeat protein I TprI, repeat protein J TprJ, repeat protein K TprK, treponemal membrane protein A TmpA, lipoprotein, 15 kDa Tpp15, 47 kDa membrane antigen, miniferritin TpF1, adhesin Tp0751, lipoprotein TP0136, protein TpN17, protein TpN47, outer membrane protein TP0136, outer membrane protein TP0155, outer membrane protein TP0326, outer membrane protein TP0483, outer membrane protein TP0956 (*Treponema pallidum*, Syphilis); Cathepsin L-like proteases, 53/25-kDa antigen, 8 kDa family members, cysticercus protein with a marginal trypsin-like activity TsAg5, oncosphere protein TSOL18, oncosphere protein TSOL45-1A, lactate dehydrogenase A LDHA, lactate dehydrogenase B LDHB (*Taenia* genus, Taeniasis); tetanus toxin TetX, tetanus toxin C TTC, 140 kDa S layer protein, flavoprotein beta-subunit CT3, phospholipase (lecithinase), phosphocarrier protein HPr (*Clostridium tetani*, Tetanus (Lockjaw)); genome polyprotein, protein E, protein M, capsid protein C (Tick-borne encephalitis virus (TBEV), Tick-borne encephalitis); 58-kDa antigen, 68-kDa antigens, *Toxocara* larvae excretory-secretory antigen TES, 32-kDa glycoprotein, glycoprotein TES-70, glycoprotein GP31, excretory-secretory antigen TcES-57, perienteric fluid antigen Pe, soluble extract antigens Ex, excretory/secretory larval antigens ES, antigen TES-120, polyprotein allergen TBA-1, cathepsin L-like cysteine protease c-cpl-1, 26-kDa protein (*Toxocara canis* or *Toxocara cati*, Toxocariasis (Ocular Larva Migrans (OLM) and Visceral Larva Migrans (VLM))); microneme proteins (MIC1, MIC2, MIC3, MIC4, MIC5, MIC6, MIC7, MIC8), rhoptry protein Rop2, rhoptry proteins (Rop1, Rop2, Rop3, Rop4, Rop5, Rop6, Rop7, Rop16, Rjop17), protein SR1, surface antigen P22, major antigen p24, major surface antigen p30, dense granule proteins (GRA1, GRA2, GRA5, GRA4, GRA5, GRA6, GRA7, GRAB, GRA5, GRA10), 28 kDa antigen, surface antigen SAG1, SAG2 related antigen, nucleoside-triphosphatase 1, nucleoside-triphosphatase 2, protein Stt3, HesB-like domain-containing protein, rhomboid-like protease 5, toxomepsin 1 (*Toxoplasma gondii*, Toxoplasmosis); 43 kDa secreted glycoprotein, 53 kDa secreted glycoprotein, paramyosin, antigen Ts21, antigen Ts87, antigen p46000, TSL-1 antigens, caveolin-1 CAV-1, 49 kDa newborn larva antigen, prosaposin homologue, serine protease, serine proteinase inhibitor, 45-kDa glycoprotein Gp45 (*Trichinella spiralis*, Trichinellosis); Myb-like transcriptional factors (Myb1, Myb2, Myb3), adhesion protein AP23, adhesion protein AP33, adhesin protein AP33-3, adhesins AP51, adhesin AP65, adhesion protein AP65-1, alpha-actinin, kinesin-associated protein, teneurin, 62 kDa proteinase, subtilisin-like serine protease SUB1, cysteine proteinase gene 3 CP3, alpha-enolase Enol, cysteine proteinase CP30, heat shock proteins (Hsp70, Hsp60), immunogenic protein P270, (*Trichomonas vaginalis*, Trichomoniasis); beta-tubulin, 47-kDa protein, secretory leucocyte-like proteinase-1 SLP-1, 50-kDa protein TT50, 17 kDa antigen, 43/47 kDa protein (*Trichuris trichiura*, Trichuriasis (Whipworm infection)); protein ESAT-6 (EsxA), 10 kDa filtrate antigen EsxB, secreted antigen 85-B FBPB, fibronectin-binding protein A FbpA (Ag85A), serine protease PepA, PPE family protein PPE18, fibronectin-binding protein D FbpD, immunogenic protein MPT64, secreted protein MPT51, catalase-peroxidase-peroxynitritase T KATG, periplasmic phosphate-binding lipoprotein PSTS3 (PBP-3, Phos-1), iron-regulated heparin binding hemagglutinin Hbha, PPE family protein PPE14, PPE family protein PPE68, protein Mtb72F, protein Apa, immunogenic protein MPT63, periplasmic phosphate-binding lipoprotein PSTS1 (PBP-1), molecular chaperone DnaK, cell surface lipoprotein Mpt83, lipoprotein P23, phosphate transport system permease protein pstA, 14 kDa antigen, fibronectin-binding protein C FbpC1, Alanine dehydrogenase TB43, Glutamine synthetase 1, ESX-1 protein, protein CFP10, TB10.4 protein, protein MPT83, protein MTB12, protein MTB8, Rpf-like proteins, protein MTB32, protein MTB39, crystallin, heat-shock protein HSP65, protein PST-S(usually *Mycobacterium tuberculosis*, Tuberculosis); outer membrane protein FobA, outer membrane protein FobB, intracellular growth locus IglC1, intracellular growth locus IglC2, aminotransferase Wbtl, chaperonin GroEL, 17 kDa major membrane protein TUL4, lipoprotein LpnA, chitinase family 18 protein, isocitrate dehydrogenase, Nif3 family protein, type IV pili glycosylation protein, outer membrane protein tolC, FAD binding family protein, type IV pilin multimeric outer membrane protein, two component sensor protein KdpD, chaperone protein DnaK, protein TolQ (*Francisella tularensis*, Tularemia); "MB antigen, urease, protein GyrA, protein GyrB, protein ParC, protein ParE, lipid associated membrane proteins LAMP, thymidine kinase TK, phospholipase PL-A1, phospholipase PL-A2, phospholipase PL-C, surface-expressed 96-kDa antigen;" (*Ureaplasma urealyticum*, *Ureaplasma urealyticum* infection); non-structural polyprotein, structural polyprotein, capsid protein CP, protein E1, protein E2, protein E3, protease P1, protease P2, protease P3 (Venezuelan equine encephalitis virus, Venezuelan equine encephalitis); glycoprotein GP, matrix protein Z, polymerase L, nucleoprotein N (Guanarito virus, Venezuelan hemorrhagic fever); polyprotein, protein E, protein M, capsid protein C, protease NS3, protein NS1, protein NS2A, protein AS2B, protein NS4A, protein NS4B, protein NS5 (West Nile virus, West Nile Fever); capsid protein CP, protein E1, protein E2, protein E3, protease P2 (Western equine encephalitis virus, Western equine encephalitis); genome polyprotein, protein E, protein M, capsid protein C, protease NS3, protein NS1, protein NS2A, protein AS2B, protein NS4A, protein NS4B, protein NS5 (Yellow fever virus, Yellow fever); putative Yop targeting protein YobB, effector protein YopD, effector protein YopE, protein YopH, effector protein YopJ, protein translocation protein YopK, effector protein YopT, protein YpkA, flagellar biosyntheses protein FlhA, peptidase M48, potassium efflux system KefA, transcriptional regulatoer RovA, adhesin Ifp, translocator portein LcrV, protein PcrV, invasin Inv, outer membrane protein OmpF-like porin, adhesin YadA, protein kinase C, phospholipase C1, protein PsaA, mannosyltransferase-like protein WbyK, protein YscU, antigen YPMa (*Yersinia pseudotuberculosis, Yersinia pseudotuberculosis* infection); effector protein YopB, 60 kDa chaperonin, protein WbcP, tyrosin-protein phosphatase YopH, protein YopQ, enterotoxin, Galactoside permease, reductaase NrdE, protein YasN, Invasin Inv, adhesin YadA, outer membrane porin F OmpF, protein UspA1, protein EibA, protein Hia, cell surface protein Ail, chaperone SycD, protein LcrD, protein LcrG, protein LcrV, protein SycE, protein YopE, regulator protein TyeA, protein YopM, protein YopN, protein YopO, protein YopT, protein YopD, protease ClpP, protein MyfA, protein Fi1A, and protein PsaA (*Yersinia enterocolitica*, Yersiniosis).
(in brackets is the particular pathogen or the family of pathogens of which the antigen(s) is/are derived and the infectious disease with which the pathogen is associated)

The coding region of the inventive nucleic acid according to the first aspect of the present invention may occur as a mono-, di-, or even multicistronic nucleic acid, i.e. a nucleic acid which carries the coding sequences of one, two or more proteins or peptides. Such coding sequences in di-, or even multicistronic nucleic acids may be separated by at least one internal ribosome entry site (IRES) sequence, e.g. as described herein or by signal peptides which induce the cleavage of the resulting polypeptide which comprises several proteins or peptides.

According to the first aspect of the present invention, the inventive nucleic acid sequence comprises a coding region, encoding a peptide or protein which comprises a pathogenic antigen or a fragment, variant or derivative thereof. Preferably, the encoded pathogenic antigen is no histone protein. In the context of the present invention such a histone protein is typically a strongly alkaline protein found in eukaryotic cell nuclei, which package and order the DNA into structural units called nucleosomes. Histone proteins are the chief protein components of chromatin, act as spools around which DNA winds, and play a role in gene regulation. Without histones, the unwound DNA in chromosomes would be very long (a length to width ratio of more than 10 million to one in human DNA). For example, each human cell has about 1.8 meters of DNA, but wound on the histones it has about 90 millimeters of chromatin, which, when duplicated and condensed during mitosis, result in about 120 micrometers of chromosomes. More preferably, in the context of the present invention such a histone protein is typically defined as a highly conserved protein selected from one of the following five major classes of histones: H1/H5, H2A, H2B, H3, and H4", preferably selected from mammalian histone, more preferably from human histones or histone proteins. Such histones or histone proteins are typically organised into two super-classes defined as core histones, comprising histones H2A, H2B, H3 and H4, and linker histones, comprising histones H1 and H5.

In this context, linker histones, preferably excluded from the scope of protection of the pending invention, preferably mammalian linker histones, more preferably human linker histones, are typically selected from H1, including H1F, particularly including H1F0, H1FNT, H1FOO, H1FX, and H1H1, particularly including HIST1H1A, HIST1H1B, HIST1H1C, HIST1H1D, HIST1H1E, HIST1H1T; and Furthermore, core histones, preferably excluded from the scope of protection of the pending invention, preferably mammalian core histones, more preferably human core histones, are typically selected from H2A, including H2AF, particularly including H2AFB1, H2AFB2, H2AFB3, H2AFJ, H2AFV, H2AFX, H2AFY, H2AFY2, H2AFZ, and H2A1, particularly including HIST1H2AA, HIST1H2AB, HIST1H2AC, HIST1H2AD, HIST1H2AE, HIST1H2AG, HIST1H2AI, HIST1H2AJ, HIST1H2AK, HIST1H2AL, HIST1H2AM, and H2A2, particularly including HIST2H2AA3, HIST2H2AC; H2B, including H2BF, particularly including H2BFM, H2BFO, H2BFS, H2BFWT H2B1, particularly including HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, and H2B2, particularly including HIST2H2BE; H3, including H3A1, particularly including HIST1H3A, HIST1H3B, HIST1H3C, HIST1H3D, HIST1H3E, HIST1H3F, HIST1H3G, HIST1H3H, HIST1H3I, HIST1H3J, and H3A2, particularly including HIST2H3C, and H3A3, particularly including HIST3H3; H4, including H41, particularly including HIS T1H4A, HIS T1H4B, HIS T1H4C, HIS T1H4D, HIS T1H4E, HIST1H4F, HIST1H4G, HIST1H4H, HIST1H4I, HIST1H4J, HIST1H4K, HIST1H4L, and H44, particularly including HIST4H4, and H5.

According to the first aspect of the present invention, the inventive nucleic acid sequence comprises a coding region, encoding a peptide or protein which comprises a pathogenic antigen or a fragment, variant or derivative thereof. Preferably, the encoded pathogenic antigen is no reporter protein (e.g. Luciferase, Green Fluorescent Protein (GFP), Enhanced Green Fluorescent Protein (EGFP), β-Galactosidase) and no marker or selection protein (e.g. alpha-Globin, Galactokinase and Xanthine:guanine phosphoribosyl transferase (GPT)). Preferably, the nucleic acid sequence of the invention does not contain an antibiotics resistance gene, e.g. a (bacterial) neo gene sequence (Neomycin resistance gene) or a CAT gene sequence (coding for chloramphenicol acetyltransferase; chloramphenicol resistance gene).

The inventive nucleic acid as define above, comprises or codes for a) a coding region, encoding a peptide or protein which comprises a pathogenic antigen or a fragment, variant or derivative thereof; b) at least one histone stem-loop, and c) a poly(A) sequence or polyadenylation signal; preferably for increasing the expression of said encoded peptide or protein, wherein the encoded peptide or protein is preferably no histone protein, no reporter protein and/or no marker or selection protein, as defined above. The elements b) to c) of the inventive nucleic acid may occur in the inventive nucleic acid in any order, i.e. the elements a), b) and c) may occur in the order a), b) and c) or a), c) and b) from 5' to 3' direction in the inventive nucleic acid sequence, wherein further elements as described herein, may also be contained, such as a 5'-CAP structure, a poly(C) sequence, stabilization sequences, IRES sequences, etc. Each of the elements a) to c) of the inventive nucleic acid, particularly a) in di- or multicistronic constructs and/or each of the elements b) and c), more preferably element b) may also be repeated at least once, preferably twice or more in the inventive nucleic acid. As an example, the inventive nucleic acid may show its sequence elements a), b) and optionally c) in e.g. the following order:

5'-coding region-histone stem-loop-poly(A) sequence-3'; or

5'-coding region-histone stem-loop-polyadenylation signal-3'; or

5'-coding region-poly(A) sequence-histone stem-loop-3'; or

5'-coding region-polyadenylation signal-histone stem-loop-3'; or

5'-coding region-coding region-histone stem-loop-polyadenylation signal-3'; or

5'-coding region-histone stem-loop-histone stem-loop-poly(A) sequence-3'; or

5'-coding region-histone stem-loop-histone stem-loop-polyadenylation signal-3'; etc.

In this context it is particularly preferred that the inventive nucleic acid sequence comprises or codes for a) a coding region, encoding a peptide or protein which comprises a pathogenic antigen or fragment, variant or derivative thereof; b) at least one histone stem-loop, and c) a poly(A) sequence or polyadenylation sequence; preferably for increasing the expression level of said encoded peptide or protein, wherein the encoded protein is preferably no histone protein, no reporter protein (e.g. Luciferase, GFP, EGFP, β-Galactosidase, particularly EGFP) and/or no marker or selection protein (e.g. alpha-Globin, Galactokinase and Xanthine:Guanine phosphoribosyl transferase (GPT)).

In a further preferred embodiment of the first aspect the inventive nucleic acid sequence as defined herein may also occur in the form of a modified nucleic acid.

In this context, the inventive nucleic acid sequence as defined herein may be modified to provide a "stabilized nucleic acid", preferably a stabilized RNA, more preferably an RNA that is essentially resistant to in vivo degradation (e.g. by an exo- or endo-nuclease). A stabilized nucleic acid may e.g. be obtained by modification of the G/C content of the coding region of the inventive nucleic acid sequence, by introduction of nucleotide analogues (e.g. nucleotides with backbone modifications, sugar modifications or base modifications) or by introduction of stabilization sequences in the 3'- and/or 5'-untranslated region of the inventive nucleic acid sequence.

As mentioned above, the inventive nucleic acid sequence as defined herein may contain nucleotide analogues/modifications e.g. backbone modifications, sugar modifications or base modifications. A backbone modification in connection with the present invention is a modification in which phosphates of the backbone of the nucleotides contained in inventive nucleic acid sequence as defined herein are chemically modified. A sugar modification in connection with the present invention is a chemical modification of the sugar of the nucleotides of the inventive nucleic acid sequence as defined herein. Furthermore, a base modification in connection with the present invention is a chemical modification of the base moiety of the nucleotides of the nucleic acid molecule of the inventive nucleic acid sequence. In this context nucleotide analogues or modifications are preferably selected from nucleotide analogues which are applicable for transcription and/or translation.

In a particular preferred embodiment of the first aspect of the present invention the herein defined nucleotide analogues/modifications are selected from base modifications which additionally increase the expression of the encoded protein and which are preferably selected from 2-amino-6-chloropurineriboside-5'-triphosphate, 2-aminoadenosine-5'-triphosphate, 2-thiocytidine-5'-triphosphate, 2-thiouridine-5'-triphosphate, 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-iodocytidine-5'-triphosphate, 5-iodouridine-5'-triphosphate, 5-methylcytidine-5'-triphosphate, 5-methyluridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

According to a further embodiment, the inventive nucleic acid sequence as defined herein can contain a lipid modification. Such a lipid-modified nucleic acid typically comprises a nucleic acid as defined herein. Such a lipid-modified nucleic acid molecule of the inventive nucleic acid sequence as defined herein typically further comprises at least one linker covalently linked with that nucleic acid molecule, and at least one lipid covalently linked with the respective linker. Alternatively, the lipid-modified nucleic acid molecule comprises at least one nucleic acid molecule as defined herein and at least one (bifunctional) lipid covalently linked (without a linker) with that nucleic acid molecule. According to a third alternative, the lipid-modified nucleic acid molecule comprises a nucleic acid molecule as defined herein, at least one linker covalently linked with that nucleic acid molecule, and at least one lipid covalently linked with the respective linker, and also at least one (bifunctional) lipid covalently linked (without a linker) with that nucleic acid molecule. In this context it is particularly preferred that the lipid modification is present at the terminal ends of a linear inventive nucleic acid sequence.

According to another preferred embodiment of the first aspect of the invention, the inventive nucleic acid sequence as defined herein, particularly if provided as an (m)RNA, can therefore be stabilized against degradation by RNases by the addition of a so-called "5' CAP" structure.

According to a further preferred embodiment of the first aspect of the invention, the inventive nucleic acid sequence as defined herein can be modified by a sequence of at least 10 cytidines, preferably at least 20 cytidines, more preferably at least 30 cytidines (so-called "poly(C) sequence"). Particularly, the inventive nucleic acid sequence may contain or code for a poly(C) sequence of typically about 10 to 200 cytidine nucleotides, preferably about 10 to 100 cytidine nucleotides, more preferably about 10 to 70 cytidine nucleotides or even more preferably about 20 to 50 or even 20 to 30 cytidine nucleotides. This poly(C) sequence is preferably located 3' of the coding region comprised in the inventive nucleic acid according to the first aspect of the present invention.

In a particularly preferred embodiment of the present invention, the G/C content of the coding region, encoding at least one peptide or protein which comprises a pathogenic antigen or a fragment, variant or derivative thereof of the inventive nucleic acid sequence as defined herein, is modified, particularly increased, compared to the G/C content of its particular wild type coding region, i.e. the unmodified coding region. The encoded amino acid sequence of the coding region is preferably not modified compared to the coded amino acid sequence of the particular wild type coding region.

The modification of the G/C-content of the coding region of the inventive nucleic acid sequence as defined herein is based on the fact that the sequence of any mRNA region to be translated is important for efficient translation of that mRNA. Thus, the composition and the sequence of various nucleotides are important. In particular, mRNA sequences having an increased G (guanosine)/C (cytosine) content are more stable than mRNA sequences having an increased A (adenosine)/U (uracil) content. According to the invention, the codons of the coding region are therefore varied compared to its wild type coding region, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage).

Depending on the amino acid to be encoded by the coding region of the inventive nucleic acid sequence as defined herein, there are various possibilities for modification of the nucleic acid sequence, e.g. the coding region, compared to its wild type coding region. In the case of amino acids which are encoded by codons which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present.

In contrast, codons which contain A and/or U nucleotides can be modified by substitution of other codons which code for the same amino acids but contain no A and/or U. Examples of these are:

the codons for Pro can be modified from CCU or CCA to CCC or CCG;
the codons for Arg can be modified from CGU or CGA or AGA or AGG to CGC or CGG;
the codons for Ala can be modified from GCU or GCA to GCC or GCG;
the codons for Gly can be modified from GGU or GGA to GGC or GGG.

In other cases, although A or U nucleotides cannot be eliminated from the codons, it is however possible to decrease the A and U content by using codons which contain a lower content of A and/or U nucleotides. Examples of these are:

the codons for Phe can be modified from UUU to UUC;
the codons for Leu can be modified from UUA, UUG, CUU or CUA to CUC or CUG;
the codons for Ser can be modified from UCU or UCA or AGU to UCC, UCG or AGC;
the codon for Tyr can be modified from UAU to UAC;
the codon for Cys can be modified from UGU to UGC;
the codon for His can be modified from CAU to CAC;
the codon for Gln can be modified from CAA to CAG;
the codons for Ile can be modified from AUU or AUA to AUC;
the codons for Thr can be modified from ACU or ACA to ACC or ACG;
the codons for Asn can be modified from AAU to AAC;
the codon for Lys can be modified from AAA to AAG;
the codons for Val can be modified from GUU or GUA to GUC or GUG;
the codon for Asp can be modified from GAU to GAC;
the codon for Glu can be modified from GAA to GAG;
the stop codon UAA can be modified to UAG or UGA.

In the case of the codons for Met (AUG) and Trp (UGG), on the other hand, there is no possibility of sequence modification.

The substitutions listed above can be used either individually or in all possible combinations to increase the G/C content of the coding region of the inventive nucleic acid sequence as defined herein, compared to its particular wild type coding region (i.e. the original sequence). Thus, for example, all codons for Thr occurring in the wild type sequence can be modified to ACC (or ACG).

In the above context, codons present in mRNA are shown. Therefore uridine present in an mRNA may also be present as thymidine in the respective DNA coding for the particular mRNA.

Preferably, the G/C content of the coding region of the inventive nucleic acid sequence as defined herein is increased by at least 7%, more preferably by at least 15%, particularly preferably by at least 20%, compared to the G/C content of the wild type coding region. According to a specific embodiment at least 5%, 10%, 20%, 30%, 40%, 50%, 60%, more preferably at least 70%, even more preferably at least 80% and most preferably at least 90%, 95% or even 100% of the substitutable codons in the coding region encoding at least one peptide or protein which comprises a pathogenic antigen or a fragment, variant or derivative thereof are substituted, thereby increasing the G/C content of said coding region.

In this context, it is particularly preferable to increase the G/C content of the coding region of the inventive nucleic acid sequence as defined herein, to the maximum (i.e. 100% of the substitutable codons), compared to the wild type coding region.

According to the invention, a further preferred modification of the coding region encoding at least one peptide or protein which comprises a pathogenic antigen or a fragment, variant or derivative thereof of the inventive nucleic acid sequence as defined herein, is based on the finding that the translation efficiency is also determined by a different frequency in the occurrence of tRNAs in cells. Thus, if so-called "rare codons" are present in the coding region of the inventive nucleic acid sequence as defined herein, to an increased extent, the corresponding modified nucleic acid sequence is translated to a significantly poorer degree than in the case where codons coding for relatively "frequent" tRNAs are present.

In this context the coding region of the inventive nucleic acid sequence is preferably modified compared to the corresponding wild type coding region such that at least one codon of the wild type sequence which codes for a tRNA which is relatively rare in the cell is exchanged for a codon which codes for a tRNA which is relatively frequent in the cell and carries the same amino acid as the relatively rare tRNA. By this modification, the coding region of the inventive nucleic acid sequence as defined herein, is modified such that codons for which frequently occurring tRNAs are available are inserted. In other words, according to the invention, by this modification all codons of the wild type coding region which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the coding region of the inventive nucleic acid sequence as defined herein, with the "frequent" codons without modifying the amino acid sequence of the peptide or protein encoded by the coding region of the nucleic acid sequence. This preferred embodiment allows provision of a particularly efficiently translated and stabilized (modified) inventive nucleic acid sequence as defined herein.

According to another preferred embodiment of the first aspect of the invention, the inventive nucleic acid sequence as defined herein, preferably has additionally at least one 5' and/or 3' stabilizing sequence. These stabilizing sequences in the 5' and/or 3' untranslated regions have the effect of increasing the half-life of the nucleic acid, particularly of the mRNA in the cytosol. These stabilizing sequences can have 100% sequence identity to naturally occurring sequences which occur in viruses, bacteria and eukaryotes, but can also be partly or completely synthetic. The untranslated sequences (UTR) of the (alpha-)globin gene, e.g. from Homo sapiens or Xenopus laevis may be mentioned as an example of stabilizing sequences which can be used in the present invention for a stabilized nucleic acid. Another example of a stabilizing sequence has the general formula (C/U)CCAN$_x$CCC(U/A)Py$_x$UC(C/U)CC (SEQ ID NO: 55), which is contained in the 3'-UTRs of the very stable RNAs which code for (alpha-)globin, type(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art. In this context it is particularly preferred that the 3' UTR sequence of the alpha globin gene is located 3' of the coding region encoding at least one peptide or protein which comprises a pathogenic antigen or a fragment, variant or derivative thereof comprised in the inventive nucleic acid sequence according to the first aspect of the present invention.

Substitutions, additions or eliminations of bases are preferably carried out with the inventive nucleic acid sequence as defined herein, using a DNA matrix for preparation of the nucleic acid sequence by techniques of the well-known site directed mutagenesis or with an oligonucleotide ligation strategy (see e.g. Maniatis et al., Molecular Cloning: A Laboratory Manual, Cold Spring Harbor Laboratory Press, 3rd ed., Cold Spring Harbor, NY, 2001).

Any of the above modifications may be applied to the inventive nucleic acid sequence as defined herein and further to any nucleic acid as used in the context of the present invention and may be, if suitable or necessary, be combined with each other in any combination, provided, these combinations of modifications do not interfere with each other in the respective nucleic acid. A person skilled in the art will be able to take his choice accordingly.

Nucleic acid sequences used according to the present invention as defined herein may be prepared using any method known in the art, including synthetic methods such as e.g. solid phase synthesis, as well as in vitro methods, such as in vitro transcription reactions or in vivo reactions, such as in vivo propagation of DNA plasmids in bacteria.

In such a process, for preparation of the inventive nucleic acid sequence as defined herein, especially if the nucleic acid is in the form of an mRNA, a corresponding DNA molecule may be transcribed in vitro. This DNA matrix preferably comprises a suitable promoter, e.g. a T7 or SP6 promoter, for in vitro transcription, which is followed by the desired nucleotide sequence for the nucleic acid molecule, e.g. mRNA, to be prepared and a termination signal for in vitro transcription. The DNA molecule, which forms the matrix of the at least one RNA of interest, may be prepared by fermentative proliferation and subsequent isolation as part of a plasmid which can be replicated in bacteria. Plasmids which may be mentioned as suitable for the present invention are e.g. the plasmids pT7 Ts (GenBank accession number U26404; Lai et al., Development 1995, 121: 2349 to 2360), pGEM® series, e.g. pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, FL, 2001.

The inventive nucleic acid sequence as defined herein as well as proteins or peptides as encoded by this nucleic acid sequence may comprise fragments or variants of those sequences. Such fragments or variants may typically comprise a sequence having a sequence identity with one of the above mentioned nucleic acids, or with one of the proteins or peptides or sequences, if encoded by the inventive nucleic acid sequence, of at least 5%, 10%, 20%, 30%, 40%, 50%, 60%, preferably at least 70%, more preferably at least 80%, equally more preferably at least 85%, even more preferably at least 90% and most preferably at least 95% or even 97%, 98% or 99%, to the entire wild type sequence, either on nucleic acid level or on amino acid level.

"Fragments" of proteins or peptides in the context of the present invention (e.g. as encoded by the inventive nucleic acid sequence as defined herein) may comprise a sequence of a protein or peptide as defined herein, which is, with regard to its amino acid sequence (or its encoded nucleic acid molecule), N-terminally, C-terminally and/or intrasequentially truncated/shortened compared to the amino acid sequence of the original (native) protein (or its encoded nucleic acid molecule). Such truncation may thus occur either on the amino acid level or correspondingly on the nucleic acid level. A sequence identity with respect to such a fragment as defined herein may therefore preferably refer to the entire protein or peptide as defined herein or to the entire (coding) nucleic acid molecule of such a protein or peptide. Likewise, "fragments" of nucleic acids in the context of the present invention may comprise a sequence of a nucleic acid as defined herein, which is, with regard to its nucleic acid molecule 5' 3'- and/or intrasequentially truncated/shortened compared to the nucleic acid molecule of the original (native) nucleic acid molecule. A sequence identity with respect to such a fragment as defined herein may therefore preferably refer to the entire nucleic acid as defined herein and the preferred sequence identity level is as indicated herein. Fragments have the same biological function or specific activity or at least retain an activity of the natural full-length protein of at least 50%, more preferably at least 70%, even more preferably at least 90% (as measured in an appropriate functional assay, e.g. by quantification of the organism's B-cell response) as compared to the full-length native peptide or protein, e.g. its specific antigenic property. Accordingly, in a preferred embodiment, the "fragment" is a portion of the full-length antigenic protein, which exerts antigenic properties on the immune system as described herein.

Fragments of proteins or peptides in the context of the present invention (e.g. as encoded by the inventive nucleic acid sequence as defined herein) may furthermore comprise a sequence of a protein or peptide as defined herein, which has a length of about 6 to about 20 or even more amino acids, e.g. fragments as processed and presented by MHC class I molecules, preferably having a length of about 8 to about 10 amino acids, e.g. 8, 9, or 10, (or even 6, 7, 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T-cells in form of a complex consisting of the peptide fragment and an MHC molecule, i.e. the fragments are typically not recognized in their native form. Fragments of proteins or peptides as defined herein may comprise at least one epitope of those proteins or peptides. Furthermore also domains of a protein, like the extracellular domain, the intracellular domain or the transmembrane domain and shortened or truncated versions of a protein may be understood to comprise a fragment of a protein.

Fragments of proteins or peptides as defined herein (e.g. as encoded by the inventive nucleic acid sequence as defined herein) may also comprise epitopes of those proteins or peptides. T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form. B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

"Variants" of proteins or peptides as defined in the context of the present invention may be encoded by the inventive nucleic acid sequence as defined herein. Thereby, a protein or peptide may be generated, having an amino acid sequence which differs from the original sequence in one or more mutation(s) (2, 3, 4, 5, 6, 7, or more), such as one or more substituted, inserted and/or deleted amino acid(s). The preferred level of sequence identity of "variants" in view of the full-length protein sequence is typically as indicated herein. Preferably, these fragments and/or variants have the same biological function or specific activity or at least retain an activity of the natural full-length protein of at least 50%, more preferably at least 70%, even more preferably at least 90% (as measured in an appropriate functional assay, e.g. by quantification of the organism's B-cell immune response) compared to the full-length native peptide or protein, e.g. its specific antigenic property. Accordingly, in a preferred embodiment, the "variant" is a variant of the full-length antigenic protein, which exerts antigenic properties on the immune system to the extent as described herein.

"Variants" of proteins or peptides as defined in the context of the present invention (e.g. as encoded by a nucleic acid as defined herein) may comprise conservative amino acid substitution(s) compared to their native, i.e. non-mutated physiological, sequence. Those amino acid sequences as well as their encoding nucleotide sequences in particular fall under the term variants as defined herein. Substitutions in which amino acids, which originate from the same class, are exchanged for one another are called conservative substitutions. In particular, these are amino acids having aliphatic side chains, positively or negatively charged side chains, aromatic groups in the side chains or amino acids, the side chains of which can enter into hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Insertions and substitutions are possible, in particular, at those sequence positions which cause no modification to the three-dimensional structure or do not affect the binding region. Modifications to a three-dimensional structure by insertion(s) or deletion(s) can easily be determined e.g. using CD spectra (circular dichroism spectra) (Urry, 1985, Absorption, Circular Dichroism and ORD of Polypeptides, in: Modern Physical Methods in Biochemistry, Neuberger et al. (ed.), Elsevier, Amsterdam).

Furthermore, variants of proteins or peptides as defined herein, which may be encoded by the inventive nucleic acid sequence as defined herein, may also comprise those sequences, wherein nucleotides of the nucleic acid are exchanged according to the degeneration of the genetic code, without leading to an alteration of the respective amino acid sequence of the protein or peptide, i.e. the amino acid sequence or at least part thereof may not differ from the original sequence in one or more mutation(s) within the above meaning.

In order to determine the percentage to which two sequences are identical, e.g. nucleic acid sequences or amino acid sequences as defined herein, preferably the amino acid sequences encoded by the inventive nucleic acid sequence as defined herein or the amino acid sequences themselves, the sequences can be aligned in order to be subsequently compared to one another. Therefore, e.g. a position of a first sequence may be compared with the corresponding position of the second sequence. If a position in the first sequence is occupied by the same component as is the case at a position in the second sequence, the two sequences are identical at this position. If this is not the case, the sequences differ at this position. If insertions occur in the second sequence in comparison to the first sequence, gaps can be inserted into the first sequence to allow a further alignment. If deletions occur in the second sequence in comparison to the first sequence, gaps can be inserted into the second sequence to allow a further alignment. The percentage to which two sequences are identical is then a function of the number of identical positions divided by the total number of positions including those positions which are only occupied in one sequence. The percentage to which two sequences are identical can be determined using a mathematical algorithm. A preferred, but not limiting, example of a mathematical algorithm which can be used is the algorithm of Karlin et al. (1993), PNAS USA, 90:5873-5877 or Altschul et al. (1997), Nucleic Acids Res., 25:3389-3402. Such an algorithm is integrated in the BLAST program. Sequences which are identical to the sequences of the present invention to a certain extent can be identified by this program.

The inventive nucleic acid sequence as defined herein may encode derivatives of a peptide or protein. Such a derivative of a peptide or protein is a molecule that is derived from another molecule, such as said peptide or protein. A "derivative" typically contains the full-length sequence of the natural peptide or protein and additional sequence features, e.g. at the N- or at the C-terminus, which may exhibit an additional function to the natural full-length peptide/protein. Again such derivatives have the same biological function or specific activity or at least retain an activity of the natural full length protein of at least 50%, more preferably at least 70%, even more preferably at least 90% (as measured in an appropriate functional assay), e.g. its specific antigenic property. Thereby, a "derivative" also encompasses (chimeric) fusion proteins/peptides comprising a peptide or protein used in the present invention or a natural full-length protein (or a variant or fragment thereof) fused to a distinct peptide/protein awarding e.g. two or more biological functions to the fusion peptide/protein. For example, the fusion comprises a label, such as, for example, an epitope, e.g., a FLAG epitope or a V5 epitope or an HA epitope. For example, the epitope is a FLAG epitope. Such a tag is useful for, for example, purifying the fusion protein.

In this context, a "variant" of a protein or peptide may have at least 70%, 75%, 80%, 85%, 90%, 95%, 98% or 99% amino acid identity over a stretch of 10, 20, 30, 50, 75 or 100 amino acids of such protein or peptide. Analogously, a "variant", or particularly, a "fragment" of a nucleic acid sequence may have at least 70%, 75%, 80%, 85%, 90%, 95%, 98% or 99% nucleotide identity over a stretch of 10, 20, 30, 50, 75 or 100 nucleotide of such nucleic acid sequence; typically, however, referring to the naturally occurring full-length sequences. In case of "fragments" typically, sequence identity is determined for the fragment over length (of the fragment) on the portion of the full-length protein (reflecting the same length as the fragment), which exhibits the highest level of sequence identity.

In a further preferred embodiment of the first aspect of the present invention the inventive nucleic acid sequence is associated with a vehicle, transfection or complexation agent for increasing the transfection efficiency and/or the immunostimulatory properties of the inventive nucleic acid sequence. Particularly preferred agents in this context suitable for increasing the transfection efficiency are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, pIsl, FGF, Lactoferrin, Transportan, Buforin-2, Bac715-24, SynB, SynB(1), pVEC, hCT-derived peptides, SAP, or histones. Additionally, preferred cationic or polycationic proteins or peptides may be selected from the following proteins or peptides having the following total formula: $(Arg)_l;(Lys)_m;(His)_n;(Orn)_o;(Xaa)_x$, wherein 1+m+n+o+x=8-15, and 1, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. Further preferred cationic or polycationic compounds, which can be used as transfection agent may include cationic polysaccharides, for example chitosan, polybrene, cationic polymers, e.g. polyethyleneimine (PEI), cationic lipids, e.g. DOTMA: [1-(2,3-sioleyloxy)propyl]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl] trimethylammonium, CLIPS: rac-[2(2,3-dihexadecyloxypropyl-oxysuccinyloxy) ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g polyethyleneglycole); etc.

In this context it is particularly preferred that the inventive nucleic acid is complexed at least partially with a cationic or polycationic compound, preferably cationic proteins or peptides. Partially means that only a part of the inventive nucleic acid is complexed with a cationic or polycationic compound and that the rest of the inventive nucleic acid is in uncomplexed form ("free"). Preferably the ratio of complexed nucleic acid to:free nucleic acid is selected from a range. of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed nucleic acid to free nucleic acid is selected from a ratio of about 1:1 (w/w).

It is preferred that the nucleic acid sequence of the invention is provided in either naked form or complexed, e.g. by polycationic compounds of whatever chemical structure, preferably polycationic (poly)peptides or synthetic polycationic compounds. Preferably, the nucleic acid sequence is not provided together with a packaging cell.

In a further aspect the invention provides for a composition or kit or kit of parts comprising a plurality or more than one, preferably 2 to 10, more preferably 2 to 5, most preferably 2 to 4 of the of inventive nucleic acid sequences as defined herein. These inventive compositions comprise more than one inventive nucleic acid sequences, preferably encoding different peptides or proteins which comprise preferably different pathogenic antigens or fragments, variants or derivatives thereof.

According to a further aspect, the present invention also provides a method for increasing the expression of an encoded peptide or protein comprising the steps, e.g. a) providing the inventive nucleic acid sequence as defined herein or the inventive composition comprising a plurality of inventive nucleic acid sequences as defined herein, b) applying or administering the inventive nucleic acid sequence as defined herein or the inventive composition comprising a plurality of inventive nucleic acid sequences as defined herein to an expression system, e.g. to a cell-free expression system, a cell (e.g. an expression host cell or a somatic cell), a tissue or an organism. The method may be applied for laboratory, for research, for diagnostic, for commercial production of peptides or proteins and/or for therapeutic purposes. In this context, typically after preparing the inventive nucleic acid sequence as defined herein or of the inventive composition comprising a plurality of inventive nucleic acid sequences as defined herein, it is typically applied or administered to a cell-free expression system, a cell (e.g. an expression host cell or a somatic cell), a tissue or an organism, e.g. in naked or complexed form or as a pharmaceutical composition or vaccine as described herein, preferably via transfection or by using any of the administration modes as described herein. The method may be carried out in vitro, in vivo or ex vivo. The method may furthermore be carried out in the context of the treatment of a specific disease, particularly in the treatment of infectious diseases, preferably as defined herein.

In this context in vitro is defined herein as transfection or transduction of the inventive nucleic acid as defined herein or of the inventive composition comprising a plurality of inventive nucleic acid sequences as defined herein into cells in culture outside of an organism; in vivo is defined herein as transfection or transduction of the inventive nucleic acid or of the inventive composition comprising a plurality of inventive nucleic acid sequences into cells by application of the inventive nucleic acid or of the inventive composition to the whole organism or individual and ex vivo is defined herein as transfection or transduction of the inventive nucleic acid or of the inventive composition comprising a plurality of inventive nucleic acid sequences into cells outside of an organism or individual and subsequent application of the transfected cells to the organism or individual.

Likewise, according to another aspect, the present invention also provides the use of the inventive nucleic acid sequence as defined herein or of the inventive composition comprising a plurality of inventive nucleic acid sequences as defined herein, preferably for diagnostic or therapeutic purposes, for increasing the expression of an encoded peptide or protein, e.g. by applying or administering the inventive nucleic acid sequence as defined herein or of the inventive composition comprising a plurality of inventive nucleic acid sequences as defined herein, e.g. to a cell-free expression system, a cell (e.g. an expression host cell or a somatic cell), a tissue or an organism. The use may be applied for laboratory, for research, for diagnostic for commercial production of peptides or proteins and/or for therapeutic purposes. In this context, typically after preparing the inventive nucleic acid sequence as defined herein or of the inventive composition comprising a plurality of inventive nucleic acid sequences as defined herein, it is typically applied or administered to a cell-free expression system, a cell (e.g. an expression host cell or a somatic cell), a tissue or an organism, preferably in naked form or complexed form, or as a pharmaceutical composition or vaccine as described herein, preferably via transfection or by using any of the administration modes as described herein. The use may be carried out in vitro, in vivo or ex vivo. The use may furthermore be carried out in the context of the treatment of a specific disease, particularly in the treatment of infectious diseases, preferably as defined herein.

In yet another aspect the present invention also relates to an inventive expression system comprising an inventive nucleic acid sequence or expression vector or plasmid according to the first aspect of the present invention. In this context the expression system may be a cell-free expression system (e.g. an in vitro transcription/translation system), a cellular expression system (e g mammalian cells like CHO cells, insect cells, yeast cells, bacterial cells like $E.\ coli$) or organisms used for expression of peptides or proteins (e.g. plants or animals like cows).

Additionally, according to another aspect, the present invention also relates to the use of the inventive nucleic acid as defined herein or of the inventive composition comprising a plurality of inventive nucleic acid sequences (which means typically more than 1, 2, 3, 4, 5, 6 or more than 10 nucleic acids, e.g. 2 to 10, preferably 2 to 5 nucleic acids) as defined herein for the preparation of a pharmaceutical composition for increasing the expression of an encoded peptide or protein, e.g. for treating a infectious disease, preferably as defined herein, e.g. applying or administering the inventive nucleic acid as defined herein or of the inventive composition comprising a plurality of inventive nucleic acid sequences as defined herein to a cell (e.g. an expression host cell or a somatic cell), a tissue or an organism, preferably in naked form or complexed form or as a pharmaceutical composition or vaccine as described herein, more preferably using any of the administration modes as described herein.

Accordingly, in a particular preferred aspect, the present invention also provides a pharmaceutical composition, comprising an inventive nucleic acid as defined herein or an inventive composition comprising a plurality of inventive nucleic acid sequences as defined herein and optionally a pharmaceutically acceptable carrier and/or vehicle.

As a first ingredient, the inventive pharmaceutical composition comprises at least one inventive nucleic acid as defined herein.

As a second ingredient the inventive pharmaceutical composition may optional comprise at least one additional pharmaceutically active component. A pharmaceutically active component in this connection is a compound that has a therapeutic effect to heal, ameliorate or prevent a particular indication or disease as mentioned herein, preferably infectious diseases. Such compounds include, without implying any limitation, peptides or proteins, preferably as defined herein, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc.

Furthermore, the inventive pharmaceutical composition may comprise a pharmaceutically acceptable carrier and/or vehicle. In the context of the present invention, a pharmaceutically acceptable carrier typically includes the liquid or non-liquid basis of the inventive pharmaceutical composition. If the inventive pharmaceutical composition is provided in liquid form, the carrier will typically be pyrogen-free water; isotonic saline or buffered (aqueous) solutions, e.g phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well for the inventive pharmaceutical composition, which are suitable for administration to a patient to be treated. The term "compatible" as used here means that these constituents of the inventive pharmaceutical composition are capable of being mixed with the inventive nucleic acid as defined herein in such a manner that no interaction occurs which would substantially reduce the pharmaceutical effectiveness of the inventive pharmaceutical composition under typical use conditions.

According to a specific embodiment, the inventive pharmaceutical composition may comprise an adjuvant. In this context, an adjuvant may be understood as any compound, which is suitable to initiate or increase an immune response of the innate immune system, i.e. a non-specific immune response. With other words, when administered, the inventive pharmaceutical composition preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e g an adjuvant protein as defined above or an adjuvant as defined in the following.

Particularly preferred as adjuvants suitable for depot and delivery are cationic or polycationic compounds as defined above for the inventive nucleic acid sequence as vehicle, transfection or complexation agent.

The inventive pharmaceutical composition can additionally contain one or more auxiliary substances in order to increase its immunogenicity or immunostimulatory capacity, if desired. A synergistic action of the inventive nucleic acid sequence as defined herein and of an auxiliary substance, which may be optionally contained in the inventive pharmaceutical composition, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

Further additives which may be included in the inventive pharmaceutical composition are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive pharmaceutical composition can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

The inventive pharmaceutical composition may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the inventive pharmaceutical composition may be administered by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or via infusion techniques. Particularly preferred is intradermal and intramuscular injection. Sterile injectable forms of the inventive pharmaceutical compositions may be aqueous or oleaginous suspension. These suspensions may be formulated according to techniques known in the art using suitable dispersing or wetting agents and suspending agents.

The inventive pharmaceutical composition as defined herein may also be administered orally in any orally acceptable dosage form including, but not limited to, capsules, tablets, aqueous suspensions or solutions.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive nucleic acid as defined herein suspended or dissolved in one or more carriers.

The inventive pharmaceutical composition typically comprises a "safe and effective amount" of the components of the inventive pharmaceutical composition, particularly of the inventive nucleic acid sequence(s) as defined herein. As used herein, a "safe and effective amount" means an amount of the inventive nucleic acid sequence(s) as defined herein as such that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment.

The inventive pharmaceutical composition may be used for human and also for veterinary medical purposes, preferably for human medical purposes, as a pharmaceutical composition in general or as a vaccine.

According to another particularly preferred aspect, the inventive pharmaceutical composition (or the inventive nucleic acid sequence as defined herein or the inventive composition comprising a plurality of inventive nucleic acid sequences as defined herein) may be provided or used as a vaccine. Typically, such a vaccine is as defined above for pharmaceutical compositions. Additionally, such a vaccine typically contains the inventive nucleic acid as defined herein or the inventive composition comprising a plurality of inventive nucleic acid sequences as defined herein.

The inventive vaccine may also comprise a pharmaceutically acceptable carrier, adjuvant, and/or vehicle as defined herein for the inventive pharmaceutical composition. In the specific context of the inventive vaccine, the choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines may be administered by an intradermal, subcutaneous, or intramuscular route. Inventive vaccines are therefore preferably formulated in liquid (or sometimes in solid) form.

The inventive vaccine can additionally contain one or more auxiliary substances in order to increase its immunogenicity or immunostimulatory capacity, if desired. Particularly preferred are adjuvants as auxiliary substances or additives as defined for the pharmaceutical composition.

The present invention furthermore provides several applications and uses of the inventive nucleic acid sequence as defined herein, of the inventive composition comprising a plurality of inventive nucleic acid sequences as defined herein, of the inventive pharmaceutical composition, of the inventive vaccine, all comprising the inventive nucleic acid sequence as defined herein or of kits comprising same.

According to one specific aspect, the present invention is directed to the first medical use of the inventive nucleic acid sequence as defined herein or of the inventive composition comprising a plurality of inventive nucleic acid sequences as defined herein as a medicament, preferably as a vaccine particularly in the treatment of infectious diseases.

According to another aspect, the present invention is directed to the second medical use of the inventive nucleic acid sequence as defined herein or of the inventive composition comprising a plurality of inventive nucleic acid sequences as defined herein, for the treatment of infectious diseases as defined herein, preferably to the use of the inventive nucleic acid sequence as defined herein, of the inventive composition comprising a plurality of inventive nucleic acid sequences as defined herein, of a pharmaceutical composition or vaccine comprising same or of kits comprising same for the preparation of a medicament for the prophylaxis, treatment and/or amelioration of infectious diseases as defined herein. Preferably, the pharmaceutical composition or a vaccine is used or to be administered to a patient in need thereof for this purpose.

Preferably, infectious diseases as mentioned herein are preferably selected from viral, bacterial, protozoological and prion infectious diseases. Such infectious diseases are typically selected from the list consisting of *Acinetobacter* infections, African sleeping sickness (African trypanosomiasis), AIDS (Acquired immunodeficiency syndrome), Amoebiasis, Anaplasmosis, Anthrax, Appendicitis, *Arcanobacterium haemolyticum* infections, Argentine hemorrhagic fever, Ascariasis, Aspergillosis, Astrovirus infections, Athlete's foot, Babesiosis, *Bacillus cereus* infections, Bacterial meningitis, Bacterial pneumonia, Bacterial vaginosis (B V), *Bacteroides* infections, Balantidiasis, *Baylisascaris* infections, Bilharziosis, BK virus infections, Black *piedra*, *Blastocystis hominis* infections, Blastomycosis, Bolivian hemorrhagic fever, *Borrelia* infections (Borreliosis), Botulism (and Infant botulism), Bovine tapeworm, Brazilian hemorrhagic fever, Brucellosis, *Burkholderia* infections, Buruli ulcer, Calicivirus infections (Norovirus and Sapovirus), Campylobacteriosis, Candidiasis (Candidosis), Canine tapeworm infections, Cat-scratch disease, Chagas Disease (American trypanosomiasis), Chancroid, Chickenpox, *Chlamydia* infections, *Chlamydia trachomatis* infections, *Chlamydophila pneumoniae* infections, Cholera, Chromoblastomycosis, Climatic bubo, Clonorchiasis, *Clostridium difficile* infections, Coccidioidomycosis, Cold, Colorado tick fever (CTF), Common cold (Acute viral rhinopharyngitis; Acute coryza), Condyloma *acuminata*, Conjunctivitis, Creutzfeldt-Jakob disease (CJD), Crimean-Congo hemorrhagic fever (CCHF), Cryptococcosis, Cryptosporidiosis, Cutaneous larva migrans (CLM), Cutaneous Leishmaniosis, Cyclosporiasis, Cysticercosis, Cytomegalovirus infections, Dengue fever, Dermatophytosis, Dientamoebiasis, Diphtheria, Diphyllobothriasis, Donavanosis, Dracunculiasis, Early summer meningoencephalitis (FSME), Ebola hemorrhagic fever, Echinococcosis, Ehrlichiosis, Enterobiasis (Pinworm infections), *Enterococcus* infections, Enterovirus infections, Epidemic typhus, Epiglottitis, Epstein-Barr Virus Infectious Mononucleosis, Erythema infectiosum (Fifth disease), Exanthem subitum, Fasciolopsiasis, Fasciolosis, Fatal familial insomnia (FFI), Fifth disease, Filariasis, Fish poisoning (Ciguatera), Fish tapeworm, Flu, Food poisoning by *Clostridium perfringens*, Fox tapeworm, Free-living amebic infections, *Fusobacterium* infections, Gas gangrene, Geotrichosis, Gerstmann-Sträussler-Scheinker syndrome (GSS), Giardiasis, Glanders, Gnathostomiasis, Gonorrhea, Granuloma inguinale (Donovanosis), Group A streptococcal infections, Group B streptococcal infections, *Haemophilus influenzae* infections, Hand foot and mouth disease (HFMD), Hantavirus Pulmonary Syndrome (HPS), *Helicobacter pylori* infections, Hemolytic-uremic syndrome (HUS), Hemorrhagic fever with renal syndrome (HFRS), Henipavirus infections, Hepatitis A, Hepatitis B, Hepatitis C, Hepatitis D, Hepatitis E, Herpes simplex, Herpes simplex type I, Herpes simplex type II, Herpes zoster, Histoplasmosis, Hollow warts, Hookworm infections, Human bocavirus infections, Human *ewingii* ehrlichiosis, Human granulocytic anaplasmosis (HGA), Human metapneumovirus infections, Human monocytic ehrlichiosis, Human papillomavirus (HPV) infections, Human parainfluenza virus infections, Hymenolepiasis, Influenza, Isosporiasis, Japanese encephalitis, Kawasaki disease, Keratitis, Kingella kingae infections, Kuru, Lambliasis (Giardiasis), Lassa fever, Legionellosis (Legionnaires' disease, Pontiac fever), Leishmaniasis, Leprosy, Leptospirosis, Lice, Listeriosis, Lyme borreliosis, Lyme disease, Lymphatic filariasis (Elephantiasis), Lymphocytic choriomeningitis, Malaria, Marburg hemorrhagic fever (MHF), Marburg virus, Measles, Melioidosis (Whitmore's disease), Meningitis, Meningococcal disease, Metagonimiasis, Microsporidiosis, Miniature tapeworm, Miscarriage (prostate inflammation), Molluscum contagiosum (MC), Mononucleosis, Mumps, Murine typhus (Endemic typhus), Mycetoma, *Mycoplasma hominis, Mycoplasma* pneumonia, Myiasis, Nappy/diaper dermatitis, Neonatal conjunctivitis (Ophthalmia neonatorum), Neonatal sepsis (Chorioamnionitis), Nocardiosis, Noma, Norwalk virus infections, Onchocerciasis (River blindness), Osteomyelitis, Otitis media, Paracoccidioidomycosis (South American blastomycosis), Paragonimiasis, Paratyphus, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Pfeiffer's glandular fever, Plague, Pneumococcal infections, *Pneumocystis* pneumonia (PCP), Pneumonia, Polio (childhood lameness), Poliomyelitis, Porcine tapeworm, *Prevotella* infections, Primary amoebic meningoencephalitis (PAM), Progressive multifocal leukoencephalopathy, Pseudo-croup, Psittacosis, Q fever, Rabbit fever, Rabies, Rat-bite fever, Reiter's syndrome, Respiratory syncytial virus infections (RSV), Rhinosporidiosis, Rhinovirus infections, Rickettsial infections, Rickettsialpox, Rift Valley fever (RVF), Rocky mountain spotted fever (RMSF), Rotavirus infections, Rubella, *Salmonella* paratyphus, *Salmonella* typhus, *Salmonellosis*, SARS (Severe Acute Respiratory Syndrome), Scabies, Scarlet fever, Schistosomiasis (Bilharziosis), Scrub typhus, Sepsis, Shigellosis (Bacillary dysentery), Shingles, Smallpox (Variola), Soft chancre, Sporotrichosis, Staphylococcal food poisoning, Staphylococcal infections, Strongyloidiasis, Syphilis, Taeniasis, Tetanus, Three-day fever, Tick-borne encephalitis, Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea *versicolor* (*Pityriasis versicolor*), Toxocariasis (Ocular Larva Migrans (OLM) and Visceral Larva Migrans (VLM)), Toxoplasmosis, Trichinellosis, Trichomoniasis, Trichuriasis (Whipworm infections), Tripper, Trypanosomiasis (sleeping sickness), Tsutsugamushi disease, Tuberculosis, Tularemia, Typhus, Typhus fever, *Ureaplasma urealyticum* infections, Vaginitis (Colpitis), Variant Creutzfeldt-Jakob disease (vCJD, nvCJD), Venezuelan equine encephalitis, Venezuelan hemorrhagic fever, Viral pneumonia, Visceral Leishmaniosis, Warts, West Nile Fever, Western equine encephalitis, White piedra (Tinea blanca), Whooping cough, Yeast fungus spots, Yellow fever, *Yersinia pseudotuberculosis* infections, Yersiniosis, and Zygomycosis.

In a further preferred aspect, the inventive nucleic acid sequence as defined herein or the inventive composition comprising a plurality of inventive nucleic acid sequences as defined herein may be used for the preparation of a pharmaceutical composition or a vaccine, particularly for purposes as defined herein.

The inventive pharmaceutical composition or vaccine may furthermore be used for the treatment of a disease or a disorder, preferably of infectious diseases as defined herein.

According to a final aspect, the present invention also provides kits, particularly kits of parts. Such kits, particularly kits of parts, typically comprise as components alone or in combination with further components as defined herein at least one inventive nucleic acid sequence as defined herein, the inventive pharmaceutical composition or vaccine comprising the inventive nucleic acid sequence. The at least one inventive nucleic acid sequence as defined herein, is e.g. optionally in combination with further components as defined herein, whereby the at least one nucleic acid of the invention is provided separately (first part of the kit) from at least one other part of the kit comprising one or more other components. The inventive pharmaceutical composition and/or the inventive vaccine may e.g. occur in one or different parts of the kit. As an example, e.g. at least one part of the kit may comprise at least one inventive nucleic acid sequence as defined herein, and at least one further part of the kit at least one other component as defined herein, e.g. at least one other part of the kit may comprise at least one pharmaceutical composition or vaccine or a part thereof, e.g. at least one part of the kit may comprise the inventive nucleic acid sequence as defined herein, at least one further part of the kit at least one other component as defined herein, at least one further part of the kit at least one component of the inventive pharmaceutical composition or vaccine or the inventive pharmaceutical composition or vaccine as a whole, and at least one further part of the kit e.g. at least one pharmaceutical carrier or vehicle, etc. In case the kit or kit of parts comprises a plurality of inventive nucleic acid sequences (which means typically more than 1, 2, 3, 4, 5, 6 or more than 10 nucleic acids, e.g. 2 to 10, preferably 2 to 5 nucleic acids), one component of the kit can comprise only one, several or all inventive nucleic acid sequences comprised in the kit. In an alternative embodiment every inventive nucleic acid sequence may be comprised in a different/separate component of the kit such that each component forms a part of the kit. Also, more than one nucleic acid may be comprised in a first component as part of the kit, whereas one or more other (second, third etc.) components (providing one or more other parts of the kit) may either contain one or more than one inventive nucleic acids, which may be identical or partially identical or different from the first component. The kit or kit of parts may furthermore contain technical instructions with information on the administration and dosage of the inventive nucleic acid sequence, the inventive pharmaceutical composition or the inventive vaccine or of any of its components or parts, e.g. if the kit is prepared as a kit of parts.

Taken together, the invention provides a nucleic acid sequence comprising or coding for
 a) a coding region, encoding at least one peptide or protein;
 b) at least one histone stem-loop, and
 c) a poly(A) sequence or a polyadenylation signal;

wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like. The invention further provides a composition or kit or kit of parts comprising at least one of such nucleic acid sequences. Further, the invention provides the use of such a nucleic acid sequence as a medicament, preferably for treatment of infectious diseases, more preferably in a pharmaceutical composition for treatment of infectious diseases comprising further an pharmaceutically acceptable carrier. Further, the invention provides a method for increasing the expression of an encoded peptide or protein comprising the steps of providing such an nucleic acid sequence or an composition containing such an nucleic acid sequence and applying or administering the nucleic acid sequence or the composition to a cell-free expression system, a cell, a tissue or and organism.

Further preferred, the invention provides a nucleic acid sequence comprising or coding for
  a) a coding region, encoding at least one peptide or protein;
  b) at least one histone stem-loop, and
  c) a poly(A) sequence or a polyadenylation signal;
wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like, more preferably wherein the pathogenic antigen is derivable from pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus. The invention further provides a composition or kit or kit of parts comprising at least one of such nucleic acid sequences. Further, the invention provides the use of such a nucleic acid sequence as a medicament, preferably for treatment of infectious diseases, more preferably in a pharmaceutical composition for treatment of infectious diseases comprising further an pharmaceutically acceptable carrier. Further, the invention provides a method for increasing the expression of an encoded peptide or protein comprising the steps of providing such an nucleic acid sequence or an composition containing such an nucleic acid sequence and applying or administering the nucleic acid sequence or the composition to a cell-free expression system, a cell, a tissue or and organism.

Further preferred, the invention provides a nucleic acid sequence comprising or coding for
  a) a coding region, encoding at least one peptide or protein;
  b) at least one histone stem-loop, and
  c) a poly(A) sequence or a polyadenylation signal;
wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like, more preferably wherein the pathogenic antigen is derivable from pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus, even more preferably the antigen is selected from HIV p24 antigen, HIV envelope proteins (Gp120, Gp41, Gp160), polyprotein GAG, negative factor protein Nef, trans-activator of transcription Tat if the infectious disease is HIV, preferably an infection with Human immunodeficiency virus. The invention further provides a composition or kit or kit of parts comprising at least one of such nucleic acid sequences. Further, the invention provides the use of such a nucleic acid sequence as a medicament, preferably for treatment of infectious diseases, more preferably in a pharmaceutical composition for treatment of infectious diseases comprising further an pharmaceutically acceptable carrier. Further, the invention provides a method for increasing the expression of an encoded peptide or protein comprising the steps of providing such an nucleic acid sequence or an composition containing such an nucleic acid sequence and applying or administering the nucleic acid sequence or the composition to a cell-free expression system, a cell, a tissue or and organism.

Further preferred, the invention provides a nucleic acid sequence comprising or coding for
  a) a coding region, encoding at least one peptide or protein;
  b) at least one histone stem-loop, and
  c) a poly(A) sequence or a polyadenylation signal;
wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like, more preferably wherein the pathogenic antigen is derivable from pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus, even more preferably the antigen is selected from major outer membrane protein MOMP, probable outer membrane protein PMPC, outer membrane complex protein B OmcB, heat shock proteins Hsp60 HSP10, protein *IncA*, proteins from the type III secretion system, ribonucleotide reductase small chain protein NrdB, plasmid protein Pgp3, chlamydial outer protein N CopN, antigen CT521, antigen CT425, antigen CT043, antigen TC0052, antigen TC0189, antigen TC0582, antigen TC0660, antigen TC0726, antigen TC0816, antigen TC0828 if the infectious disease is an infection with *Chlamydia trachomatis*. The invention further provides a composition or kit or kit of parts comprising at least one of such nucleic acid sequences. Further, the invention provides the use of such a nucleic acid sequence as a medicament, preferably for treatment of infectious diseases, more preferably in a pharmaceutical composition for treatment of infectious diseases comprising further an pharmaceutically acceptable carrier. Further, the invention provides a method for increasing the expression of an encoded peptide or protein comprising the steps of providing such an nucleic acid sequence or an composition containing such an nucleic acid sequence and applying or administering the nucleic acid sequence or the composition to a cell-free expression system, a cell, a tissue or and organism.

Further preferred, the invention provides a nucleic acid sequence comprising or coding for
  a) a coding region, encoding at least one peptide or protein;
  b) at least one histone stem-loop, and
  c) a poly(A) sequence or a polyadenylation signal;
wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like, more preferably wherein the pathogenic antigen is derivable from pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus, even more preferably the antigen is selected from pp65 antigen, membrane protein pp15, capsid-proximal tegument protein pp150, protein M45, DNA polymerase UL54, helicase UL105, glycoprotein gM, glycoprotein gN, glcoprotein H, glycoprotein B gB, protein UL83, protein UL94, protein UL99 if the infectious disease is Cytomegalovirus infection, preferably an infection with Cytomegalovirus (CMV). The invention further provides a composition or kit or kit of parts comprising at least one of such nucleic acid sequences. Further, the invention provides the use of such a nucleic acid sequence as a medicament, preferably for treatment of infectious diseases, more preferably in a pharmaceutical composition for treatment of infectious diseases comprising further a pharmaceutically acceptable carrier. Further, the invention provides a method for increasing the expression of an encoded peptide or protein comprising the steps of providing such an nucleic acid sequence or an composition containing such an nucleic acid sequence and applying or administering the nucleic acid sequence or the composition to a cell-free expression system, a cell, a tissue or and organism.

Further preferred, the invention provides a nucleic acid sequence comprising or coding for
  a) a coding region, encoding at least one peptide or protein;
  b) at least one histone stem-loop, and
  c) a poly(A) sequence or a polyadenylation signal;
wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like, more preferably wherein the pathogenic antigen is derivable from pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus, even more preferably the antigen is selected from capsid protein C, premembrane protein prM, membrane protein M, envelope protein E (domain I, domain II, domain II), protein NS1, protein NS2A, protein NS2B, protein NS3, protein NS4A, protein 2K, protein NS4B, protein NS5 if the infectious disease is Dengue fever, preferably an infection with Dengue viruses (DEN-1, DEN-2, DEN-3 and DEN-4)—Flaviviruses. The invention further provides a composition or kit or kit of parts comprising at least one of such nucleic acid sequences. Further, the invention provides the use of such a nucleic acid sequence as a medicament, preferably for treatment of infectious diseases, more preferably in a pharmaceutical composition for treatment of infectious diseases comprising further a pharmaceutically acceptable carrier. Further, the invention provides a method for increasing the expression of an encoded peptide or protein comprising the steps of providing such an nucleic acid sequence or an composition containing such an nucleic acid sequence and applying or administering the nucleic acid sequence or the composition to a cell-free expression system, a cell, a tissue or and organism.

Further preferred, the invention provides a nucleic acid sequence comprising or coding for
  a) a coding region, encoding at least one peptide or protein;
  b) at least one histone stem-loop, and
  c) a poly(A) sequence or a polyadenylation signal;
wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like, more preferably wherein the pathogenic antigen is derivable from pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus, even more preferably the antigen is selected from hepatitis B surface antigen HBsAg, Hepatitis B core antigen HbcAg, polymerase, protein Hbx, preS2 middle surface protein, surface protein L, large S protein, virus protein VP1, virus protein VP2, virus protein VP3, virus protein VP4 if the infectious disease is Hepatitis B, preferably an infection with Hepatitis B Virus (HBV). The invention further provides a composition or kit or kit of parts comprising at least one of such nucleic acid sequences. Further, the invention provides the use of such a nucleic acid sequence as a medicament, preferably for treatment of infectious diseases, more preferably in a pharmaceutical composition for treatment of infectious diseases comprising further a pharmaceutically acceptable carrier. Further, the invention provides a method for increasing the expression of an encoded peptide or protein comprising the steps of providing such an nucleic acid sequence or an composition containing such an nucleic acid sequence and applying or administering the nucleic acid sequence or the composition to a cell-free expression system, a cell, a tissue or and organism.

Further preferred, the invention provides a nucleic acid sequence comprising or coding for
  a) a coding region, encoding at least one peptide or protein;
  b) at least one histone stem-loop, and
  c) a poly(A) sequence or a polyadenylation signal;
wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like, more preferably wherein the pathogenic antigen is derivable from pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus, even more preferably the antigen is selected from replication protein E1, regulatory protein E2, protein E3, protein E4, protein E5, protein E6, protein E7, protein E8, major capsid protein L1, minor capsid protein L2 if the infectious disease is Human papillomavirus (HPV) infection, preferably an infection with Human papillomavirus (HPV). The invention further provides a composition or kit or kit of parts comprising at least one of such nucleic acid sequences. Further, the invention provides the use of such a nucleic acid sequence as a medicament, preferably for treatment of infectious diseases, more preferably in a pharmaceutical composition for treatment of infectious diseases comprising further a pharmaceutically acceptable carrier. Further, the invention provides a method for increasing the expression of an encoded peptide or protein comprising the steps of providing such an nucleic acid sequence or an composition containing such an nucleic acid sequence and applying or administering the nucleic acid sequence or the composition to a cell-free expression system, a cell, a tissue or and organism.

Further preferred, the invention provides a nucleic acid sequence comprising or coding for
  a) a coding region, encoding at least one peptide or protein;
  b) at least one histone stem-loop, and
  c) a poly(A) sequence or a polyadenylation signal;
wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like, more preferably wherein the pathogenic antigen is derivable from pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus, even more preferably the antigen is selected from fusion protein F, hemagglutinin-neuramidase HN, glycoprotein G, matrix protein M, phosphoprotein P, nucleoprotein N, polymerase L if the infectious disease is Human parainfluenza virus infection, preferably an infection with Human parainfluenza viruses (HPIV). The invention further provides a composition or kit or kit of parts comprising at least one of such nucleic acid sequences. Further, the invention provides the use of such a nucleic acid sequence as a medicament, preferably for treatment of infectious diseases, more preferably in a pharmaceutical composition for treatment of infectious diseases comprising further a pharmaceutically acceptable carrier. Further, the invention provides a method for increasing the expression of an encoded peptide or protein comprising the steps of providing such an nucleic acid sequence or an composition containing such an nucleic acid sequence and applying or administering the nucleic acid sequence or the composition to a cell-free expression system, a cell, a tissue or and organism.

Further preferred, the invention provides a nucleic acid sequence comprising or coding for
  a) a coding region, encoding at least one peptide or protein;
  b) at least one histone stem-loop, and
  c) a poly(A) sequence or a polyadenylation signal;
wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like, more preferably wherein the pathogenic antigen is derivable from pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus, even more preferably the antigen is selected from Hemagglutinin (HA), Neuraminidase (NA), Nucleoprotein (NP), M1 protein, M2 protein, NS1 protein, NS2 protein (NEP protein: nuclear export protein), PA protein, PB1 protein (polymerase basic 1 protein), PB1-F2 protein and PB2 protein (Orthomyxoviridae family, Influenza virus (flu)); nucleoprotein N, large structural protein L, phophoprotein P, matrix protein M, glycoprotein G if the infectious disease is Rabies, preferably an infection with Rabies virus; most preferably the antigen is derivable from a virus of the Orthomyxoviridae, most preferably of an Influenza virus, most preferably from Hämagglutinin (HA), Neuraminidase (NA), Nucleoprotein (NP), one or both of the matrixproteins (M1) and (M2), the polymerase proteins (PB1), (PB2), and the proteine NS1 and NS2. The invention further provides a composition or kit or kit of parts comprising at least one of such nucleic acid sequences. Further, the invention provides the use of such a nucleic acid sequence as a medicament, preferably for treatment of infectious diseases, more preferably in a pharmaceutical composition for treatment of infectious diseases comprising further a pharmaceutically acceptable carrier. Further, the invention provides a method for increasing the expression of an encoded peptide or protein comprising the steps of providing such an nucleic acid sequence or an composition containing such an nucleic acid sequence and applying or administering the nucleic acid sequence or the composition to a cell-free expression system, a cell, a tissue or and organism.

Further preferred, the invention provides a nucleic acid sequence comprising or coding for
  a) a coding region, encoding at least one peptide or protein;
  b) at least one histone stem-loop, and
  c) a poly(A) sequence or a polyadenylation signal;
wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like, more preferably wherein the pathogenic antigen is derivable from pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus, even more preferably the antigen is selected from fusionprotein F, nucleoprotein N, matrix protein M, matrix protein M2-1, matrix protein M2-2, phophoprotein P, small hydrophobic protein SH, major surface glycoprotein G, polymerase L, non-structural protein 1 NS1, non-structural protein 2 NS2 if the infectious disease is Respiratory syncytial virus infection, preferably an infection with Respiratory syncytial virus (RSV).

Further preferred, the invention provides a nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like, more preferably wherein the pathogenic antigen is derivable from pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus, even more preferably the antigen is selected from secretory antigen SssA (*Staphylococcus* genus, Staphylococcal food poisoning); secretory antigen SssA (*Staphylococcus* genus e.g. aureus, Staphylococcal infection); molecular chaperone DnaK, cell surface lipoprotein Mpt83, lipoprotein P23, phosphate transport system permease protein pstA, 14 kDa antigen, fibronectin-binding protein C FbpC1, Alanine dehydrogenase TB43, Glutamine synthetase 1, ESX-1 protein, protein CFP10, TB10.4 protein, protein MPT83, protein MTB12, protein MTB8, Rpf-like proteins, protein MTB32, protein MTB39, crystallin, heat-shock protein HSP65, protein PST-S if the infectious disease is Tuberculosis, preferably an infection with *Mycobacterium tuberculosis*. The invention further provides a composition or kit or kit of parts comprising at least one of such nucleic acid sequences. Further, the invention provides the use of such a nucleic acid sequence as a medicament, preferably for treatment of infectious diseases, more preferably in a pharmaceutical composition for treatment of infectious diseases comprising further a pharmaceutically acceptable carrier. Further, the invention provides a method for increasing the expression of an encoded peptide or protein comprising the steps of providing such an nucleic acid sequence or an composition containing such an nucleic acid sequence and applying or administering the nucleic acid sequence or the composition to a cell-free expression system, a cell, a tissue or and organism.

Further preferred, the invention provides a nucleic acid sequence comprising or coding for
a) a coding region, encoding at least one peptide or protein;
b) at least one histone stem-loop, and
c) a poly(A) sequence or a polyadenylation signal;
wherein said peptide or protein comprises a pathogenic antigen or a fragment, variant or derivative thereof particularly an antigen from a pathogen associated with infectious disease, preferably associated with an infections disease which is a bacterial infection, a viral infection, a protozoan infection, a fungal infection or the like, more preferably wherein the pathogenic antigen is derivable from pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus*, Dengue virus, *Chlamydia trachomatis*, Cytomegalovirus (CMV), Hepatitis B virus (HBV), *Mycobacterium tuberculosis*, Rabies virus, and Yellow Fever Virus, even more preferably the antigen is selected from genome polyprotein, protein E, protein M, capsid protein C, protease NS3, protein NS1, protein NS2A, protein AS2B, protein NS4A, protein NS4B, protein NS5 if the infectious disease is Yellow fever, preferably an infection with Yellow fever virus. The invention further provides a composition or kit or kit of parts comprising at least one of such nucleic acid sequences. Further, the invention provides the use of such a nucleic acid sequence as a medicament, preferably for treatment of infectious diseases, more preferably in a pharmaceutical composition for treatment of infectious diseases comprising further a pharmaceutically acceptable carrier. Further, the invention provides a method for increasing the expression of an encoded peptide or protein comprising the steps of providing such an nucleic acid sequence or an composition containing such an nucleic acid sequence and applying or administering the nucleic acid sequence or the composition to a cell-free expression system, a cell, a tissue or and organism.

In the present invention, if not otherwise indicated, different features of alternatives and embodiments may be combined with each other. Furthermore, the term "comprising" shall not be construed as meaning "consisting of", if not specifically mentioned. However, in the context of the present invention, term "comprising" may be substituted with the term "consisting of", where applicable.

BRIEF DESCRIPTION OF THE DRAWINGS

The following Figures are intended to illustrate the invention further and shall not be construed to limit the present invention thereto.

FIG. 1: shows the histone stem-loop consensus sequence generated from metazoan and protozoan stem loop sequences (as reported by Dávila López, M., & Samuelsson, T. (2008), RNA (New York, N.Y.), 14(1), 1-10. doi:10.1261/rna.782308). 4001 histone stem-loop sequences from metazoa and protozoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 3: shows the histone stem-loop consensus sequence generated from metazoan stem loop sequences (as reported by Dávila López, M., & Samuelsson, T. (2008), RNA (New York, N.Y.), 14(1), 1-10. doi:10.1261/rna.782308). 3870 histone stem-loop sequences from metazoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 4: shows the histone stem-loop consensus sequence generated from vertebrate stem loop sequences (as reported by Dávila López, M., & Samuelsson, T. (2008), RNA (New York, N.Y.), 14(1), 1-10. doi:10.1261/rna.782308). 1333 histone stem-loop sequences from vertebrates were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIG. 5: shows the histone stem-loop consensus sequence generated from human (*Homo sapiens*) stem loop sequences (as reported by Dávila López, M., & Samuelsson, T. (2008), RNA (New York, N.Y.), 14(1), 1-10. doi:10.1261/rna.782308). 84 histone stem-loop sequences from humans were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

FIGS. 6 to 19: show mRNAs from in vitro transcription. Given are the designation and the sequence of mRNAs obtained by in vitro transcription. The following abbreviations are used:
  ppLuc (GC): GC-enriched mRNA sequence coding for *Photinus pyralis* luciferase
  ag: 3' untranslated region (UTR) of the alpha globin gene
  A64: poly(A)-sequence with 64 adenylates
  A120: poly(A)-sequence with 120 adenylates
  histoneSL: histone stem-loop
  aCPSL: stem loop which has been selected from a library for its specific binding of the αCP-2KL protein
  PolioCL: 5' clover leaf from Polio virus genomic RNA
  G30: poly(G) sequence with 30 guanylates
  U30: poly(U) sequence with 30 uridylates
  SL: unspecific/artificial stem-loop
  N32: unspecific sequence of 32 nucleotides Within the sequences, the following elements are highlighted: coding region (ORF) (capital letters), ag (bold), histoneSL (underlined), further distinct sequences tested (italic).

FIG. 6: shows the mRNA sequence of ppLuc(GC)-ag (SEQ ID NO: 43). By linearization of the original vector at the restriction site immediately following the alpha-globin 3'-UTR (ag), mRNA is obtained lacking a poly(A) sequence.

FIG. 7: shows the mRNA sequence of ppLuc(GC)-ag-A64 (SEQ ID NO: 44). By linearization of the original vector at the restriction site immediately following the A64 poly(A)-sequence, mRNA is obtained ending with an A64 poly(A) sequence.

FIG. 8: shows the mRNA sequence of ppLuc(GC)-ag-histoneSL (SEQ ID NO: 45). The A64 poly(A) sequence was replaced by a histoneSL. The histone stem-loop sequence used in the examples was obtained from Cakmakci et al. (2008). *Molecular and Cellular Biology*, 28(3), 1182-1194.

FIG. 9: shows the mRNA sequence of ppLuc(GC)-ag-A64-histoneSL (SEQ ID NO: 46). The histoneSL was appended 3' of A64 poly(A).

FIG. 10: shows the mRNA sequence of ppLuc(GC)-ag-A120 (SEQ ID NO: 47). The A64 poly(A) sequence was replaced by an A120 poly(A) sequence.

FIG. 11: shows the mRNA sequence of ppLuc(GC)-ag-A64-ag (SEQ ID NO: 48). A second alpha-globin 3'-UTR was appended 3' of A64 poly(A).

FIG. 12: shows the mRNA sequence of ppLuc(GC)-ag-A64-aCPSL (SEQ ID NO: 49). A stem loop was appended 3' of A64 poly(A). The stem loop has been selected from a library for its specific binding of the αCP-2KL protein (Thisted et al., (2001), The Journal of Biological Chemistry, 276(20), 17484-17496). αCP-2KL is an isoform of αCP-2, the most strongly expressed αCP protein (alpha-globin mRNA poly(C) binding protein) (Makeyev et al., (2000), Genomics, 67(3), 301-316), a group of RNA binding proteins, which bind to the alpha-globin 3'-UTR (Chkheidze et al., (1999), Molecular and Cellular Biology, 19(7), 4572-4581).

FIG. 13: shows the mRNA sequence of ppLuc(GC)-ag-A64-PolioCL (SEQ ID NO: 50). The 5' clover leaf from Polio virus genomic RNA was appended 3' of A64 poly(A).

FIG. 14: shows the mRNA sequence of ppLuc(GC)-ag-A64-G30 (SEQ ID NO: 51) A stretch of 30 guanylates was appended 3' of A64 poly(A).

FIG. 15: shows the mRNA sequence of ppLuc(GC)-ag-A64-U30 (SEQ ID NO: 52) A stretch of 30 uridylates was appended 3' of A64 poly(A).

FIG. 16: shows the mRNA sequence of ppLuc(GC)-ag-A64-SL (SEQ ID NO: 53) A stem loop was appended 3' of A64 poly(A). The upper part of the stem and the loop were taken from (Babendure et al., (2006), RNA (New York, N.Y.), 12(5), 851-861). The stem loop consists of a 17 base pair long, CG-rich stem and a 6 base long loop.

FIG. 17: shows ppLuc(GC)-ag-A64-N32 (SEQ ID NO: 54) By linearization of the original vector at an alternative restriction site, mRNA is obtained with 32 additional nucleotides following poly(A).

FIG. 18: shows the mRNA sequence of HA (H1N1/PR8) (GC)-ag-A64-C30 (SEQ ID NO: 55)

FIG. 19: shows the mRNA sequence of HA (H1N1/PR8) (GC)-ag-A64-C30-histoneSL (SEQ ID NO: 56)

EXAMPLES

Figure 2:
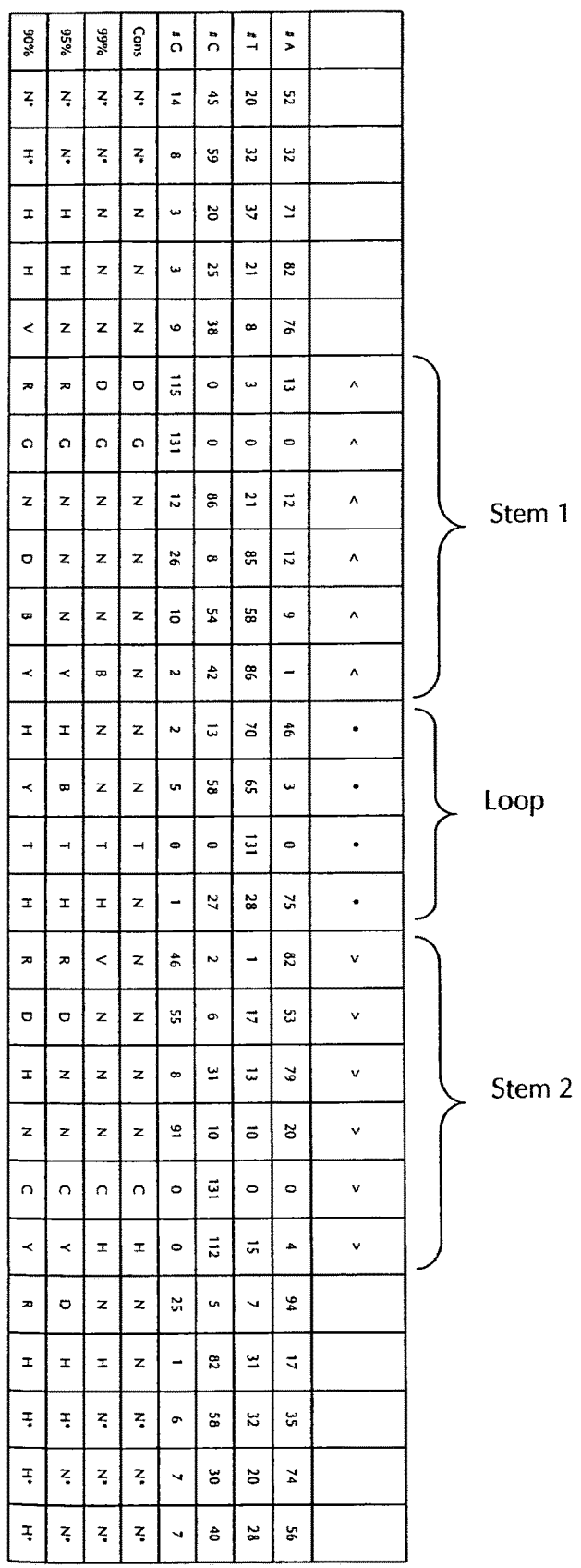
FIG. 2: shows the histone stem-loop consensus sequence generated from protozoan stem loop sequences (as reported by Dávila López, M., & Samuelsson, T. (2008), RNA (New York, N.Y.), 14(1), 1-10. doi:10.1261/rna.782308). 131 histone stem-loop sequences from protozoa were aligned and the quantity of the occurring nucleotides is indicated for every position in the stem-loop sequence. The generated consensus sequence representing all nucleotides present in the sequences analyzed is given using the single-letter nucleotide code. In addition to the consensus sequence, sequences are shown representing at least 99%, 95% and 90% of the nucleotides present in the sequences analyzed.

The following Examples are intended to illustrate the invention further and shall not be construed to limit the present invention thereto.

1. Generation of Histone-Stem-Loop Consensus Sequences

Prior to the experiments, histone stem-loop consensus sequences were determined on the basis of metazoan and protozoan histone stem-loop sequences. Sequences were taken from the supplement provided by López et al. (Dávila López, M., & Samuelsson, T. (2008), RNA (New York, N.Y.), 14(1), 1-10. doi:10.1261/rna.782308), who identified a large number of natural histone stem-loop sequences by searching genomic sequences and expressed sequence tags. First, all sequences from metazoa and protozoa (4001 sequences), or all sequences from protozoa (131 sequences) or alternatively from metazoa (3870 sequences), or from vertebrates (1333 sequences) or from humans (84 sequences) were grouped and aligned. Then, the quantity of the occurring nucleotides was determined for every position. Based on the tables thus obtained, consensus sequences for the 5 different groups of sequences were generated representing all nucleotides present in the sequences analyzed. In addition, more restrictive consensus sequences were also obtained, increasingly emphasizing conserved nucleotides 2. Preparation of DNA-Templates A vector for in vitro transcription was constructed containing a T7 promoter followed by a GC-enriched sequence coding for *Photinus pyralis* luciferase (ppLuc(GC)), the center part of the 3' untranslated region (UTR) of alpha-globin (ag), and a poly(A) sequence. The poly(A) sequence was immediately followed by a restriction site used for linearization of the vector before in vitro transcription in order to obtain mRNA ending in an A64 poly(A) sequence. mRNA obtained from this vector accordingly by in vitro transcription is designated as "ppLuc(GC)-ag-A64".

Linearization of this vector at alternative restriction sites before in vitro transcription allowed to obtain mRNA either extended by additional nucleotides 3' of A64 or lacking A64. In addition, the original vector was modified to include alternative sequences. In summary, the following mRNAs were obtained from these vectors by in vitro transcription (mRNA sequences are given in FIGS. 6 to 17):

```
                                        (SEQ ID NO: 43)
    ppLuc(GC) - ag (SEQ ID NO: 44)
    ppLuc(GC) - ag - A64

(SEQ ID NO: 45)
    ppLuc(GC) - ag - histoneSL (SEQ ID NO: 46)
    ppLuc(GC) - ag - A64 - histoneSL (SEQ ID NO: 47)
    ppLuc(GC) - ag - A120

(SEQ ID NO: 48)
    ppLuc(GC) - ag - A64 - ag (SEQ ID NO: 49)
    ppLuc(GC) - ag - A64 - aCPSL (SEQ ID NO: 50)
    ppLuc(GC) - ag - A64 - PolioCL (SEQ ID NO: 51)
    ppLuc(GC) - ag - A64 - G30
```

```
ppLuc(GC) - ag - A64 - U30        (SEQ ID NO: 52)

ppLuc(GC) - ag - A64 - SL         (SEQ ID NO: 53)

ppLuc(GC) - ag - A64 - N32        (SEQ ID NO: 54)
```

Furthermore DNA plasmid sequences coding for the pathogenic antigen HA (H1N1/PR8) was prepared accordingly as described above.

In summary, the following mRNAs were obtained from these vectors by in vitro transcription (mRNA sequences are given in FIGS. 18 to 19):

HA (H1N1/PR8) (GC)-ag-A64-C30 (SEQ ID NO: 55)
HA (H1N1/PR8) (GC)-ag-A64-C30-histoneSL (SEQ ID NO: 56)

3. In Vitro Transcription

The DNA-template according to Example 2 was linearized and transcribed in vitro using T7-Polymerase. The DNA-template was then digested by DNase-treatment. All mRNA-transcripts contained a 5'-CAP structure obtained by adding an excess of N7-Methyl-Guanosine-5'-Triphosphate-5'-Guanosine to the transcription reaction. mRNA thus obtained was purified and resuspended in water.

4. Enzymatic Adenylation of mRNA

Two mRNAs were enzymatically adenylated:
ppLuc(GC)-ag-A64 and ppLuc(GC)-ag-histoneSL.

To this end, RNA was incubated with *E. coli* Poly(A)-polymerase and ATP (Poly(A) Polymerase Tailing Kit, Epicentre, Madison, USA) following the manufacturer's instructions. mRNA with extended poly(A) sequence was purified and resuspended in water. The length of the poly(A) sequence was determined via agarose gel electrophoresis. Starting mRNAs were extended by approximately 250 adenylates, the mRNAs obtained are designated as ppLuc(GC)-ag-A300 and ppLuc(GC)-ag-histoneSL-A250, respectively.

5. Luciferase Expression by mRNA Electroporation

HeLa cells were trypsinized and washed in opti-MEM. $1 \times 10^5$ cells in 200 µl of opti-MEM each were electroporated with 0.5 µg of ppLuc-encoding mRNA. As a control, mRNA not coding for ppLuc was electroporated separately. Electroporated cells were seeded in 24-well plates in 1 ml of RPMI 1640 medium. 6, 24, or 48 hours after transfection, medium was aspirated and cells were lysed in 200 µl of lysis buffer (25 mM Tris, pH 7.5 (HCl), 2 mM EDTA, 10% glycerol, 1% Triton X-100, 2 mM DTT, 1 mM PMSF). Lysates were stored at −20° C. until ppLuc activity was measured.

6. Luciferase Expression by mRNA Lipofection

HeLa cells were seeded in 96 well plates at a density of $2 \times 10^4$ cells per well. The following day, cells were washed in opti-MEM and then transfected with 0.25 µg of Lipofectin-complexed ppLuc-encoding mRNA in 150 µl of opti-MEM. As a control, mRNA not coding for ppLuc was lipofected separately. In some wells, opti-MEM was aspirated and cells were lysed in 200 µl of lysis buffer 6 hours after the start of transfection. In the remaining wells, opti-MEM was exchanged for RPMI 1640 medium at that time. In these wells, medium was aspirated and cells were lysed in 200 µl of lysis buffer 24 or 48 hours after the start of transfection. Lysates were stored at −20° C. until ppLuc activity was measured.

7. Luciferase Measurement ppLuc activity was measured as relative light units (RLU) in a BioTek SynergyHT plate reader at 5 seconds measuring time using 50 µl of lysate and 200 µl of luciferin buffer (25 mM Glycylglycin, pH 7.8 (NaOH), 15 mM MgSO$_4$, 2 mM ATP, 75 µM luciferin). Specific RLU were calculated by subtracting RLU of the control RNA from total RLU.

8. Luciferase Expression by Intradermal mRNA Injection (Luciferase Expression In Vivo)

Mice were anaesthetized with a mixture of Rompun and Ketavet. Each ppLuc-encoding mRNA was injected intradermally (0.5 µg of mRNA in 50 µl per injection). As a control, mRNA not coding for ppLuc was injected separately. 16 hours after injection, mice were sacrificed and tissue collected. Tissue samples were flash frozen in liquid nitrogen and lysed in a tissue lyser (Qiagen) in 800 µl of lysis buffer (25 mM Tris, pH 7.5 (HCl), 2 mM EDTA, 10% glycerol, 1% Triton X-100, 2 mM DTT, 1 mM PMSF). Subsequently samples were centrifuged at 13500 rpm at 4° C. for 10 minutes. Lysates were stored at −80° C. until ppLuc activity was measured (see 7. luciferase measurement).

9. Detection of an Antigen-Specific B-Cell Immune Response (Antibodies)

Figure 24:
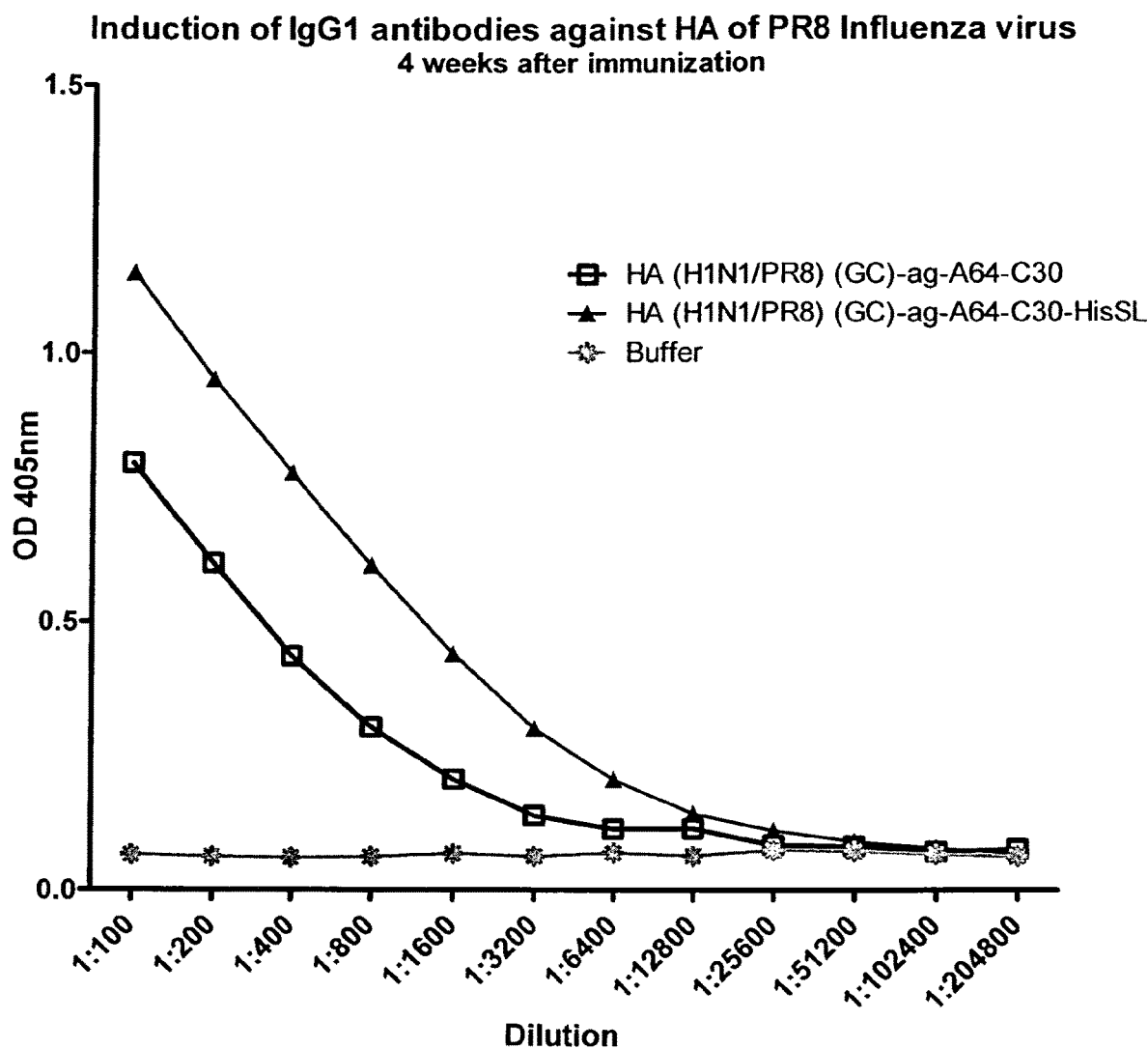
FIG. 24: shows that the combination of poly(A) and histoneSL increases the level of antibodies elicited by vaccination with mRNA. The effect of poly(A) sequence and the combination of poly(A) and histoneSL on the induction of anti HA antibodies elicited by vaccination with mRNA was examined Therefore Balb/c mice were vaccinated intradermally with different mRNAs. The level of HA-specific antibodies in vaccinated and control mice was analyzed by ELISA with serial dilutions of sera. Anti HA IgG1 is induced by mRNA having only a poly(A) sequence. Strikingly however, the combination of poly(A) and histoneSL strongly increases the anti HA IgG1 level, above the level observed with only a poly(A) sequence.

BALB/c mice (8 mice per group) were vaccinated twice within 7 days intradermally with the vaccine comprising 10 µg mRNA coding for HA (Hemagglutinin of A/Puerto Rico/8/34, according to SEQ ID NO. 55 and 56). For negative control, mice were treated with buffer. Detection of an antigen specific immune response was carried out by detecting HA protein specific antibodies. Therefore, blood samples were taken from vaccinated mice four weeks after the last vaccination and sera were prepared. MaxiSorp® plates (Nalgene Nunc International) were coated with HA protein (Charles River Laboratories). After blocking with 1×PBS containing 0.05% Tween-20 and 1% BSA the plates were incubated with diluted mouse serum (1:50). Subsequently a biotin-coupled secondary antibody (Anti-mouse-IgG Dianova, cat. #115035003) was added. After washing, the plate was incubated with Horseradish peroxidase-streptavidin and subsequently the conversion of the ABTS substrate (2,2'-azino-bis(3-ethyl-benzthiazoline-6-sulfonic acid) was measured. Results of this experiment are shown in FIG. 24.

10. Detection of an Antigen-Specific Cellular Immune Response (T Cell Immune Response) by ELISPOT:

C57BL/6 mice are vaccinated intradermally with HA encoding mRNA (Hemagglutinin of A/Puerto Rico/8/34, according to SEQ ID NO. 55 and 56). complexed with protamine (2 times in 7 days). Control mice are treated with buffer. 1 week after the last vaccination mice are sacrificed, the spleens are removed and the splenocytes are isolated. The splenocytes are restimulated for 7 days in the presence of peptides from the above antigen (peptide library) or coincubated with dendritic cells generated from bone marrow cells of native syngeneic mice, which are electroporated with mRNA coding for the antigen. To determine an antigen-specific cellular immune response INFgamma secretion was measured after re-stimulation. For detection of INFgamma a coat multiscreen plate (Millipore) is incubated overnight with coating buffer 0.1 M carbonate-bicarbonate buffer pH 9.6, 10.59 g/l Na2CO3, 8.4 g/l NaHCO$_3$) comprising antibody against INFγ (BD Pharmingen, Heidelberg, Germany) Stimulators and effector cells are incubated together in the plate in the ratio of 1:20 for 24 h. The plate is washed with 1×PBS and incubated with a biotin-coupled secondary antibody. After washing with 1×PBS/0.05% Tween-20 the substrate (5-Bromo-4-Cloro-3-Indolyl Phosphate/Nitro Blue Tetrazolium Liquid Substrate System from Sigma Aldrich, Taufkirchen, Germany) is added to the plate and the conversion of the substrate could be detected visually.

11. Results 11.1 Histone Stem-Loop Sequences:

In order to characterize histone stem-loop sequences, sequences from metazoa and protozoa (4001 sequences), or from protozoa (131 sequences) or alternatively from metazoa (3870 sequences), or from vertebrates (1333 sequences) or from humans (84 sequences) were grouped and aligned. Then, the quantity of the occurring nucleotides was determined for every position. Based on the tables thus obtained, consensus sequences for the 5 different groups of sequences were generated representing all nucleotides present in the sequences analyzed. Within the consensus sequence of metazoa and protozoa combined, 3 nucleotides are conserved, a T/U in the loop and a G and a C in the stem, forming a base pair. Structurally, typically a 6 base-pair stem and a loop of 4 nucleotides is formed. However, deviating structures are common: Of 84 human histone stem-loops, two contain a stem of only 5 nucleotides comprising 4 base-pairs and one mismatch. Another human histone stem-loop contains a stem of only 5 base-pairs. Four more human histone stem-loops contain a 6 nucleotide long stem, but include one mismatch at three different positions, respectively. Furthermore, four human histone stem-loops contain one wobble base-pair at two different positions, respectively. Concerning the loop, a length of 4 nucleotides seems not to be strictly required, as a loop of 5 nucleotides has been identified in *D. discoideum*.

In addition to the consensus sequences representing all nucleotides present in the sequences analyzed, more restrictive consensus sequences were also obtained, increasingly emphasizing conserved nucleotides. In summary, the following sequences were obtained:

(Cons): represents all nucleotides present
(99%): represents at least 99% of all nucleotides present
(95%): represents at least 95% of all nucleotides present
(90%): represents at least 90% of all nucleotides present The results of the analysis of histone stem-loop sequences are summarized in the following Tables 1 to 5 (see also FIGS. 1 to 5):

TABLE 1

Metazoan and protozoan histone stem-loop consensus sequence: (based on an alignment of 4001 metazoan and protozoan histone stem-loop sequences) (see also FIG. 1)

|  | < | < | < | < | < | < | • | • |  |  |  |  |  |
|---|---|---|---|---|---|---|---|---|---|---|---|---|---|
| # A | 2224 | 1586 | 3075 | 2872 | 1284 | 184 | 0 | 13 | 12 | 9 | 1 | 47 | 59 |
| # T | 172 | 188 | 47 | 205 | 19 | 6 | 0 | 569 | 1620 | 199 | 3947 | 3830 | 3704 |
| # C | 1557 | 2211 | 875 | 918 | 2675 | 270 | 0 | 3394 | 2342 | 3783 | 51 | 119 | 227 |
| # G | 25 | 16 | 4 | 6 | 23 | 3541 | 4001 | 25 | 27 | 10 | 2 | 5 | 11 |
| Cons | N* | N* | N | N | N | N | G | N | N | N | N | N | N |
| 99% | H* | H* | H | H | V | V | G | Y | Y | Y | Y | H | H |
| 95% | M* | H* | M | H | M | S | G | Y | Y | Y | T | T | Y |
| 90% | M* | M* | M | M | M | S | G | Y | Y | C | T | T | T |

|  | • | • | > | > | > | > | > | > |  |  |  |  |  |
|---|---|---|---|---|---|---|---|---|---|---|---|---|---|
| # A | 0 | 675 | 3818 | 195 | 1596 | 523 | 0 | 14 | 3727 | 61 | 771 | 2012 | 2499 |
| # T | 4001 | 182 | 1 | 21 | 15 | 11 | 0 | 179 | 8 | 64 | 557 | 201 | 690 |
| # C | 0 | 3140 | 7 | 50 | 31 | 16 | 4001 | 3543 | 154 | 3870 | 2636 | 1744 | 674 |
| # G | 0 | 4 | 175 | 3735 | 2359 | 3451 | 0 | 265 | 112 | 4 | 37 | 43 | 138 |
| Cons | T | N | N | N | N | N | C | N | N | N | N* | N* | N* |
| 99% | T | H | R | V | V | R | C | B | V | H | H* | N* | N* |
| 95% | T | M | A | R | R | R | C | S | M | C | H* | H* | H* |
| 90% | T | M | A | G | R | R | C | S | A | C | H* | M* | H* |

TABLE 2

Protozoan histone stem-loop consensus sequence: (based on an alignment of 131 protozoan histone stem-loop sequences) (see also FIG. 2)

|  | | | | | | < | < | < | < | < | < | • | • | • | • | > | > | > | > | > | > | | | | | |
|---|---|---|---|---|---|---|---|---|---|---|---|---|---|---|---|---|---|---|---|---|---|---|---|---|---|---|
| # A | 52 | 32 | 71 | 82 | 76 | 13 | 0 | 12 | 12 | 9 | 1 | 46 | 3 | 0 | 75 | 82 | 53 | 79 | 20 | 0 | 4 | 94 | 17 | 35 | 74 | 56 |
| # T | 20 | 32 | 37 | 21 | 8 | 3 | 0 | 21 | 85 | 58 | 86 | 70 | 65 | 131 | 28 | 1 | 17 | 13 | 10 | 0 | 15 | 7 | 31 | 32 | 20 | 28 |
| # C | 45 | 59 | 20 | 25 | 38 | 0 | 0 | 86 | 8 | 54 | 42 | 13 | 58 | 0 | 27 | 2 | 6 | 31 | 10 | 131 | 112 | 5 | 82 | 58 | 30 | 40 |
| # G | 14 | 8 | 3 | 3 | 9 | 115 | 131 | 12 | 26 | 10 | 2 | 2 | 5 | 0 | 1 | 46 | 55 | 8 | 91 | 0 | 0 | 25 | 1 | 6 | 7 | 7 |
| Cons | N* | N* | N | N | N | D | G | N | N | N | N | N | T | N | N | N | N | N | C | H | N | N | N* | N* | N* |
| 99% | N* | N* | N | N | N | D | G | N | N | N | B | N | T | H | V | N | N | N | C | H | N | H | N* | N* | N* |
| 95% | N* | N* | H | H | N | R | G | N | N | N | Y | H | B | T | H | R | D | N | N | C | Y | D | H | N* | N* |
| 90% | N* | H* | H | H | V | R | G | N | D | B | Y | H | Y | T | H | R | D | H | N | C | Y | R | H | H* | H* | H* |

TABLE 3

Metazoan histone stem-loop consensus sequence: (based on an alignment of 3870 (including 1333 vertebrate sequences) metazoan histone stem-loop sequences) (see also FIG. 3)

|  |  |  |  |  |  | < | < | < | < | < | < | • | • |
|---|---|---|---|---|---|---|---|---|---|---|---|---|---|
| # A | 2172 | 1554 | 3004 | 2790 | 1208 | 171 | 0 | 1 | 0 | 0 | 0 | 1 | 56 |
| # T | 152 | 156 | 10 | 184 | 11 | 3 | 0 | 548 | 1535 | 141 | 3861 | 3760 | 3639 |
| # C | 1512 | 2152 | 855 | 893 | 2637 | 270 | 0 | 3308 | 2334 | 3729 | 9 | 106 | 169 |
| # G | 11 | 8 | 1 | 3 | 14 | 3426 | 3870 | 13 | 1 | 0 | 0 | 3 | 6 |
| Cons | N* | N* | N | N | N | N | G | N | B | Y | Y | N | N |
| 99% | H* | H* | M | H | M | V | G | Y | Y | Y | T | Y | H |
| 95% | M* | M* | M | M | M | S | G | Y | Y | C | T | T | Y |
| 90% | M* | M* | M | M | M | S | G | Y | Y | C | T | T | T |

|  | • | • | > | > | > | > | > | > |  |  |  |  |  |
|---|---|---|---|---|---|---|---|---|---|---|---|---|---|
| # A | 0 | 600 | 3736 | 142 | 1517 | 503 | 0 | 10 | 3633 | 44 | 736 | 1938 | 2443 |
| # T | 3870 | 154 | 0 | 4 | 2 | 1 | 0 | 164 | 1 | 33 | 525 | 181 | 662 |
| # C | 0 | 3113 | 5 | 44 | 0 | 6 | 3870 | 3431 | 149 | 3788 | 2578 | 1714 | 634 |
| # G | 0 | 3 | 129 | 3680 | 2351 | 3360 | 0 | 265 | 87 | 3 | 31 | 36 | 131 |
| Cons | T | N | V | N | D | N | C | N | N | N | N* | N* | N* |
| 99% | T | H | R | V | R | R | C | B | V | M | H* | H* | N* |
| 95% | T | M | A | G | R | R | C | S | M | C | H* | H* | H* |
| 90% | T | M | A | G | R | R | C | S | A | C | H* | M* | H* |

TABLE 4

Vertebrate histone stem-loop consensus sequence: (based on an alignment of 1333 vertebrate histone stem-loop sequences) (see also FIG. 4)

|  |  |  |  |  |  | < | < | < | < | < | < | • | • |
|---|---|---|---|---|---|---|---|---|---|---|---|---|---|
| # A | 661 | 146 | 1315 | 1323 | 920 | 8 | 0 | 1 | 0 | 0 | 0 | 1 | 4 |
| # T | 63 | 121 | 2 | 2 | 6 | 2 | 0 | 39 | 1217 | 2 | 1331 | 1329 | 1207 |
| # C | 601 | 1062 | 16 | 6 | 403 | 1 | 0 | 1293 | 116 | 1331 | 2 | 0 | 121 |
| # G | 8 | 4 | 0 | 2 | 4 | 1322 | 1333 | 0 | 0 | 0 | 0 | 3 | 1 |
| Cons | N* | N* | H | N | N | N | G | H | Y | Y | Y | D | N |
| 99% | H* | H* | M | A | M | G | G | Y | Y | C | T | T | Y |
| 95% | H* | H* | A | A | M | G | G | C | Y | C | T | T | Y |
| 90% | M* | M* | A | A | M | G | G | C | T | C | T | T | T |

|  | • | • | > | > | > | > | > | > |  |  |  |  |  |
|---|---|---|---|---|---|---|---|---|---|---|---|---|---|
| # A | 0 | 441 | 1333 | 0 | 1199 | 21 | 0 | 1 | 1126 | 26 | 81 | 380 | 960 |
| # T | 1333 | 30 | 0 | 1 | 0 | 1 | 0 | 2 | 1 | 22 | 91 | 91 | 12 |
| # C | 0 | 862 | 0 | 2 | 0 | 0 | 1333 | 1328 | 128 | 1284 | 1143 | 834 | 361 |
| # G | 0 | 0 | 0 | 1330 | 134 | 1311 | 0 | 2 | 78 | 1 | 18 | 28 | 0 |
| Cons | T | H | A | B | R | D | C | N | N | N* | N* | N* | H* |
| 99% | T | H | A | G | R | R | C | C | V | H | N* | N* | M* |
| 95% | T | M | A | G | R | G | C | C | V | C | H* | H* | M* |
| 90% | T | M | A | G | R | G | C | C | M | C | Y* | M* | M* |

TABLE 5

*Homo sapiens* histone stem-loop consensus sequence: (based on an alignment of 84 human histone stem-loop sequences) (see also FIG. 5)

|  |  |  | < | < | < | < | < | < | • | • | • | • | > | > | > | > | > | > |  |  |  |  |  |
|---|---|---|---|---|---|---|---|---|---|---|---|---|---|---|---|---|---|---|---|---|---|---|---|
| # A | 10 | 17 | 84 | 84 | 76 | 1 | 0 | 1 | 0 | 0 | 0 | 1 | 0 | 0 | 12 | 84 | 0 | 65 | 3 | 0 | 0 | 69 | 5 | 0 | 10 | 64 |
| # T | 8 | 6 | 0 | 0 | 2 | 2 | 0 | 1 | 67 | 0 | 84 | 80 | 81 | 84 | 5 | 0 | 0 | 0 | 0 | 0 | 0 | 0 | 4 | 25 | 24 | 3 |
| # C | 62 | 61 | 0 | 0 | 6 | 0 | 0 | 82 | 17 | 84 | 0 | 0 | 3 | 0 | 67 | 0 | 1 | 0 | 0 | 84 | 84 | 5 | 75 | 57 | 44 | 17 |
| # G | 4 | 0 | 0 | 0 | 0 | 81 | 84 | 0 | 0 | 0 | 0 | 3 | 0 | 0 | 0 | 0 | 83 | 19 | 81 | 0 | 0 | 10 | 0 | 2 | 6 | 0 |
| Cons | N* | H* | A | A | H | D | G | H | Y | C | T | D | Y | T | H | A | S | R | R | C | C | V | H | B* | N* | H* |
| 99% | N* | H* | A | A | H | D | G | H | Y | C | T | D | Y | T | H | A | S | R | R | C | C | V | H | B* | N* | H* |
| 95% | H* | H* | A | A | M | G | G | Y | C | T | T | T | T | T | H | A | G | R | G | C | C | V | M | Y* | N* | M* |
| 90% | H* | M* | A | A | A | G | G | C | Y | C | T | T | T | T | M | A | G | R | G | C | C | R | M | Y* | H* | M* |

Wherein the used abbreviations were defined as followed:

| abbreviation | Nucleotide bases | remark |
|---|---|---|
| G | G | Guanine |
| A | A | Adenine |
| T | T | Thymine |
| U | U | Uracile |
| C | C | Cytosine |
| R | G or A | Purine |
| Y | T/U or C | Pyrimidine |
| M | A or C | Amino |
| K | G or T/U | Keto |
| S | G or C | Strong (3H bonds) |
| W | A or T/U | Weak (2H bonds) |
| H | A or C or T/U | Not G |
| B | G or T/U or C | Not A |
| V | G or C or A | Not T/U |
| D | G or A or T/U | Not C |
| N | G or C or T/U or A | Any base |
| * | present or not | Base may be present or not |

11.2 the Combination of Poly(A) and histoneSL Increases Protein Expression from mRNA in a Synergistic Manner.

Figure 20:
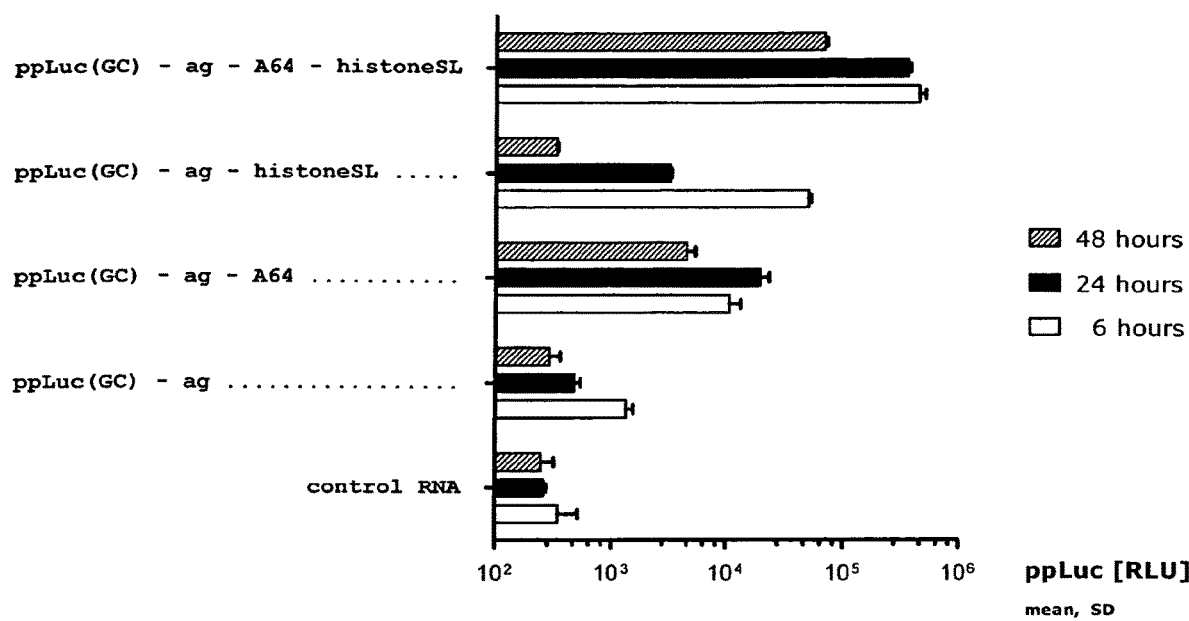
FIG. 20: shows that the combination of poly(A) and histoneSL increases protein expression from mRNA in a synergistic manner. The effect of poly(A) sequence, histoneSL, and the combination of poly(A) and histoneSL on luciferase expression from mRNA was examined Therefore different mRNAs were electroporated into HeLa cells. Luciferase levels were measured at 6, 24, and 48 hours after transfection. Little luciferase is expressed from mRNA having neither poly(A) sequence nor histoneSL. Both a poly(A) sequence or the histoneSL increase the luciferase level. Strikingly however, the combination of poly(A) and histoneSL further strongly increases the luciferase level, manifold above the level observed with either of the individual elements, thus acting synergistically. Data are graphed as mean RLU±SD (relative light units±standard deviation) for triplicate transfections. Specific RLU are summarized in Example 11.2.

To investigate the effect of the combination of poly(A) and histoneSL on protein expression from mRNA, mRNAs with different sequences 3' of the alpha-globin 3'-UTR were synthesized: mRNAs either ended just 3' of the 3'-UTR, thus lacking both poly(A) sequence and histoneSL, or contained either an A64 poly(A) sequence or a histoneSL instead, or both A64 poly(A) and histoneSL 3' of the 3'-UTR. Luciferase-encoding mRNAs or control mRNA were electroporated into HeLa cells. Luciferase levels were measured at 6, 24, and 48 hours after transfection (see following Table 6 and FIG. 20).

TABLE 6

| mRNA | RLU at 6 hours | RLU at 24 hours | RLU at 48 hours |
|---|---|---|---|
| ppLuc(GC)-ag-A64-histoneSL | 466553 | 375169 | 70735 |
| ppLuc(GC)-ag-histoneSL | 50947 | 3022 | 84 |
| ppLuc(GC)-ag-A64 | 10471 | 19529 | 4364 |
| ppLuc(GC)-ag | 997 | 217 | 42 |

Little luciferase was expressed from mRNA having neither poly(A) sequence nor histoneSL. Both a poly(A) sequence or the histoneSL increased the luciferase level to a similar extent. Either mRNA gave rise to a luciferase level much higher than did mRNA lacking both poly(A) and histoneSL. Strikingly however, the combination of poly(A) and histoneSL further strongly increased the luciferase level, manifold above the level observed with either of the individual elements. The magnitude of the rise in luciferase level due to combining poly(A) and histoneSL in the same mRNA demonstrates that they are acting synergistically.

The synergy between poly(A) and histoneSL was quantified by dividing the signal from poly(A)-histoneSL mRNA (+/+) by the sum of the signals from histoneSL mRNA (−/+) plus poly(A) mRNA (+/−) (see following Table 7).

TABLE 7

| A64 | histoneSL | RLU at 6 hours | RLU at 24 hours | RLU at 48 hours |
|---|---|---|---|---|
| + | + | 466553 | 375169 | 70735 |
| − | + | 50947 | 3022 | 84 |

TABLE 7-continued

| A64 | histoneSL | RLU at 6 hours | RLU at 24 hours | RLU at 48 hours |
|---|---|---|---|---|
| + | − | 10471 | 19529 | 4364 |
| Synergy | | 7.6 | 16.6 | 15.9 |

The factor thus calculated specifies how much higher the luciferase level from mRNA combining poly(A) and histoneSL is than would be expected if the effects of poly(A) and histoneSL were purely additive. The luciferase level from mRNA combining poly(A) and histoneSL was up to 16.6 times higher than if their effects were purely additive. This result confirms that the combination of poly(A) and histoneSL effects a markedly synergistic increase in protein expression.

11.3 the Combination of Poly(A) and histoneSL Increases Protein Expression from mRNA Irrespective of their Order.

Figure 21:
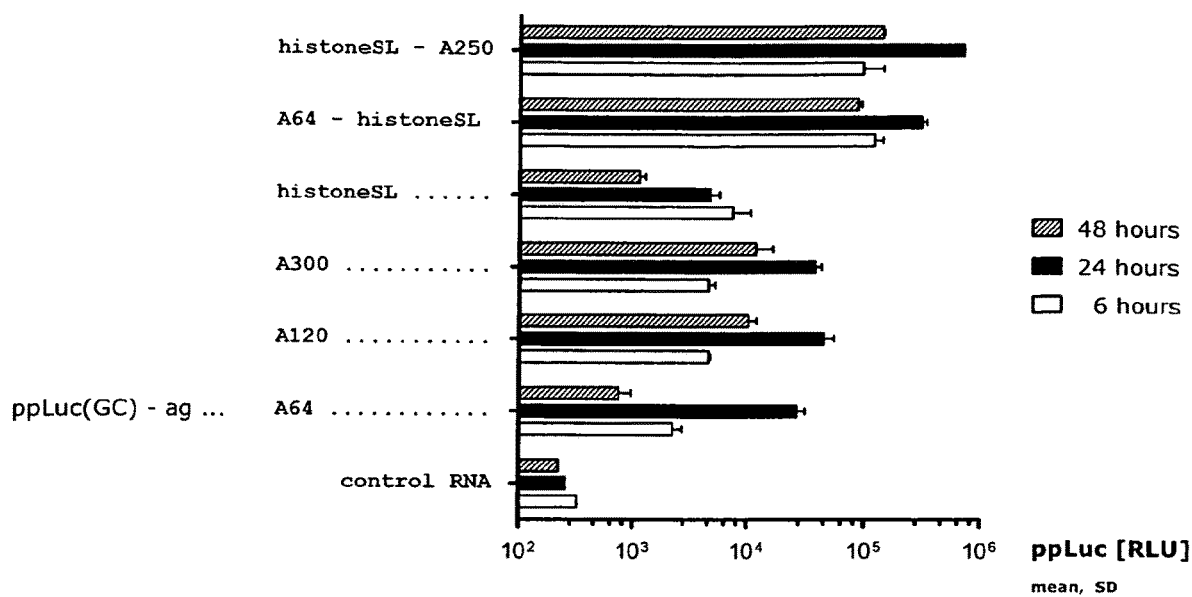
FIG. 21: shows that the combination of poly(A) and histoneSL increases protein expression from mRNA irrespective of their order. The effect of poly(A) sequence, histoneSL, the combination of poly(A) and histoneSL, and their order on luciferase expression from mRNA was examined Therefore different mRNAs were lipofected into HeLa cells. Luciferase levels were measured at 6, 24, and 48 hours after the start of transfection. Both an A64 poly(A) sequence or the histoneSL give rise to comparable luciferase levels. Increasing the length of the poly(A) sequence from A64 to A120 or to A300 increases the luciferase level moderately. In contrast, the combination of poly(A) and histoneSL increases the luciferase level much further than lengthening of the poly(A) sequence. The combination of poly(A) and histoneSL acts synergistically as it increases the luciferase level manifold above the level observed with either of the individual elements. The synergistic effect of the combination of poly(A) and histoneSL is seen irrespective of the order of poly(A) and histoneSL and irrespective of the length of poly(A) with A64-histoneSL or histoneSL-A250 mRNA. Data are graphed as mean RLU±SD for triplicate transfections. Specific RLU are summarized in Example 11.3.

The effect of the combination of poly(A) and histoneSL might depend on the length of the poly(A) sequence and the order of poly(A) and histoneSL. Thus, mRNAs with increasing poly(A) sequence length and mRNA with poly(A) and histoneSL in reversed order were synthesized: Two mRNAs contained 3' of the 3'-UTR either an A120 or an A300 poly(A) sequence. One further mRNA contained 3' of the 3'-UTR first a histoneSL followed by an A250 poly(A) sequence. Luciferase-encoding mRNAs or control mRNA were lipofected into HeLa cells. Luciferase levels were measured at 6, 24, and 48 hours after the start of transfection (see following Table 8 and FIG. 21).

TABLE 8

| mRNA | RLU at 6 hours | RLU at 24 hours | RLU at 48 hours |
|---|---|---|---|
| ppLuc(GC)-ag-histoneSL-A250 | 98472 | 734222 | 146479 |
| ppLuc(GC)-ag-A64-histoneSL | 123674 | 317343 | 89579 |
| ppLuc(GC)-ag-histoneSL | 7291 | 4565 | 916 |
| ppLuc(GC)-ag-A300 | 4357 | 38560 | 11829 |
| ppLuc(GC)-ag-A120 | 4371 | 45929 | 10142 |
| ppLuc(GC)-ag-A64 | 1928 | 26781 | 537 |

Both an A64 poly(A) sequence or the histoneSL gave rise to comparable luciferase levels. In agreement with the previous experiment did the combination of A64 and histoneSL strongly increase the luciferase level, manifold above the level observed with either of the individual elements. The magnitude of the rise in luciferase level due to combining poly(A) and histoneSL in the same mRNA demonstrates that they are acting synergistically. The synergy between A64 and histoneSL was quantified as before based on the luciferase levels of A64-histoneSL, A64, and histoneSL mRNA (see following Table 9). The luciferase level from mRNA combining A64 and histoneSL was up to 61.7 times higher than if the effects of poly(A) and histoneSL were purely additive.

TABLE 9

| | A64 | histoneSL | RLU at 6 hours | RLU at 24 hours | RLU at 48 hours |
|---|---|---|---|---|---|
| | + | + | 123674 | 317343 | 89579 |
| | − | + | 7291 | 4565 | 916 |
| | + | − | 1928 | 26781 | 537 |
| Synergy | | | 13.4 | 10.1 | 61.7 |

In contrast, increasing the length of the poly(A) sequence from A64 to A120 or to A300 increased the luciferase level only moderately (see Table 8 and FIG. 19). mRNA with the longest poly(A) sequence, A300, was also compared to mRNA in which a poly(A) sequence of similar length was combined with the histoneSL, histoneSL-A250. In addition to having a long poly(A) sequence, the order of histoneSL and poly(A) is reversed in this mRNA relative to A64-histoneSL mRNA. The combination of A250 and histoneSL strongly increased the luciferase level, manifold above the level observed with either histoneSL or A300. Again, the synergy between A250 and histoneSL was quantified as before comparing RLU from histoneSL-A250 mRNA to RLU from A300 mRNA plus histoneSL mRNA (see following Table 10). The luciferase level from mRNA combining A250 and histoneSL was up to 17.0 times higher than if the effects of poly(A) and histoneSL were purely additive.

TABLE 10

|  | histoneSL | A250/A300 | RLU at 6 hours | RLU at 24 hours | RLU at 48 hours |
|---|---|---|---|---|---|
|  | + | + | 98472 | 734222 | 146479 |
|  | + | − | 7291 | 4565 | 916 |
|  | − | + | 4357 | 38560 | 11829 |
| Synergy |  |  | 8.5 | 17.0 | 11.5 |

In summary, a highly synergistic effect of the combination of histoneSL and poly(A) on protein expression from mRNA has been demonstrated for substantially different lengths of poly(A) and irrespective of the order of poly(A) and histoneSL.

Figure 22:
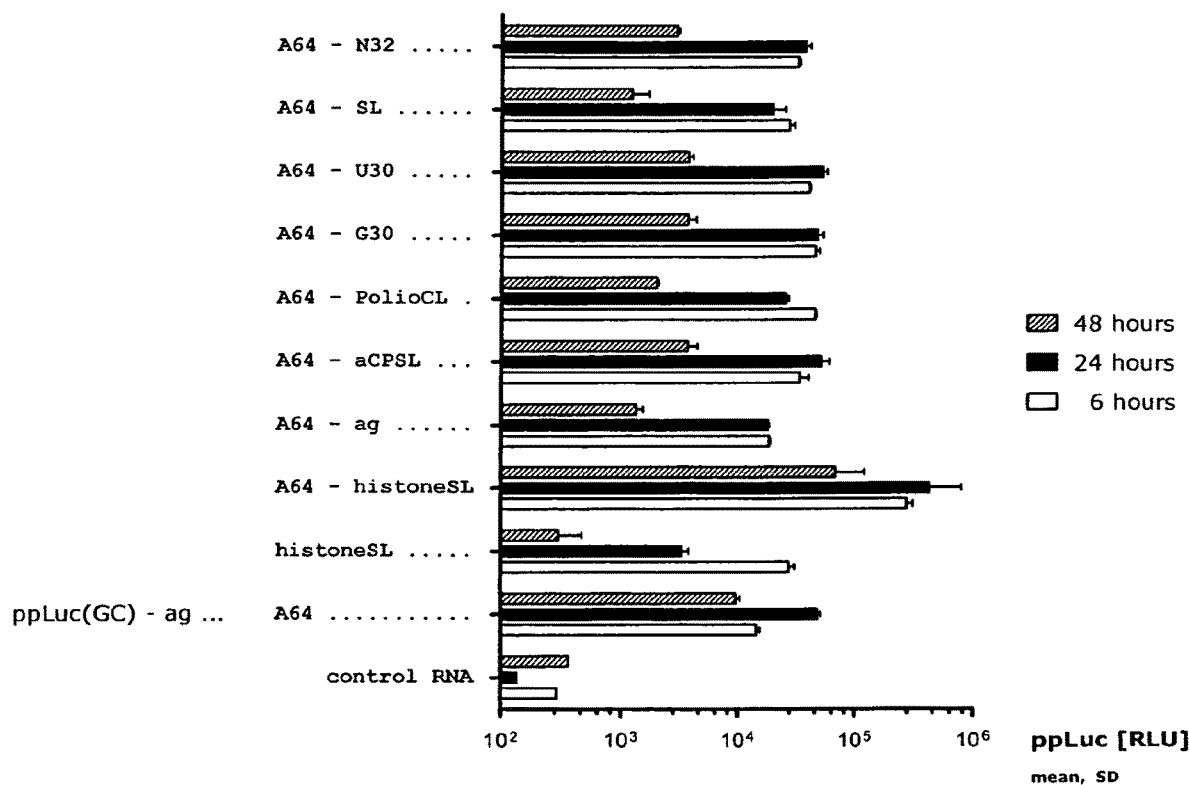
FIG. 22: shows that the rise in protein expression by the combination of poly(A) and histoneSL is specific. The effect of combining poly(A) and histoneSL or poly(A) and alternative sequences on luciferase expression from mRNA was examined Therefore different mRNAs were electroporated into HeLa cells. Luciferase levels were measured at 6, 24, and 48 hours after transfection. Both a poly(A) sequence or the histoneSL give rise to comparable luciferase levels. The combination of poly(A) and histoneSL strongly increases the luciferase level, manifold above the level observed with either of the individual elements, thus acting synergistically. In contrast, combining poly(A) with any of the other sequences is without effect on the luciferase level compared to mRNA containing only a poly(A) sequence. Thus, the combination of poly(A) and histoneSL acts specifically and synergistically. Data are graphed as mean RLU±SD for triplicate transfections. Specific RLU are summarized in Example 11.4.

11.4 the Rise in Protein Expression by the Combination of Poly(A) and histoneSL is Specific To investigate whether the effect of the combination of poly(A) and histoneSL on protein expression from mRNA is specific, mRNAs with alternative sequences in combination with poly(A) were synthesized: These mRNAs contained 3' of A64 one of seven distinct sequences, respectively. Luciferase-encoding mRNAs or control mRNA were electroporated into HeLa cells. Luciferase levels were measured at 6, 24, and 48 hours after transfection (see following Table 11 and FIG. 22).

TABLE 11

| mRNA | RLU at 6 hours | RLU at 24 hours | RLU at 48 hours |
|---|---|---|---|
| ppLuc(GC)-ag-A64-N32 | 33501 | 38979 | 2641 |
| ppLuc(GC)-ag-A64-SL | 28176 | 20364 | 874 |
| ppLuc(GC)-ag-A64-U30 | 41632 | 54676 | 3408 |
| ppLuc(GC)-ag-A64-G30 | 46763 | 49210 | 3382 |
| ppLuc(GC)-ag-A64-PolioCL | 46428 | 26090 | 1655 |
| ppLuc(GC)-ag-A64-aCPSL | 34176 | 53090 | 3338 |
| ppLuc(GC)-ag-A64-ag | 18534 | 18194 | 989 |
| ppLuc(GC)-ag-A64-histoneSL | 282677 | 437543 | 69292 |
| ppLuc(GC)-ag-histoneSL | 27597 | 3171 | 0 |
| ppLuc(GC)-ag-A64 | 14339 | 48414 | 9357 |

Both a poly(A) sequence or the histoneSL gave rise to comparable luciferase levels. Again, the combination of poly(A) and histoneSL strongly increased the luciferase level, manifold above the level observed with either of the individual elements, thus acting synergistically. In contrast, combining poly(A) with any of the alternative sequences was without effect on the luciferase level compared to mRNA containing only a poly(A) sequence. Thus, the combination of poly(A) and histoneSL increases protein expression from mRNA in a synergistic manner, and this effect is specific.

11.5 the Combination of Poly(A) and histoneSL Increases Protein Expression from mRNA in a Synergistic Manner In Vivo.

Figure 23:
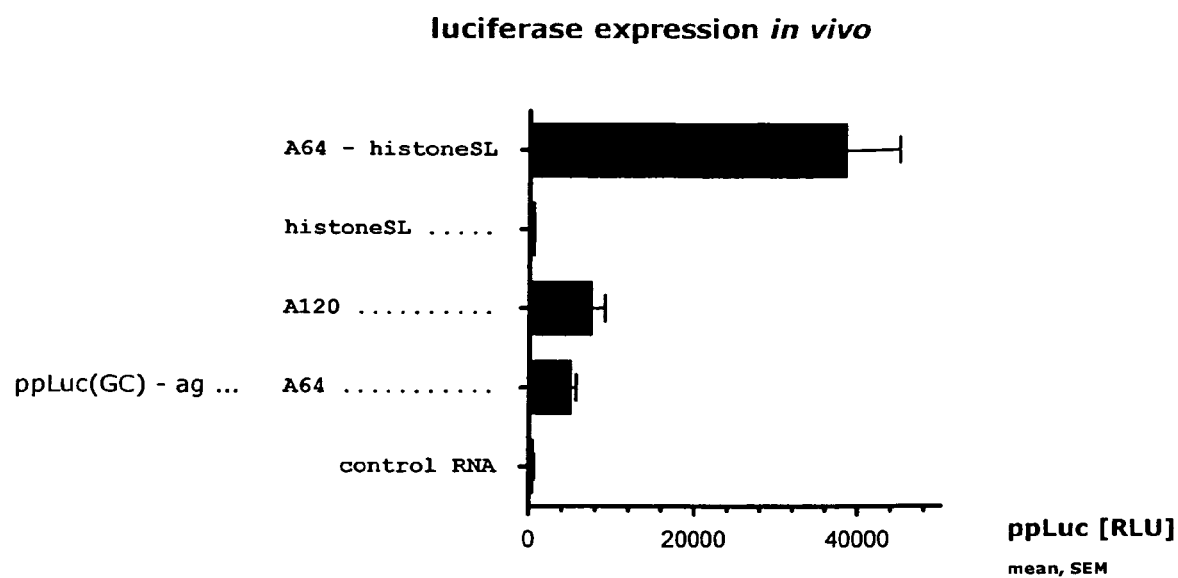
FIG. 23: shows that the combination of poly(A) and histoneSL increases protein expression from mRNA in a synergistic manner in vivo. The effect of poly(A) sequence, histoneSL, and the combination of poly(A) and histoneSL on luciferase expression from mRNA in vivo was examined Therefore different mRNAs were injected intradermally into mice. Mice were sacrificed 16 hours after injection and Luciferase levels at the injection sites were measured. Luciferase is expressed from mRNA having either a histoneSL or a poly(A) sequence. Strikingly however, the combination of poly(A) and histoneSL strongly increases the luciferase level, manifold above the level observed with either of the individual elements, thus acting synergistically. Data are graphed as mean RLU±SEM (relative light units±standard error of mean). Specific RLU are summarized in Example 11.5.

To investigate the effect of the combination of poly(A) and histoneSL on protein expression from mRNA in vivo, Luciferase-encoding mRNAs with different sequences 3' of the alpha-globin 3'-UTR or control mRNA were injected intradermally into mice: mRNAs contained either an A64 poly(A) sequence or a histoneSL instead, or both A64 poly(A) and histoneSL 3' of the 3'-UTR. Luciferase levels were measured at 16 hours after injection (see following Table 12 and FIG. 23).

TABLE 12

| mRNA | RLU at 16 hours |
|---|---|
| ppLuc(GC)-ag-A64-histoneSL | 38081 |
| ppLuc(GC)-ag-histoneSL | 137 |
| ppLuc(GC)-ag-A64 | 4607 |

Luciferase was expressed from mRNA having either a histoneSL or a poly(A) sequence. Strikingly however, the combination of poly(A) and histoneSL further strongly increased the luciferase level, manifold above the level observed with either of the individual elements. The magnitude of the rise in luciferase level due to combining poly(A) and histoneSL in the same mRNA demonstrates that they are acting synergistically.

The synergy between poly(A) and histoneSL was quantified by dividing the signal from poly(A)-histoneSL mRNA (+/+) by the sum of the signals from histoneSL mRNA (−/+) plus poly(A) mRNA (+/−) (see following Table 13).

TABLE 13

|  | A64 | histoneSL | RLU at 16 hours |
|---|---|---|---|
|  | + | + | 38081 |
|  | − | + | 137 |
|  | + | − | 4607 |
| Synergy |  |  | 8.0 |

The factor thus calculated specifies how much higher the luciferase level from mRNA combining poly(A) and histoneSL is than would be expected if the effects of poly(A) and histoneSL were purely additive. The luciferase level from mRNA combining poly(A) and histoneSL was 8 times higher than if their effects were purely additive. This result confirms that the combination of poly(A) and histoneSL effects a markedly synergistic increase in protein expression in vivo.

11.6 the Combination of Poly(A) and histoneSL Increases the Level of Antibodies Elicited by Vaccination with mRNA.

To investigate the effect of the combination of poly(A) and histoneSL on the induction of antibodies elicited by vaccination with mRNA, Balb/c mice were vaccinated intradermally with, HA-encoding mRNAs with different sequences 3' of the mutated alpha-globin 3'-UTR. mRNAs contained either an A64 poly(A) sequence or both A64 poly(A) and histoneSL 3' of the 3'-UTR. The level of HA-specific antibodies in vaccinated and control mice was analyzed by ELISA with serial dilutions of sera (see FIG. 24).

Anti HA IgG1 was induced by mRNA having only a poly(A) sequence. Strikingly however, the combination of poly(A) and histoneSL strongly increased the anti HA IgG1 level, above the level observed with only a poly(A) sequence.

The invention claimed is:

1. A method of stimulating an immune response in a subject comprising administering an effective amount a composition to the subject, said composition comprising a mRNA encoding a Severe Acute Respiratory Syndrome (SARS) coronavirus spike(S) protein coding sequence and a histone stem loop sequence, said mRNA provided in complex with a lipid.

2. The method of claim 1, wherein the composition is administered by intradermal or intramuscular injection.

3. The method of claim 2, wherein the composition is administered by intramuscular injection.

4. The method of claim 1, wherein the mRNA comprises a Poly-A sequence.

5. The method of claim 4, wherein the mRNA comprises a Poly-A sequence of about 25 to 400 adenosine nucleotides.

6. The method of claim 1, wherein the mRNA comprises a 5' untranslated region (UTR) and/or a 3' UTR.

7. The method of claim 6, wherein the mRNA comprises a 5'UTR and a 3' UTR.

8. The method of claim 1, wherein the lipid comprises a cationic lipid.

9. The method of claim 1, wherein the coding sequence of the mRNA has a G/C content that is increased compared with the G/C content of the coding sequence of a wild-type RNA.

10. The method of claim 1, wherein the mRNA comprises a nucleotide analog substitution.

11. The method of claim 10, wherein the nucleotide analog substation comprises at least one pseudouridine-5'-triphosphate substitution.

12. The method of claim 1, wherein the mRNA comprises a methylated 5' cap.

13. The method of claim 1, further comprising a polyethyleneglycol.

14. The method of claim 1, further comprising an adjuvant.

15. The method of claim 1, wherein the mRNA comprises a methylated 5' cap; a 5' UTR; a 3' UTR and a Poly-A sequence of about 25 to 400 adenosine nucleotides.

16. The method of claim 15, wherein the coding sequence of the mRNA has a G/C content that is increased compared with the G/C content of the coding sequence of a wild-type RNA.

17. The method of claim 16, wherein the lipid comprises a cationic lipid.

18. The method of claim 1, wherein the histone stem loop sequence is at least 90% identical to the sequence of SEQ ID NO: 39 or SEQ ID NO: 42.

19. The method of claim 18, wherein the histone stem loop sequence is at least 90% identical to the sequence of SEQ ID NO: 39.

20. A method of stimulating an immune response in a subject comprising administering an effective amount a composition to the subject, said composition comprising a purified mRNA encoding: a 5' UTR; a coronaviruses spike (S) protein coding sequence; a 3' UTR; a Poly-A sequence of 25 to 400 adenosine nucleotides; and a histone stem loop sequence, said mRNA comprising a 5' Cap, wherein the purified mRNA is provided in complex with a lipid.

21. The method of claim 20, wherein the composition is administered by intradermal or intramuscular injection.

22. The method of claim 21, wherein the lipid comprises a cationic lipid.

23. The method of claim 20, wherein the coding sequence of the mRNA has a G/C content that is increased compared with the G/C content of the coding sequence of a wild-type RNA.

* * * * *